(12) United States Patent
Truckai et al.

(10) Patent No.: US 8,066,712 B2
(45) Date of Patent: Nov. 29, 2011

(54) SYSTEMS FOR DELIVERING BONE FILL MATERIAL

(75) Inventors: Csaba Truckai, Saratoga, CA (US); John H. Shadduck, Tiburon, CA (US)

(73) Assignee: DFINE, Inc., San Jose, CA (US)

( * ) Notice: Subject to any disclaimer, the term of this patent is extended or adjusted under 35 U.S.C. 154(b) by 755 days.

(21) Appl. No.: 11/469,752

(22) Filed: Sep. 1, 2006

(65) Prior Publication Data

US 2007/0191858 A1    Aug. 16, 2007

Related U.S. Application Data

(60) Provisional application No. 60/762,611, filed on Jan. 27, 2006, provisional application No. 60/788,755, filed on Apr. 3, 2006.

(51) Int. Cl.
*A61B 17/00*    (2006.01)

(52) U.S. Cl. .............................. 606/93; 606/92; 606/94

(58) Field of Classification Search ............... 606/92–94
See application file for complete search history.

(56) References Cited

U.S. PATENT DOCUMENTS

| | | | |
|---|---|---|---|
| 3,349,840 A * | 10/1967 | Tope et al. ................... | 165/259 |
| 4,250,887 A | 2/1981 | Dardik et al. | |
| 4,265,618 A | 5/1981 | Herskovitz et al. | |
| 4,377,168 A * | 3/1983 | Rzasa et al. ................... | 606/24 |
| 4,671,263 A | 6/1987 | Draenert | |
| 4,772,287 A | 9/1988 | Ray et al. | |
| 4,815,454 A | 3/1989 | Dozier | |
| 5,037,437 A | 8/1991 | Matsen | |
| 5,130,950 A | 7/1992 | Orban et al. | |

(Continued)

FOREIGN PATENT DOCUMENTS

WO    WO 2004/075954    9/2004

(Continued)

OTHER PUBLICATIONS

Office Action in U.S. Appl. No. 11/469,769, mailed Dec. 11, 2008.

(Continued)

*Primary Examiner* — Eduardo C Robert
*Assistant Examiner* — Julianna N Harvey
(74) *Attorney, Agent, or Firm* — Knobbe, Martens, Olson & Bear, LLP

(57) ABSTRACT

The disclosure relates in certain embodiments to medical devices, systems and methods for use in osteoplasty procedures, such as vertebral compression fractures. One system for delivering a bone fill material to a bone includes an elongated introducer configured for insertion into a bone and having a channel sized to allow a flow of bone fill material therethrough. The introducer has at least one outlet opening in communication with the channel for delivering the bone fill material into the bone. A thermal energy emitter is coupled to the introducer and configured to apply thermal energy to the bone fill material flowing through the introducer. A sensor and a computer controller can be used to measure data about the bone fill material and to control certain aspects of the flow of bone fill material. A hydraulic pressure source may also be operatively coupled to the introducer and configured to apply a force on the bone fill material to provide a pressurized flow of bone fill material through the introducer. In certain embodiments, the system for use in osteoplasty procedures can include a cooling system that can be used to cool the bone fill material.

32 Claims, 34 Drawing Sheets

U.S. PATENT DOCUMENTS

| | | |
|---|---|---|
| 5,145,250 A | 9/1992 | Planck et al. |
| 5,324,305 A | 6/1994 | Kanner |
| 5,542,928 A * | 8/1996 | Evans et al. .................... 604/113 |
| 5,788,711 A | 8/1998 | Lehner et al. |
| 5,954,716 A | 9/1999 | Sharkey et al. |
| 6,075,067 A * | 6/2000 | Lidgren ........................ 523/116 |
| 6,077,256 A | 6/2000 | Mann |
| 6,122,549 A | 9/2000 | Sharkey et al. |
| 6,171,312 B1 | 1/2001 | Beaty |
| 6,228,072 B1 | 5/2001 | Omaleki et al. |
| 6,231,615 B1 | 5/2001 | Preissman |
| 6,235,043 B1 | 5/2001 | Reiley et al. |
| 6,236,020 B1 | 5/2001 | Friedman |
| 6,241,734 B1 | 6/2001 | Scribner |
| 6,248,110 B1 | 6/2001 | Reiley et al. |
| 6,264,659 B1 * | 7/2001 | Ross et al. ....................... 606/93 |
| 6,280,456 B1 | 8/2001 | Scribner |
| 6,309,420 B1 | 10/2001 | Preissman |
| 6,312,254 B1 | 11/2001 | Friedman |
| 6,348,055 B1 | 2/2002 | Preissman |
| 6,383,190 B1 | 5/2002 | Preissman |
| 6,395,007 B1 | 5/2002 | Bhatnagar et al. |
| 6,436,143 B1 | 8/2002 | Ross et al. |
| 6,458,127 B1 | 10/2002 | Truckai |
| 6,524,102 B2 | 2/2003 | Davis |
| 6,575,331 B1 | 6/2003 | Peeler et al. |
| 6,610,079 B1 | 8/2003 | Li et al. |
| 6,613,054 B2 | 9/2003 | Scribner et al. |
| 6,620,185 B1 | 9/2003 | Harvie et al. |
| 6,632,235 B2 | 10/2003 | Weikel et al. |
| 6,662,969 B2 | 12/2003 | Peeler et al. |
| 6,676,664 B1 | 1/2004 | Al-Assir |
| 6,726,691 B2 | 4/2004 | Osorio |
| 6,736,537 B2 | 5/2004 | Coffeen et al. |
| 6,783,515 B1 | 8/2004 | Miller |
| 6,814,736 B2 | 11/2004 | Reiley |
| 6,899,713 B2 | 5/2005 | Shaolian et al. |
| 6,929,640 B1 | 8/2005 | Underwood |
| 6,957,747 B2 | 10/2005 | Peeler et al. |
| 6,958,061 B2 | 10/2005 | Truckai |
| 6,964,667 B2 | 11/2005 | Shaolian et al. |
| 6,979,352 B2 | 12/2005 | Reynolds |
| 7,008,433 B2 | 3/2006 | Voellmicke et al. |
| 7,048,743 B2 | 5/2006 | Miller et al. |
| 7,081,125 B2 | 7/2006 | Edwards et al. |
| 7,112,205 B2 | 9/2006 | Carrison |
| 7,153,306 B2 | 12/2006 | Ralph |
| 7,153,307 B2 | 12/2006 | Scribner et al. |
| 7,160,020 B2 | 1/2007 | Sand |
| 7,361,368 B2 | 4/2008 | Claude et al. |
| 7,399,306 B2 | 7/2008 | Reiley et al. |
| 7,559,932 B2 | 7/2009 | Truckai et al. |
| 7,572,263 B2 | 8/2009 | Preissman |
| 7,662,133 B2 | 2/2010 | Scarborough et al. |
| 7,678,116 B2 | 3/2010 | Truckai et al. |
| 7,717,918 B2 | 5/2010 | Truckai et al. |
| 7,722,620 B2 | 5/2010 | Truckai et al. |
| 2002/0026195 A1 | 2/2002 | Layne et al. |
| 2002/0068974 A1 | 6/2002 | Kuslich et al. |
| 2002/0082608 A1 | 6/2002 | Reiley et al. |
| 2002/0099385 A1 | 7/2002 | Ralph et al. |
| 2002/0108743 A1 * | 8/2002 | Wirtz ............................ 165/185 |
| 2002/0147497 A1 | 10/2002 | Belef et al. |
| 2002/0156483 A1 | 10/2002 | Voellmicke et al. |
| 2002/0161373 A1 | 10/2002 | Osorio et al. |
| 2002/0174861 A1 * | 11/2002 | Lundt et al. ...................... 125/21 |
| 2003/0012080 A1 * | 1/2003 | Coffeen et al. ............... 366/139 |
| 2003/0032733 A1 | 2/2003 | Fisher et al. |
| 2003/0130738 A1 | 7/2003 | Hovda et al. |
| 2003/0171748 A1 | 9/2003 | Truckai et al. |
| 2003/0220648 A1 | 11/2003 | Osorio et al. |
| 2003/0233096 A1 | 12/2003 | Osorio et al. |
| 2004/0006347 A1 | 1/2004 | Sproul |
| 2004/0024410 A1 | 2/2004 | Olson, Jr. et al. |
| 2004/0059328 A1 | 3/2004 | Daniel et al. |
| 2004/0083002 A1 | 4/2004 | Belef et al. |
| 2004/0092892 A1 | 5/2004 | Kagen et al. |
| 2004/0092948 A1 | 5/2004 | Stevens et al. |
| 2004/0110285 A1 | 6/2004 | Lendlein et al. |
| 2004/0127475 A1 | 7/2004 | New et al. |
| 2004/0172132 A1 | 9/2004 | Ginn |
| 2004/0186576 A1 | 9/2004 | Biscup et al. |
| 2004/0193171 A1 | 9/2004 | DiMauro et al. |
| 2004/0215202 A1 | 10/2004 | Preissman |
| 2004/0225296 A1 | 11/2004 | Reiss et al. |
| 2004/0228898 A1 | 11/2004 | Ross et al. |
| 2004/0267271 A9 | 12/2004 | Scribner et al. |
| 2005/0010231 A1 | 1/2005 | Myers |
| 2005/0059979 A1 | 3/2005 | Yetkinler et al. |
| 2005/0070915 A1 | 3/2005 | Mazzuca et al. |
| 2005/0113843 A1 | 5/2005 | Arramon |
| 2005/0119650 A1 | 6/2005 | Sanders et al. |
| 2005/0222681 A1 | 10/2005 | Richley et al. |
| 2005/0245938 A1 | 11/2005 | Kochan |
| 2005/0251149 A1 | 11/2005 | Wenz |
| 2006/0052743 A1 | 3/2006 | Reynolds |
| 2006/0052794 A1 | 3/2006 | McGill et al. |
| 2006/0074433 A1 | 4/2006 | McGill et al. |
| 2006/0079905 A1 | 4/2006 | Beyar et al. |
| 2006/0122614 A1 | 6/2006 | Truckai et al. |
| 2006/0122621 A1 | 6/2006 | Truckai et al. |
| 2006/0122622 A1 | 6/2006 | Truckai et al. |
| 2006/0122623 A1 | 6/2006 | Truckai et al. |
| 2006/0122624 A1 | 6/2006 | Truckai et al. |
| 2006/0122625 A1 | 6/2006 | Truckai et al. |
| 2006/0150862 A1 | 7/2006 | Zhao et al. |
| 2006/0182780 A1 | 8/2006 | Riley et al. |
| 2006/0264967 A1 | 11/2006 | Ferreyro et al. |
| 2007/0027230 A1 | 2/2007 | Beyar et al. |
| 2007/0032785 A1 | 2/2007 | Diederich et al. |
| 2007/0112299 A1 | 5/2007 | Smit et al. |
| 2007/0137285 A1 * | 6/2007 | Jennings ...................... 73/53.01 |
| 2007/0185231 A1 | 8/2007 | Liu et al. |
| 2007/0198023 A1 | 8/2007 | Sand et al. |
| 2007/0233148 A1 | 10/2007 | Truckai et al. |
| 2007/0282346 A1 | 12/2007 | Scribner et al. |
| 2008/0103505 A1 | 5/2008 | Fransen |
| 2008/0195112 A1 | 8/2008 | Liu et al. |
| 2009/0024161 A1 | 1/2009 | Bonutti et al. |

FOREIGN PATENT DOCUMENTS

WO    WO 2004/075954 A2 *   9/2004

OTHER PUBLICATIONS

Office Action in U.S. Appl. No. 11/953,800 mailed April 29, 2009.
Office Action in U.S. Appl. No. 11/469,769 mailed Oct. 2, 2009.
Office Action in U.S. Appl. No. 11/469,764 mailed Jul. 2, 2009.
Office Action in U.S. Appl. No. 11/469,764 mailed Apr. 6, 2010.

* cited by examiner

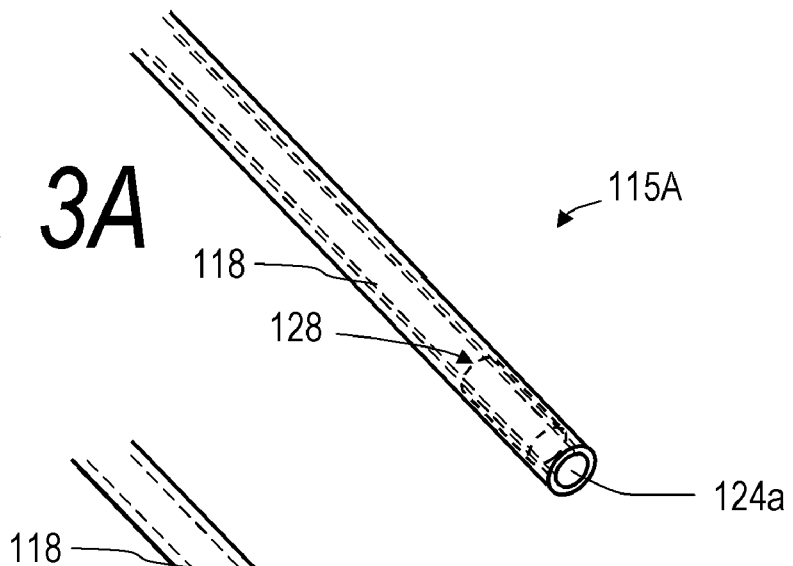
FIG. 3A
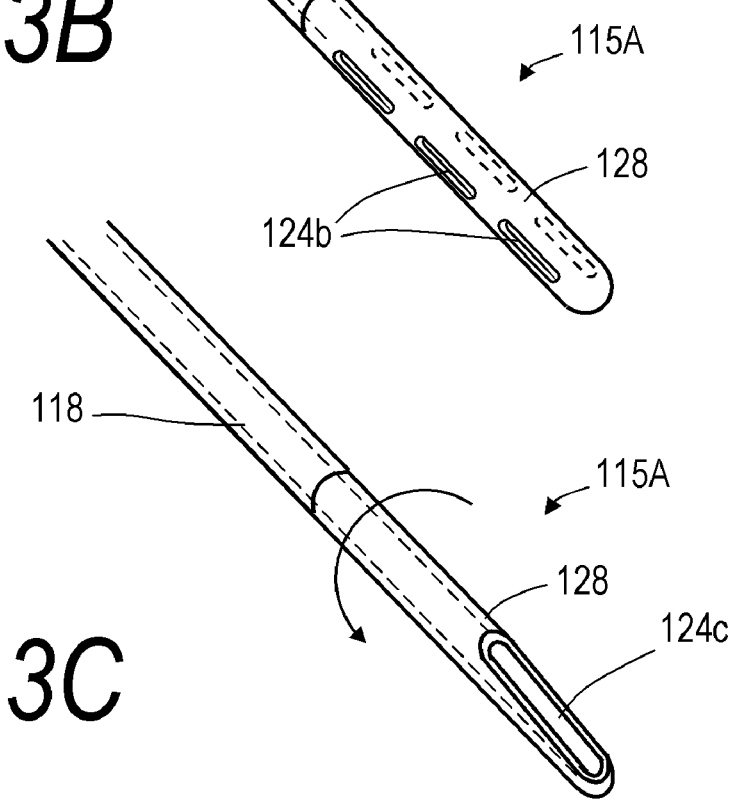
FIG. 3B
FIG. 3C

SYSTEMS FOR DELIVERING BONE FILL MATERIAL

CROSS-REFERENCE TO RELATED APPLICATIONS

This application claims the benefit of U.S. Provisional Patent Application No. 60/762,611, filed Jan. 27, 2006, and of U.S. Provisional Application No. 60/788,755, filed Apr. 3, 2006, the entire contents of which are hereby incorporated by reference and should be considered a part of this specification.

BACKGROUND OF THE INVENTION

1. Field of the Invention

The present invention relates in certain embodiments to medical devices for osteoplasty treatment procedures, such as vertebral compression fractures. More particularly, embodiments of the invention relate to systems for delivering a bone fill material into a bone, such as a vertebral body.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the population affected will grow steadily as life expectancy increases. Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of with collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. Vertebroplasty is the percutaneous injection of PMMA (polymethylmethacrylate) into a fractured vertebral body via a trocar and cannula. The targeted vertebrae are identified under fluoroscopy. A needle is introduced into the vertebrae body under fluoroscopic control, to allow direct visualization. A bilateral transpedicular (through the pedicle of the vertebrae) approach is typical but the procedure can be done unilaterally. The bilateral transpedicular approach allows for more uniform PMMA infill of the vertebra.

In a bilateral approach, approximately 1 to 4 ml of PMMA is used on each side of the vertebra. Since the PMMA needs to be is forced into the cancellous bone, the techniques require high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasion are critical to the technique—and the physician terminates PMMA injection when leakage is evident. The cement is injected using syringes to allow the physician manual control of injection pressure.

Kyphoplasty is a modification of percutaneous vertebroplasty. Kyphoplasty involves a preliminary step consisting of the percutaneous placement of an inflatable balloon tamp in the vertebral body. Inflation of the balloon creates a cavity in the bone prior to cement injection. The proponents of percutaneous kyphoplasty have suggested that high pressure balloon-tamp inflation can at least partially restore vertebral body height. In kyphoplasty, some physicians state that PMMA can be injected at a lower pressure into the collapsed vertebra since a cavity exists, when compared to conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles.

Leakage of PMMA during vertebroplasty can result in very serious complications including compression of adjacent structures that necessitate emergency decompressive surgery. See "Anatomical and Pathological Considerations in Percutaneous Vertebroplasty and Kyphoplasty: A Reappraisal of the Vertebral Venous System", Groen, R. et al, Spine Vol. 29, No. 13, pp 1465-1471 2004. Leakage or extravasion of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al, "The Analysis of Polymethylmethacrylate Leakage after Vertebroplasty for Vertebral Body Compression Fractures", Jour. of Korean Neurosurg. Soc. Vol. 35, No. 5 (5/2004) pp. 478-82, (http://wwwjkns.or.kr/htm/abstract.asp?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol. 2004 February; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al, "Asymptomatic diffuse pulmonary embolism caused by acrylic cement: an unusual complication of percutaneous vertebroplasty", Ann. Rheum. Dis. 2003; 62:85-86. The vapors from PMMA preparation and injection also are cause for concern. See Kirby, B, et al., "Acute bronchospasm due to exposure to polymethylmethacrylate vapors during percutaneous vertebroplasty", Am. J. Roentgenol. 2003; 180:543-544.

In both higher pressure cement injection (vertebroplasty) and balloon-tamped cementing procedures (kyphoplasty), the methods do not provide for well controlled augmentation of vertebral body height. The direct injection of bone cement simply follows the path of least resistance within the fractured bone. The expansion of a balloon applies also compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to 200 or 300 psi) to inflate the balloon which crushes and compacts cancellous bone. Expansion of the balloon under high pressures close to cortical bone can fracture the cortical bone, typically the endplates, which can cause regional damage to the cortical bone with the risk of cortical bone necrosis. Such cortical bone damage is highly undesirable as the endplate and adjacent structures provide nutrients for the disc.

Kyphoplasty also does not provide a distraction mechanism capable of 100% vertebral height restoration. Further, the kyphoplasty balloons under very high pressure typically apply forces to vertebral endplates within a central region of the cortical bone that may be weak, rather than distributing forces over the endplate.

There is a general need to provide bone cements and methods for use in treatment of vertebral compression fractures that provide a greater degree of control over introduction of cement and that provide better outcomes. Embodiments of the present invention meet this need and provide several other advantages in a novel and nonobvious manner.

SUMMARY OF THE INVENTION

Certain embodiments of the invention provide systems and methods for treating bone, such as a vertebra, by delivering bone fill material into the interior of the vertebra. One embodiment utilizes Rf energy or other energy sources to controllably elevate the temperature of bone fill material flows as the flows exit the working end of an introducer. A computer controller controls the bone fill material flow parameters and energy delivery parameters for selectively polymerizing the fill material inflow plume to thereby control the direction of flow and the ultimate geometry of a flowable, in-situ hardenable bone fill material. The system and method further includes means for sealing tissue in the interior of a vertebra to prevent migration of monomers, fat or emboli into the patient's bloodstream.

In another embodiment, a controller is provided to control all parameters of bone fill material injection. For example, the controller can control bone fill material inflow parameters from, for example, a hydraulic mechanism. The controller can also control the sensing system and energy delivery parameters for selectively heating tissue or polymerizing bone fill material at both the interior and exterior of the introducer. The workload on a physician during an osteoplasty procedure can thus advantageously be reduced.

In one embodiment, a system for delivering a bone fill material to a vertebra is provided. The system comprises an elongated introducer configured for insertion into a vertebral body and delivery of bone fill material through a channel of the introducer into the vertebral body. The system also comprises a container of bone fill material coupleable to the introducer and a thermal energy emitter coupled to the introducer, the thermal energy emitter configured to apply thermal energy to the bone fill material flowing through the introducer. The system further comprises a hydraulic pressure source coupled to the container and configured to apply a force on the bone fill material in the container to eject bone fill material from the container into the introducer.

In another embodiment, a system for delivering a bone fill material to a bone is provided. The system comprises an elongated introducer configured for insertion into a bone. The introducer defines a channel sized to allow a flow of a bone fill material therethrough. The introducer also has at least one opening in communication with the channel for delivering the bone fill material into the bone. The system also comprises a thermal energy emitter coupled to the introducer and configured to apply thermal energy to the bone fill material flowing through the introducer. The system further comprises a hydraulic pressure source operatively coupled to the introducer and configured to apply a force on the bone fill material to provide a pressurized flow of bone fill material through the introducer.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 3A is a schematic perspective view of a working end of an introducer, in accordance with one embodiment.

FIG. 3B is a schematic perspective view of a working end of an introducer, in accordance with another embodiment.

FIG. 3C is a schematic perspective view of a working end of an introducer, in accordance with yet another embodiment.

DETAILED DESCRIPTION OF THE PREFERRED EMBODIMENTS

Definitions

Figure 1:
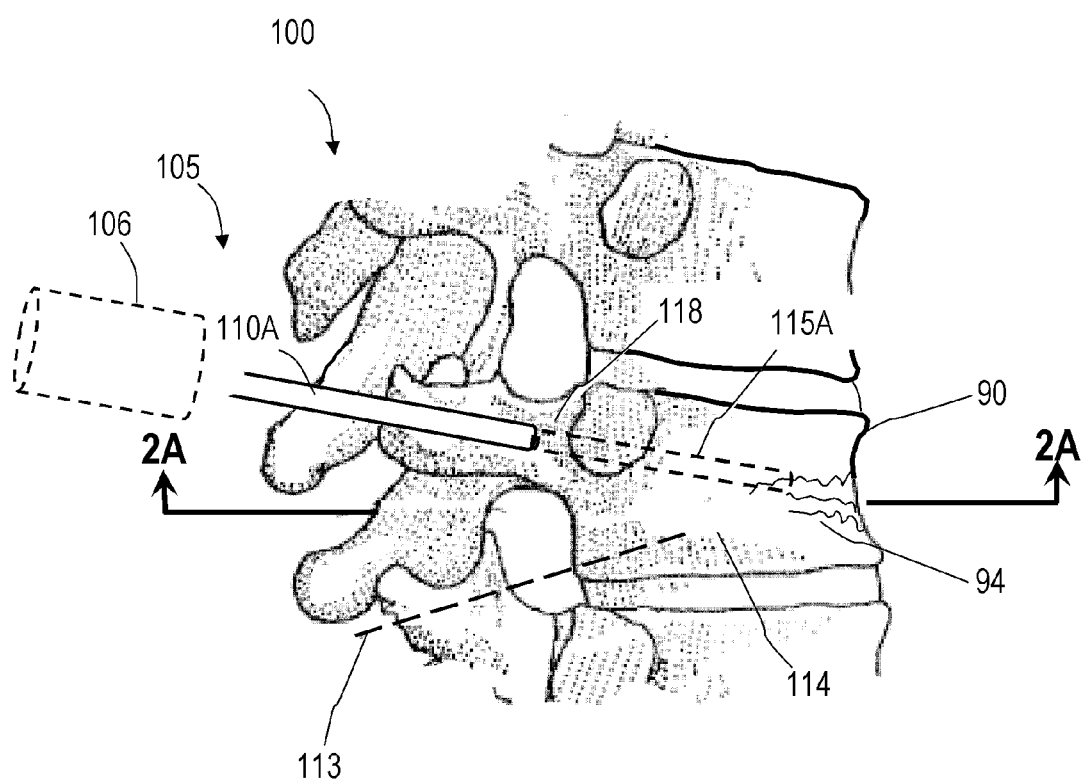
FIG. 1 is a schematic side view of a spine segment showing a vertebra with a compression fracture and an introducer, in accordance with one embodiment disclosed herein.

"Bone fill material, infill material or composition" includes its ordinary meaning and is defined as any material for infilling a bone that includes an in-situ hardenable material, such as bone cement. The fill material also can include other "fillers" such as filaments, microspheres, powders, granular elements, flakes, chips, tubules and the like, autograft or allograft materials, as well as other chemicals, pharmacological agents or other bioactive agents.

"Flowable material" includes its ordinary meaning and is defined as a material continuum that is unable to withstand a static shear stress and responds with an irrecoverable flow (a fluid)—unlike an elastic material or elastomer that responds to shear stress with a recoverable deformation. Flowable material includes fill material or composites that include a fluid (first) component and an elastic or inelastic material (second) component that responds to stress with a flow, no matter the proportions of the first and second component, and wherein the above shear test does not apply to the second component alone.

An "elastomer" includes its ordinary meaning and is defined as material having to some extent the elastic properties of natural rubber wherein the material resumes or moves toward an original shape when a deforming force is removed.

"Substantially" or "substantial" mean largely but not necessarily entirely. For example, substantially may mean about 10% to about 99.999%, about 25% to about 99.999% or about 50% to about 99.999%.

"Osteoplasty" includes its ordinary meaning and means any procedure wherein fill material is delivered into the interior of a bone.

"Vertebroplasty" includes its ordinary meaning and means any procedure wherein fill material is delivered into the interior of a vertebra.

Systems and Methods of Infill Material Delivery and Energy Application

For the purpose of understanding the principles of the invention, reference will now be made to the embodiments illustrated in the drawings and accompanying text that describe the invention. Further details on systems and methods for the delivery of bone cement can be found in U.S. patent application Ser. No. 11/165,652, filed Jun. 24, 2005, now U.S. Pub. No. 2006-0122623; U.S. application Ser. No. 11/196,045, filed Aug. 2, 2005, now U.S. Pub. No. 2006-0122624; U.S. application Ser. No. 11/208,448, filed Aug. 20, 2005, now U.S. Pub. No. 2006-0122621; and U.S. application Ser. No. 11/209,035, filed Aug. 22, 2005, now U.S. Pub. No. 2006-0122625, the entire contents of which are hereby incorporated by reference and should be considered a part of this specification.

FIG. 1 illustrates one embodiment of the invention for treating a spine segment in which a vertebral body 90 has a wedge compression fracture indicated at 94. In one embodiment, the systems and methods are directed to safely introducing a bone fill material into cancellous bone of the vertebra without extravasation of fill material in unwanted directions (i) to prevent micromotion in the fracture for eliminating pain, and (ii) to support the vertebra and increase vertebral body height. Further, systems and methods are provided for sealing cancellous bone (e.g., blood vessels, fatty tissues etc.) in order to prevent monomers, fat, fill material and other emboli from entering the venous system during treatment.

Figure 2A:
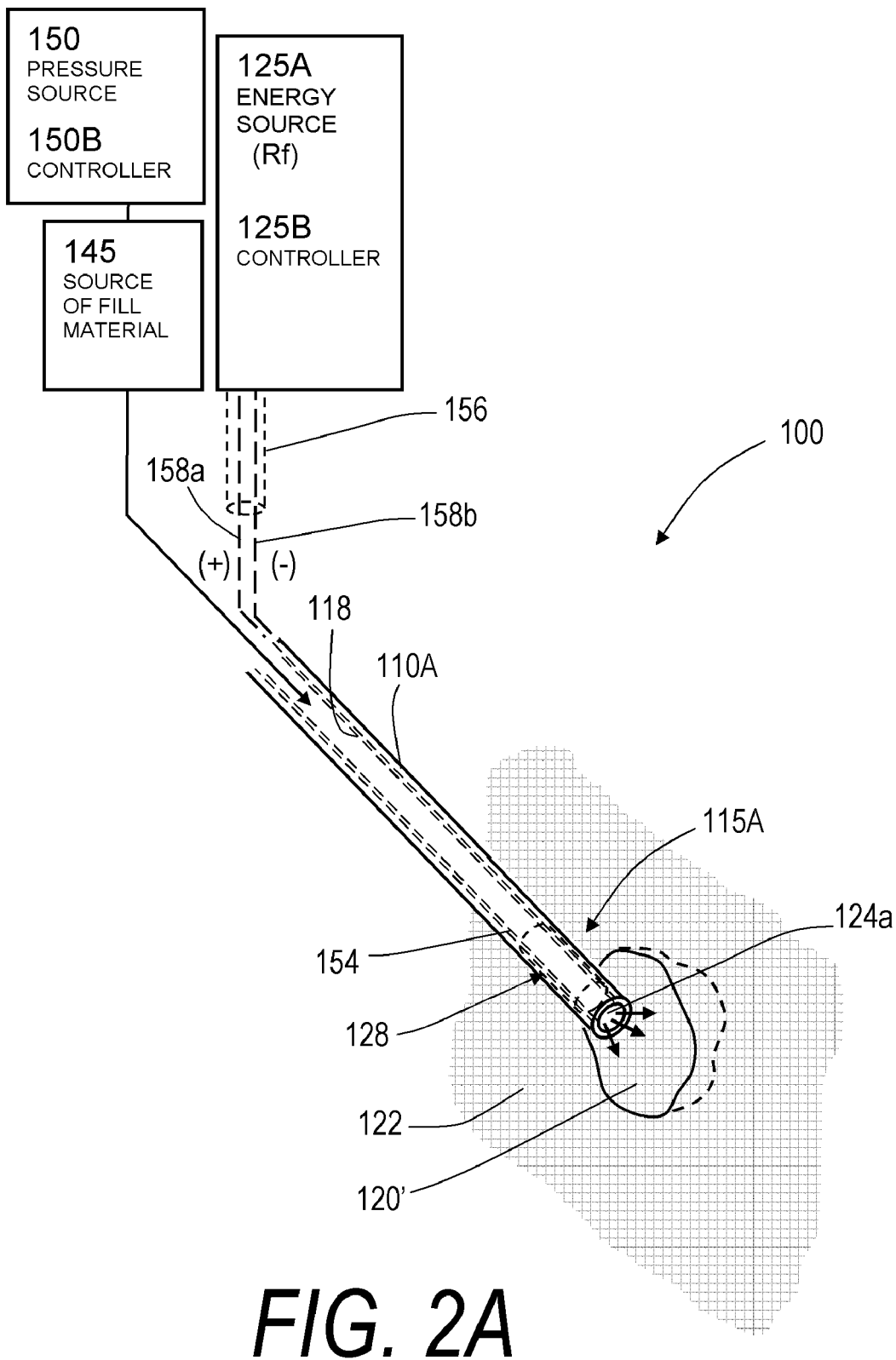
FIG. 2A is a schematic perspective view of a system for treating bone, in accordance with one embodiment.

FIG. 1 illustrates a fractured vertebra and bone infill system 100 which includes probe 105 having a handle end 106 extending to an elongated introducer 110A and working end 115A, shown in FIG. 2A. The introducer is shown introduced through pedicle 118 of the vertebra for accessing the osteoporotic cancellous bone 122 (See FIG. 2A). The initial aspects of the procedure are similar to conventional percutaneous vertebroplasty wherein the patient is placed in a prone position on an operating table. The patient is typically under conscious sedation, although general anesthesia is an alternative. The physician injects a local anesthetic (e.g., 1% Lidocaine) into the region overlying the targeted pedicle or pedicles as well as the periosteum of the pedicle(s). Thereafter, the physician uses a scalpel to make a 1 to 5 mm skin incision over each targeted pedicle. Thereafter, the introducer 110A is advanced through the pedicle into the anterior region of the vertebral body, which typically is the region of greatest compression and fracture. The physician confirms the introducer path posterior to the pedicle, through the pedicle and within the vertebral body by anteroposterior and lateral X-Ray projection fluoroscopic views. The introduction of infill material as described below can be imaged several times, or continuously, during the treatment depending on the imaging method.

It should be appreciated that the introducer also can be introduced into the vertebra from other angles, for example, along axis 113 through the wall of the vertebral body 114 as in FIG. 1 or in an anterior approach (not shown). Further, first and second cooperating introducers can be used in a bilateral transpedicular approach. Additionally, any mechanism known in the art for creating an access opening into the interior of the vertebral body 90 can be used, including open surgical procedures.

Figure 2B:
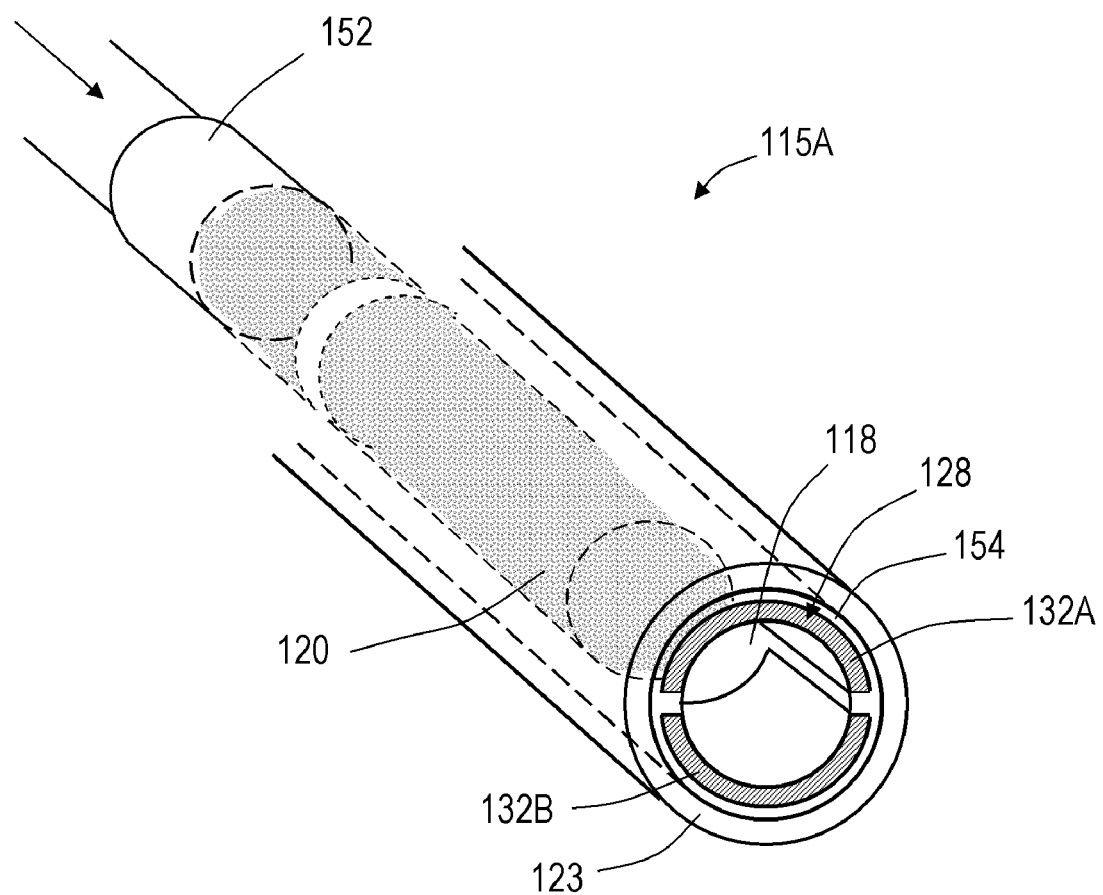
FIG. 2B is a schematic perspective view of a working end of the introducer of FIG. 2A.

Now referring to FIGS. 2A and 2B, the end of introducer 110A is shown schematically after being introduced into cancellous bone 122 with an inflow of fill material indicated at 120. The cancellous bone can be in any bone, for example in a vertebra. It can be seen that the introducer 110A and working end 115A comprise a sleeve or shaft that is preferably fabricated of a metal having a flow channel 118 extending therethrough from the proximal handle end 106 (see FIG. 1). In one embodiment, the introducer shaft is a stainless steel tube 123 having an outside diameter ranging between about 3.5 and 4.5 mm, but other dimensions are possible. As can be seen in FIGS. 2A and 3A, the flow channel 118 can terminate in a single distal opening or outlet 124a in the working end 115A, or there can be a plurality of flow outlets or ports 124b arranged angularly about the radially outward surface of the working end 115A, as shown in FIG. 3B. The outlets in the working end 115A thus allow for distal or radial ejection of fill material, or a working end can have a combination of radial and distal end outlets. As can be seen in FIG. 3C, the distal end of working end 115A also can provide an angled distal end outlet 124c for directing the flow of fill material from the outlet by rotating the working end 115A.

In FIGS. 2A and 2B, it can be seen that system 100 includes a remote energy source 125A and a controller 125B that are operatively coupled to an energy emitter 128 in the working end 115A of the introducer 110A for applying energy to the fill material 120 contemporaneous with and subsequent to ejection of the fill material 120 from the working end 115A. In one preferred embodiment, the energy source 125A is a radiofrequency (Rf) source known in the art that is connected to at least one electrode (132a and 132b in FIG. 2B) in contact with injected fill material 120, which preferably carries a radiosensitive composition therein. It is equally possible to use other remote energy sources and emitters 128 in the working end 115A which fall within the scope of the invention, such as (i) an electrical source coupled to a resistive heating element in the working end, (ii) a light energy source (coherent or broadband) coupled to an optical fiber or other light channel terminating in the working end; (iii) an ultrasound source coupled to an emitter in the working end; or a (iv) microwave source coupled to an antenna in the working end. In still another embodiment, the energy source 125A can be a magnetic source. The fill material 120 preferably includes an energy-absorbing material or an energy-transmitting material that cooperates with energy delivered from a selected energy source. For example, the energy-absorbing or energy-transmitting material can be a radiosensitive or conductive material for cooperating with an Rf source, chromophores for cooperating with a light source, ferromagnetic particles for cooperating with a magnetic source, and the like. In one embodiment, the fill material 120 can include a composition having an energy-absorbing property and an energy-transmitting property for cooperating with the remote energy source 125A. For example, the composition can absorb energy from the remote energy source 125A for polymerizing the composite or transmit energy for heating tissue adjacent to the composite.

As can be understood from FIGS. 2A and 2B, the exemplary introducer 110A is operatively coupleable to a source 145 of bone fill material 120 together with a pressure source or mechanism 150 that operates on the source of fill material 145 to deliver the fill material 120 through the introducer 110A into a bone (see arrows). The pressure source 150 can comprise any type of pump mechanism, such as a piston pump, screw pump or other hydraulic pump mechanism. In FIG. 2B, the pump mechanism is shown as a piston or plunger 152 that is slidable in the channel 118 of introducer 110A. In one embodiment, the pressure source 150 includes a controller 150B that controls the pressure applied by the pressure source 150. For example, where the pressure source 150 is a piston pump or screw pump that is motor driven, the controller 150B can adjust the motor speed to vary the pressure applied by the pressure source 150 to the inflow of the bone fill material 120. In one embodiment, the controller 150B also controls the volume of the bone fill material 120 that is introduced to a bone portion. In another embodiment, the controller 150B, or a separate controller, can also control the volume of bone fill material 120 introduced into the bone portion. For example, the controller 150B can operate a valve associated with the bone fill source 145 to selectively vary the valve opening, thus varying the volume of bone fill material 120 introduced to the bone portion.

As shown in FIGS. 2A and 2B, the introducer 110A preferably has an electrically and thermally insulative interior sleeve 154 that defines the interior flow channel 118. The sleeve can be any suitable polymer known in the art such as PEEK, Teflon™ or a polyimide. As can be seen in FIG. 2B, interior sleeve 154 carries conductive surfaces that function as energy emitter 128, and more particularly comprise spaced apart opposing polarity electrodes 132a and 132b. The electrodes 132a and 132b can have any spaced apart configuration and are disposed about the distal termination of channel 118 or about the surfaces of outlet 124a. The electrode configuration alternatively can include a first electrode in the interior of channel 118 and a second electrode on an exterior of introducer 110A. For example, the metallic sleeve 123 or a distal portion thereof can comprise one electrode. In a preferred embodiment, the electrodes 132a and 132b are connected to the Rf energy source 125A and controller 125B by an electrical cable 156 with (+) and (−) electrical leads 158a and 158b therein that extend through the insulative sleeve 154 to the opposing polarity electrodes. In one embodiment, the electrical cable 156 is detachably coupled to the handle end 106 of probe 105 by male-female plug (not shown). The electrodes 132a and 132b can be fabricated of any suitable materials known to those skilled in the art, such as stainless steels, nickel-titanium alloys and alloys of gold, silver platinum and the like.

In one embodiment, not shown, the working end 115A can also carry any suitable thermocouple or temperature sensor for providing data to controller 125B relating to the temperature of the fill material 120 during energy delivery. One or more thermocouples may be positioned at the distal tip of the introducer, or along an outer surface of the introducer and spaced from the distal end, in order to provide temperature readings at different locations within the bone. The thermocouple may also be slideable along the length of the introducer. In another embodiment, the working end can have at least one side port (not shown) in communication with a coolant source, the port configured to provide the coolant (e.g., saline) therethrough into the cancellous bone 122 to cool the cancellous bone in response to a temperature reading from the temperature sensor.

Figure 4:
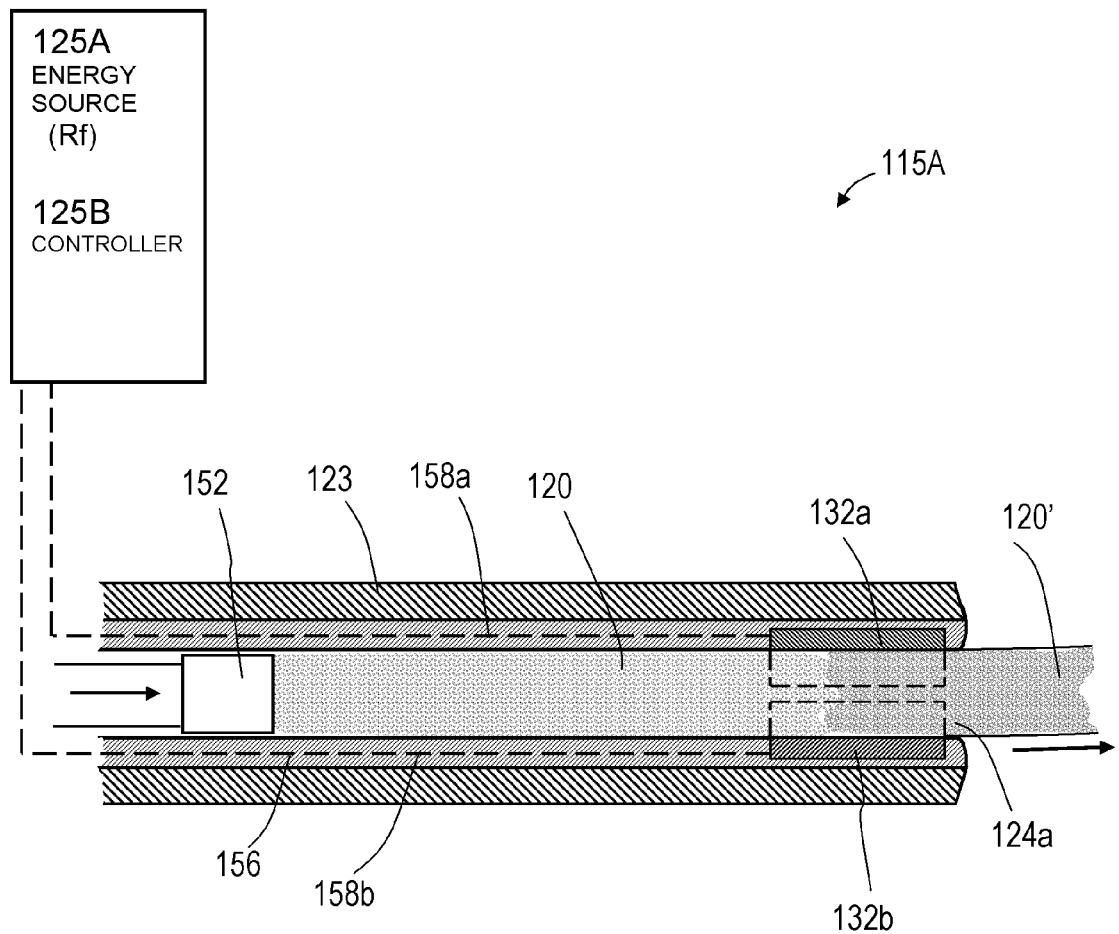
FIG. 4 is a schematic cross-sectional side view of one embodiment of a working end of a probe, in accordance with one embodiment.

Now turning to FIG. 4, the sectional view of working end 115A illustrates the application of energy to fill material 120 as it is being ejected from outlet 124a. The fill material 120 in the proximal portion of channel 118 is preferably a low viscosity flowable material such as a two-part curable polymer that has been mixed (e.g., PMMA) but without any polymerization having, for example, a viscosity of less than about 50,000 cps. Such a low viscosity fill material allows for simplified lower pressure injection through the introducer 110A. Further, the system allows the use of a low viscosity fill material 120 which can save great deal of time for the physician.

In a preferred embodiment, it is no longer necessary to wait for the bone cement to partly polymerize before injection. As depicted in FIG. 4, energy delivery at selected parameters from electrodes 132a and 132b to fill material 120 contemporaneous with its ejection from outlet 124a selectively alters a property of fill material indicated at 120'. In one embodiment, the altered flow property is viscosity. For example, the viscosity of the fill material 120' can be increased to a higher viscosity ranging from about 100,000 cps or more, 1,000,000 cps or more, to 2,000,000 cps or more. In another embodiment, the flow property is Young's modulus. For example, the Young's modulus of the fill material 120' can be altered to be between about 10 kPa and about 10 GPa. In still another embodiment, the flow property can be one of durometer, hardness and compliance.

Preferably, the fill material 120 carries a radiosensitive composition for cooperating with the Rf source 125A, as further described below. At a predetermined fill material flow rate and at selected Rf energy delivery parameters, the altered fill material 120' after ejection can comprise an increased viscosity material or an elastomer. At yet another predetermined fill material flow rate and at other Rf energy delivery parameters, the altered fill material 120' after ejection can comprise a substantially solid material. In the system embodiment utilized for vertebroplasty as depicted in FIGS. 2A and 5B, the controller 125B is adapted for delivering Rf energy contemporaneous with the selected flow rate of fill material 120 to provide a substantially high viscosity fill material 120' that is still capable of permeating cancellous bone. In other osteoplasty procedures such as treating necrosis of a bone, the system controller 125B can be adapted to provide much harder fill material 120' upon ejection from outlet 124a. Further, the system can be adapted to apply Rf energy to the fill material continuously, or in a pulse mode or in any selected intervals based on flow rate, presets, or in response to feedback from temperature sensors, impedance measurements or other suitable signals known to those skilled in the art.

In one embodiment, the controller 125B includes algorithms for adjusting power delivery applied by the energy source 125A. For example, in one embodiment the controller 125B includes algorithms for adjusting power delivery based on impedance measurements of the fill material 120' introduced to the bone portion. In another embodiment, the controller 125B includes algorithms for adjusting power delivery based on the volume of bone fill material 120 delivered to the bone portion. In still another embodiment, the controller 125B includes algorithms for adjusting power delivery based on the temperature of the bone fill material 120' introduced to the bone portion.

Figure 5A:
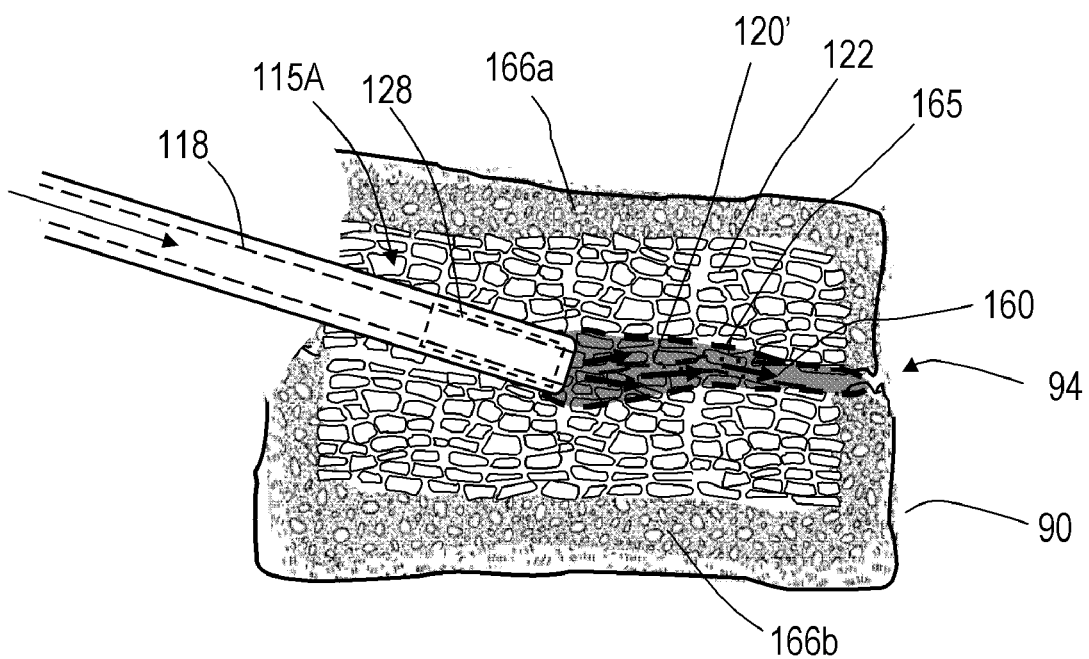
FIG. 5A is a schematic side view of an introducer inserted into a vertebral body and injecting flowable fill material into the vertebral body.
Figure 5B:
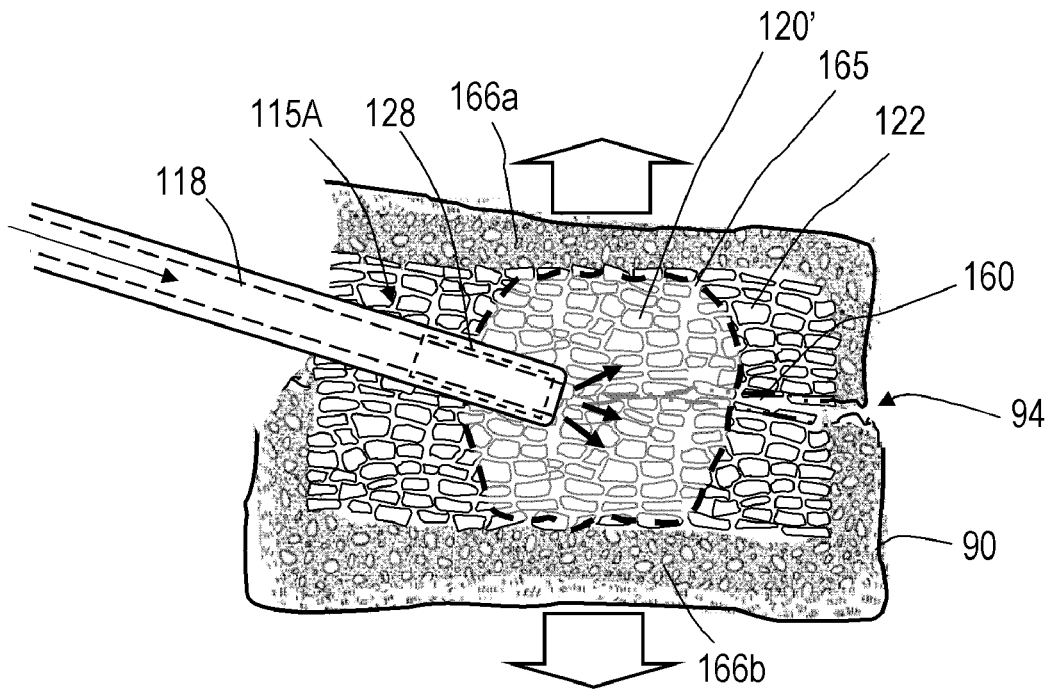
FIG. 5B is a schematic side view of the introducer in FIG. 5A injecting a relatively high viscosity volume of flowable fill material into the vertebral body, in accordance with one embodiment of the present invention.

FIGS. 5A and 5B are views of a vertebra 90 that are useful for explaining relevant aspects of one embodiment of the invention wherein working end 110A is advanced into the region of the fracture 94 in the cancellous bone 122. FIG. 5A indicates system 100 being used to inject flow material 120' into the vertebra with the flow material having a viscosity similar to conventional vertebroplasty or kyphoplasty, for example having the consistency of toothpaste. FIG. 5A depicts the situation wherein high pressure injection of a low viscosity material can simply follow paths of least resistance along a recent fracture plane 160 to migrate anteriorly in an uncontrolled manner. The migration of fill material could be any direction, including posteriorly toward the spinal canal or into the disc space depending on the nature of the fracture.

FIG. 5B illustrates system 100 including actuation of the Rf source 125A by the controller 125B to contemporaneously heat the fill material to eject altered fill material 120' with a selected higher viscosity into cancellous bone 122, such as the viscosities described above. With a selected higher viscosity, FIG. 5B depicts the ability of the system to prevent extravasation of fill material and to controllably permeate and interdigitate with cancellous bone 122, rather than displacing cancellous bone, with a plume 165 that engages cortical bone vertebral endplates 166a and 166b. The fill material broadly engages surfaces of the cortical endplates to distribute pressures over the endplates. In a preferred embodiment, the fill material controllably permeates cancellous bone 122 and is ejected at a viscosity adequate to interdigitate with the cancellous bone 122. Fill material with a viscosity in the range of between about 100,000 cps to 2,000,000 cps may be ejected, though even lower or higher viscosities may also be sufficient. The Rf source may selectively increase the viscosity of the fill material by about 10% or more as it is ejected from the introducer 115A. In other embodiments, the viscosity may be increased by about 20%, 50%, 100%, 500% or 1000% or more.

Still referring to FIG. 5B, it can be understood that continued inflows of high viscosity fill material 120' and the resultant expansion of plume 165 will apply forces on endplates 166a and 166b to at least partially restore the vertebral height of the vertebra 90. It should be appreciated that the working end 115A can be translated axially between about the anterior third of the vertebral body and the posterior third of the vertebral body during the injection of fill material 120', as well as that the working end 115A, which can be any of the types described above and shown in FIGS. 3A-3C, can be rotated.

Figure 6:
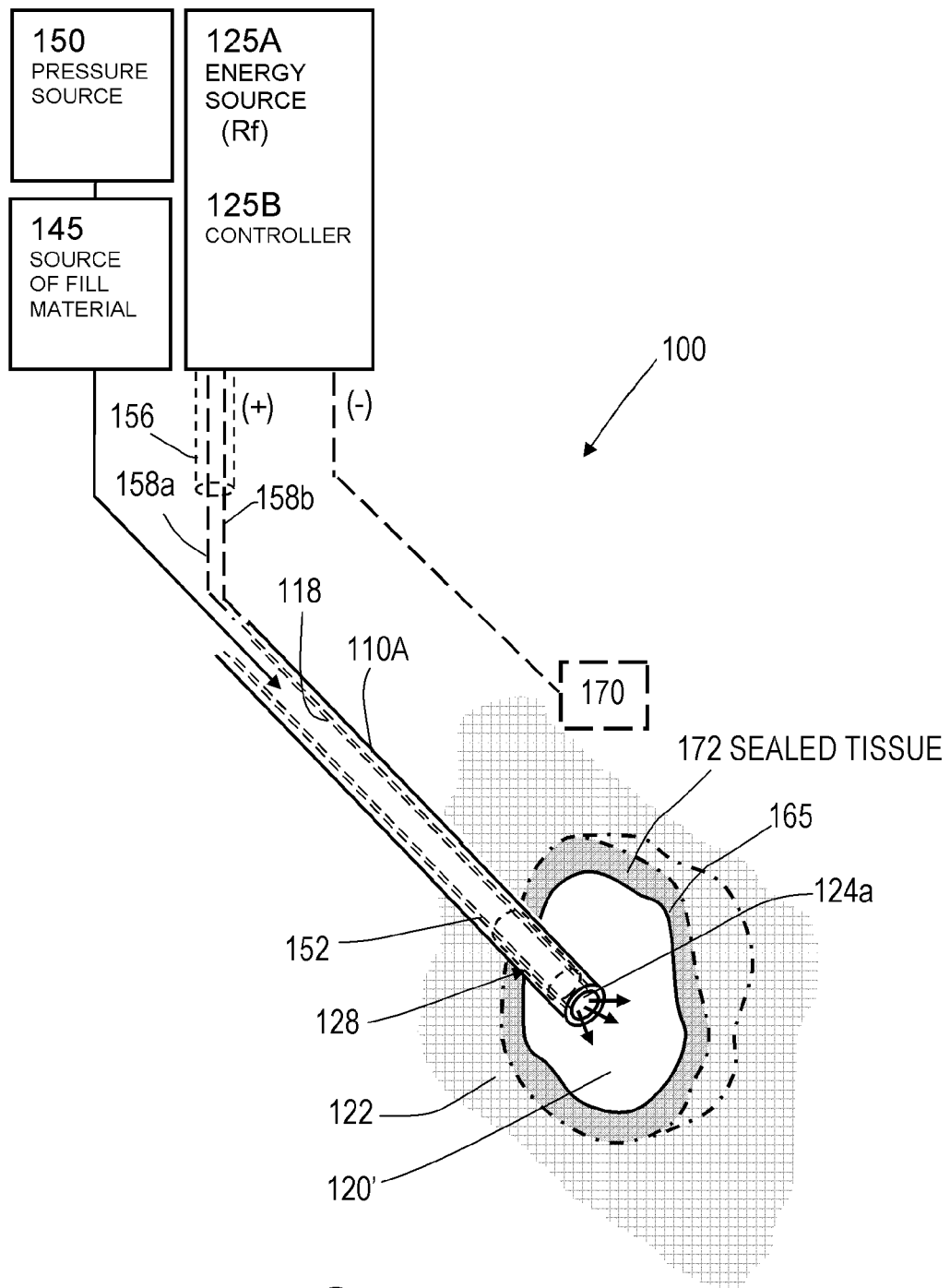
FIG. 6 is a schematic perspective view of a system for treating bone, in accordance with another embodiment.

FIG. 6 is a schematic view of an alternative embodiment of system 100 wherein the Rf source 125A and the controller 125B are configured to multiplex energy delivery to provide additional functionality. In one mode of operation, the system functions as described above and depicted in FIGS. 4 and 5B to alter flow properties of flowable fill material 120' as it is ejected from working end 115A. As can be seen in FIG. 6, the system further includes a return electrode or ground pad 170. Thus the system 100 can be operated in a second mode of operation wherein electrodes 132a and 132b (see FIG. 2B) are switched to a common polarity (or the distal portion of sleeve 123 can comprise such an electrode) to function in a mono-polar manner in conjunction with the ground pad 170. This second mode of operation advantageously creates high energy densities about the surface of plume 165 to thereby ohmically heat tissue at the interface of the plume 165 and the body structure.

In FIG. 6, the ohmically heated tissue is indicated at 172, wherein the tissue effect is coagulation of blood vessels, shrinkage of collagenous tissue and generally the sealing and ablation of bone marrow, vasculature and fat within the cancellous bone. The Rf energy levels can be set at a sufficiently high level to coagulate, seal or ablate tissue, with the controller delivering power based, for example, on impedance feedback which will vary with the surface area of plume 165. Of particular interest, the surface of plume 165 is used as an electrode with an expanding wavefront within cancellous bone 122. Thus, the vasculature within the vertebral body can be sealed by controlled ohmic heating at the same time that fill material 120' is permeating the cancellous bone. Within the vertebral body are the basivertebral (intravertebral) veins which are paired valveless veins connecting with numerous venous channels within the vertebra (pars spongiosa/red bone marrow). These basivertebral veins drain directly into the external vertebral venous plexus (EVVP) and the superior and inferior vena cava. The sealing of vasculature and the basivertebral veins is particularly important since bone cement and monomer embolism has been frequently observed in vertebroplasty and kyphoplasty cases (see "Anatomical and Pathological Considerations in Percutaneous Vertebroplasty and Kyphoplasty: A Reappraisal of the Vertebral Venous System", Groen, R. et al, Spine Vol. 29, No. 13, pp 1465-1471 2004). It can be thus understood that the method of using the system 100 creates and expands a "wavefront" of coagulum that expands as the plume 165 of fill material expands. The expandable coagulum layer 172, besides sealing the tissue from emboli, contains and distributes pressures of the volume of infill material 120' about the plume surface.

The method depicted in FIG. 6 provides an effective means for sealing tissue via ohmic (Joule) heating. It has been found that passive heat transfer from the exothermic reaction of a bone cement does not adequately heat tissue to the needed depth or temperature to seal intravertebral vasculature. In use, the mode of operation of the system 100 in a mono-polar manner for ohmically heating and sealing tissue can be performed in selected intervals alone or in combination with the bi-polar mode of operation for controlling the viscosity of the injected fill material.

In general, one aspect of the vertebroplasty or osteoplasty method in accordance with one of the embodiments disclosed herein allows for in-situ control of flows of a flowable fill material, and more particularly comprises introducing a working end of an introducer sleeve into cancellous bone, ejecting a volume of flowable fill material having a selected viscosity and contemporaneously applying energy (e.g., Rf energy) to the fill material from an external source to thereby increase the viscosity of at least portion of the volume to prevent fill extravasation. In a preferred embodiment, the system increases the viscosity by about 20% or more. In another preferred embodiment, the system increases the viscosity by about 50% or more.

In another aspect of one embodiment of a vertebroplasty method, the system 100 provides means for ohmically heating a body structure about the surface of the expanding plume 165 of fill material to effectively seal intravertebral vasculature to prevent emboli from entering the venous system. The method further provides an expandable layer of coagulum about the infill material to contain inflow pressures and distribute further expansion forces over the vertebral endplates. In a preferred embodiment, the coagulum expands together with at least a portion of the infill material to engage and apply forces to endplates of the vertebra.

Of particular interest, one embodiment of fill material 120 as used in the systems described herein (see FIGS. 2A, 4, 5A-5B and 6) is a composite comprising an in-situ hardenable or polymerizable cement component 174 and an electrically conductive filler component 175 in a sufficient volume to enable the composite to function as a dispersable electrode (FIG. 6). In one type of composite, the conductive filler component is any biocompatible conductive metal. In another type of composite, the conductive filler component is a form of carbon. The biocompatible metal can include at least one of titanium, tantalum, stainless steel, silver, gold, platinum, nickel, tin, nickel titanium alloy, palladium, magnesium, iron, molybdenum, tungsten, zirconium, zinc, cobalt or chromium and alloys thereof. The conductive filler component has the form of at least one of filaments, particles, microspheres, spheres, powders, grains, flakes, granules, crystals, rods, tubules, nanotubes, scaffolds and the like. In one embodiment, the conductive filler includes carbon nanotubes. Such conductive filler components can be at least one of rigid, non-rigid, solid, porous or hollow, with conductive filaments 176a illustrated in FIG. 7A and conductive particles 176b depicted in FIG. 7B.

Figure 7A:
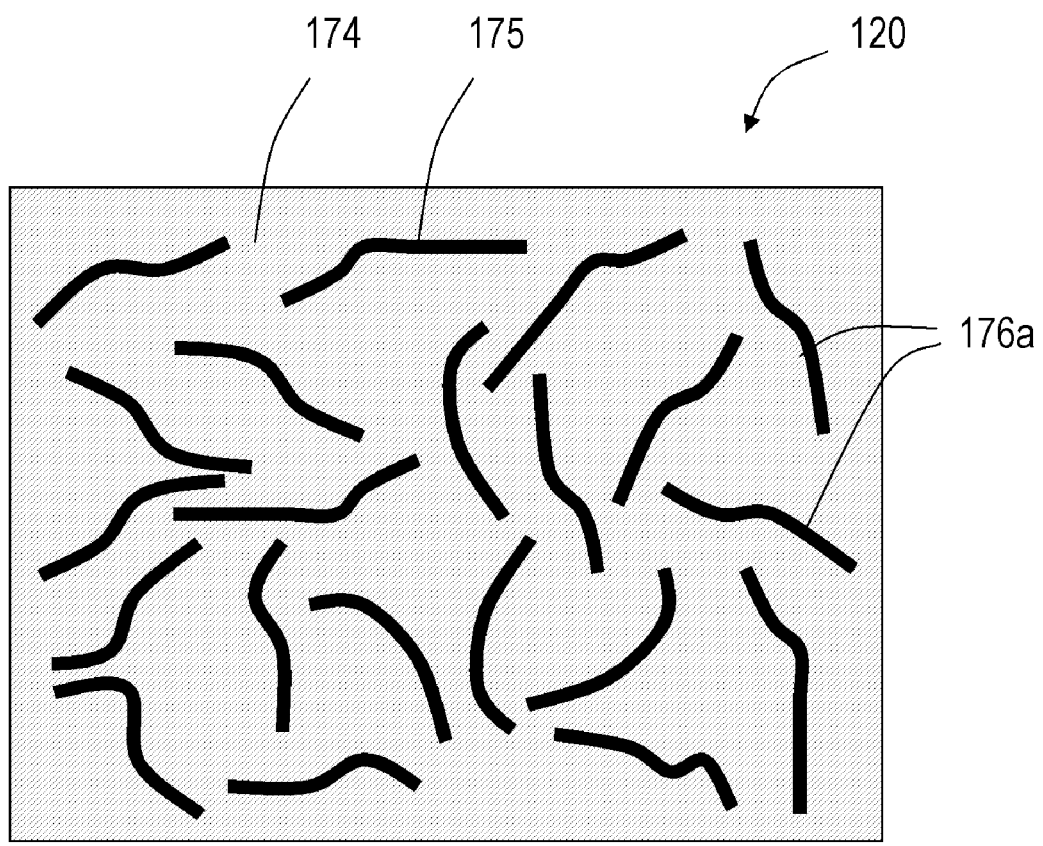
FIG. 7A is a schematic sectional view of a fill material, in accordance with one embodiment.
Figure 7B:
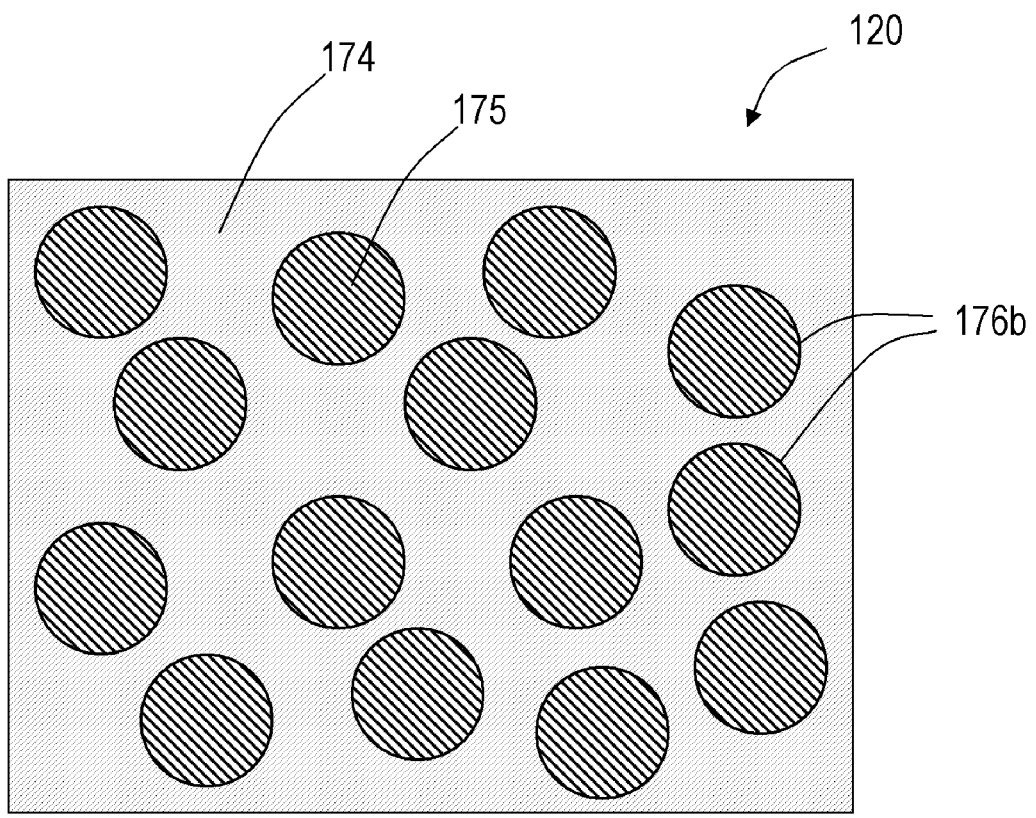
FIG. 7B is a schematic sectional view of a fill material, in accordance with another embodiment.

In a preferred embodiment, the conductive filler comprises chopped microfilaments or ribbons of a metal as in FIG. 7A that have a diameter or a cross-section dimension across a major axis ranging between about 0.0005" and 0.01". The lengths of the microfilaments or ribbons range from about 0.01" to 0.50". The microfilaments or ribbons are of stainless steel or titanium and are optionally coated with a thin gold layer or silver layer that can be deposited by electroless plating methods. Of particular interest, the fill material 120 of FIG. 7A has an in situ hardenable cement component 174 than has a first low viscosity and the addition of the elongated microfilament conductive filler component 175 causes the composite 120 to have a substantially high apparent viscosity due to the high surface area of the microfilaments and its interaction with the cement component 174. In one embodiment, the microfilaments are made of stainless steel, plated with gold, and have a diameter of about 12 microns and a length of about 6 mm. The other dimensions provided above and below may also be utilized for these microfilaments.

In another embodiment of bone fill material 120, the conductive filler component comprises elements that have a non-conductive core portion with a conductive cladding portion for providing electrosurgical functionality. The non-conductive core portions are selected from the group consisting of glass, ceramic or polymer materials. The cladding can be any suitable conductive metal as described above that can be deposited by electroless plating methods.

In any embodiment of bone fill material that uses particles, microspheres, spheres, powders, grains, flakes, granules, crystals or the like, such elements can have a mean dimension across a principal axis ranging from about 0.5 micron to 2000 microns. More preferably, the mean dimension across a principal axis range from about 50 microns to 1000 microns. It has been found that metal microspheres having a diameter of about 800 microns are useful for creating conductive bone cement that can function as an electrode.

In one embodiment, a conductive filler comprising elongated microfilaments wherein the fill material has from about 0.5% to 20% microfilaments by weight. More preferably, the filaments are from about 1% to 10% by weight of the fill material. In other embodiments wherein the conductive filler comprises particles or spheres, the conductive filler can comprise from about 5% of the total weight to about 80% of the weight of the material.

In an exemplary fill material 120, the hardenable component can be any in-situ hardenable composition such as at least one of PMMA, monocalcium phosphate, tricalcium phosphate, calcium carbonate, calcium sulphate or hydroxyapatite.

Figure 8A:
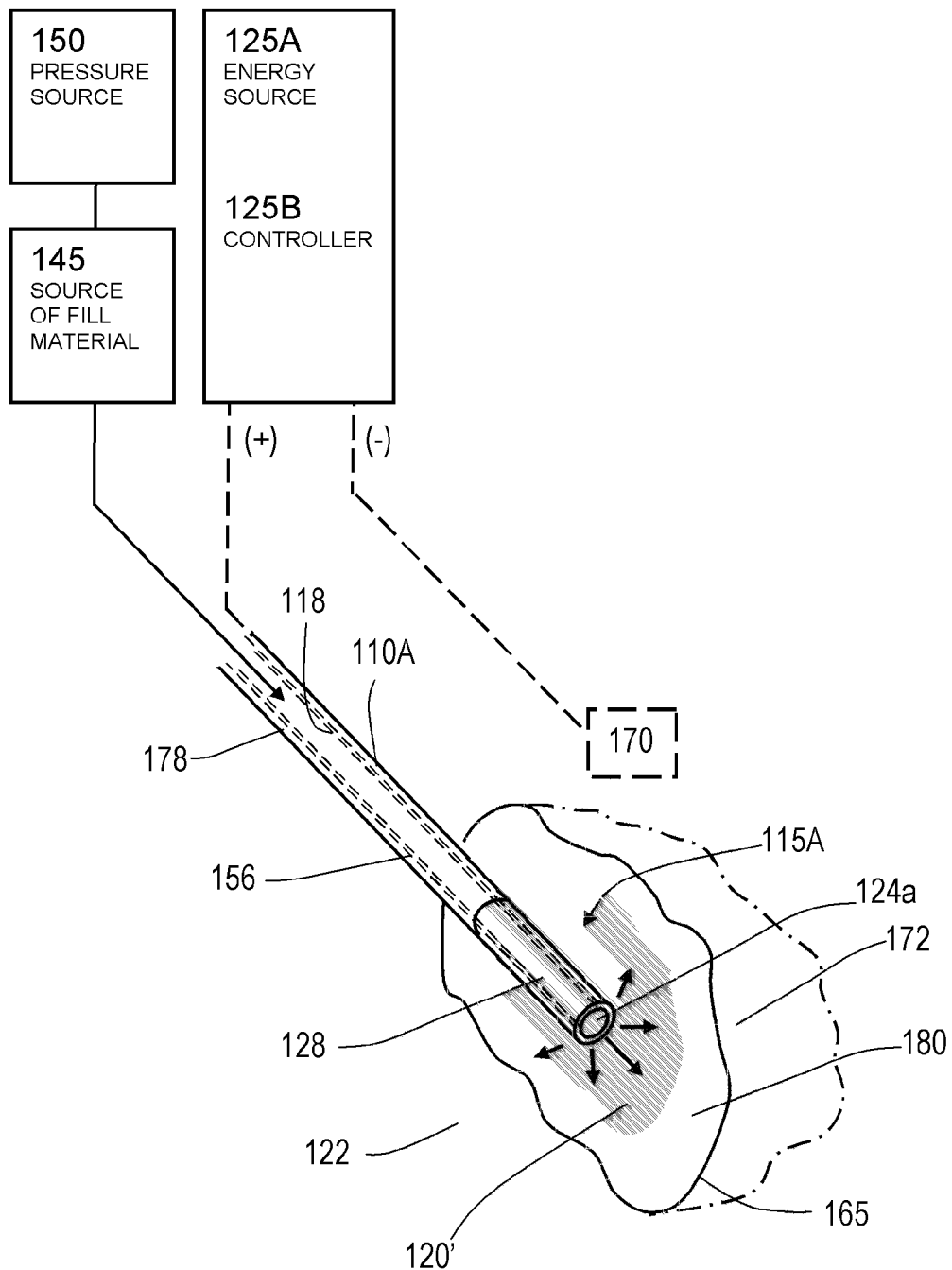
FIG. 8A is a schematic perspective view of a system for treating bone, in accordance with another embodiment.
Figure 8B:
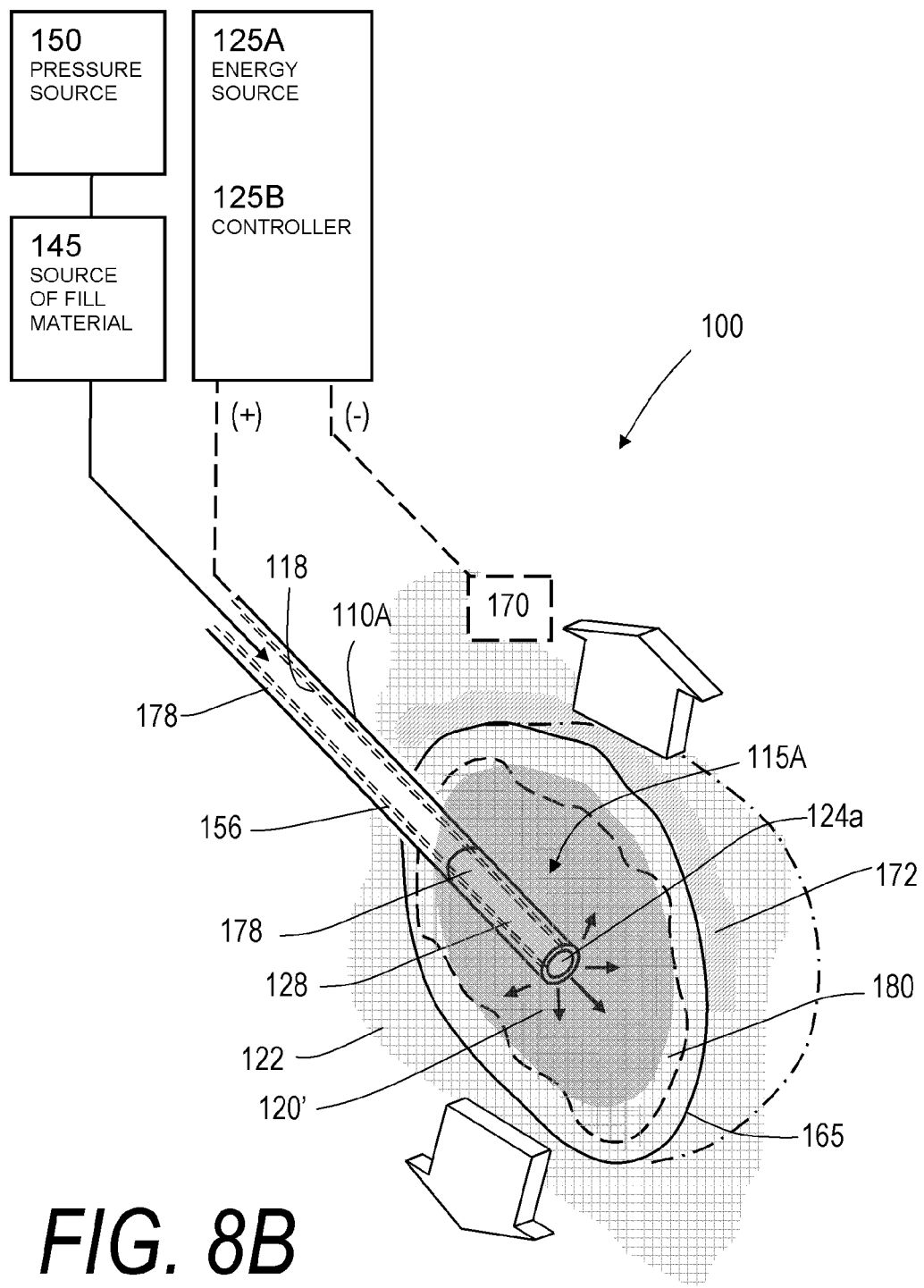
FIG. 8B is a schematic perspective view of the system in FIG. 8A, injecting an additional volume of fill material into a vertebral body.

Referring now to FIGS. 8A and 8B, an alternative method is shown wherein the system 100 and method are configured for creating asymmetries in properties of the infill material and thereby in the application of forces in a vertebroplasty. In FIG. 8A, the pressure mechanism 150 is actuated to cause injection of an initial volume or aliquot of fill material 120' that typically is altered in viscosity in working end 115A as described above—but the method encompasses flows of fill material having any suitable viscosity. The fill material 120' is depicted in FIGS. 8A and 8B as being delivered in a unilateral transpedicular approach, but any extrapedicular posterior approach is possible as well as any bilateral posterior approach. The system in FIGS. 8A-8B again illustrates a vertical plane through the fill material 120' that flows under pressure into cancellous bone 122 with expanding plume or periphery indicated at 165. The plume 165 has a three dimensional configuration as can be seen in FIG. 8B, wherein the pressurized flow may first tend to flow more horizontally that vertically. One embodiment of the method of the invention includes the physician translating the working end 115A of the introducer 110A slightly and/or rotating the working end 115A so that flow outlets 124a are provided in a selected radial orientation. In a preferred embodiment, the physician intermittently monitors the flows under fluoroscopic imaging as described above.

FIG. 8B depicts a contemporaneous or subsequent energy-delivery step of the method wherein the physician actuates the Rf electrical source 125A and controller 125B to cause Rf current delivery from the at least one electrode emitter 128 to cause ohmic (Joule) heating of tissue as well as internal heating of the inflowing fill material 120'. In this embodiment, the exterior surface of sleeve 123 is indicated as electrode or emitter 128 with the proximal portion of introducer 110A having an insulator coating 178. The Rf energy is preferably applied in an amount and for a duration that coagulates tissue as well as alters a flowability property of surface portions 180 of the initial volume of fill material proximate the highest energy densities in tissue.

In one preferred embodiment, the fill material 120 is particularly designed to create a gradient in the distribution of conductive filler with an increase in volume of material injected under high pressure into cancellous bone 122. This aspect of the method in turn can be used advantageously to create asymmetric internal heating of the fill volume. In this embodiment, the fill material 120 includes a conductive filler of elongated conductive microfilaments 176a (FIG. 7A). The filaments are from about 2% to 5% by weight of the fill material, with the filaments having a mean diameter or mean sectional dimension across a minor axis ranging between about 0.001" and 0.010" and a length ranging from about 1 mm to about 10 mm, more preferably about 1 mm to 5 mm. In another embodiment, the filaments have a mean diameter or a mean dimension across a minor axis ranging between about 1 micron and 500 microns, more preferably between about 1 micron and 50 microns, even more preferably between about 1 micron and 20 microns. It has been found that elongated conductive microfilaments 176a result in resistance to flows thereabout which causes such microfilaments to aggregate away from the most active media flows that are concentrated in the center of the vertebra proximate to outlet 124a. Thus, the conductive microfilaments 176a attain a higher concentration in the peripheral or surface portion 180 of the plume which in turn will result in greater internal heating of the fill portions having such higher concentrations of conductive filaments. The active flows also are controlled by rotation of introducer 110A to eject the material preferentially, for example laterally as depicted in FIGS. 8A and 8B rather that vertically. The handle 106 of the probe 105 preferably has markings to indicate the rotational orientation of the outlets 124b.

FIG. 8A depicts the application of Rf energy in a monopolar manner between electrode emitter 128 and ground pad 170, which thus causes asymmetric heating wherein surface portion 180 heating results in greater polymerization therein. As can be seen in FIG. 8A, the volume of fill material thus exhibits a gradient in a flowability property, for example with surface region 180 having a higher viscosity than inflowing material 120' as it is ejected from outlet 124a. In one embodiment, the gradient is continuous. Such heating at the plume periphery 165 can create an altered, highly viscous surface region 180. This step of the method can transform the fill material to have a gradient in flowability in an interval of about 5 seconds to 500 seconds with surface portion 180 being either a highly viscous, flowable layer or an elastomer that is expandable. In preferred embodiments, the interval of energy delivery required less than about 120 seconds to alter fill material to a selected asymmetric condition. In another aspect of the invention, the Rf energy application for creating the gradient in flowability also can be optimized for coagulating and sealing adjacent tissue.

The combination of the viscous surface portion 180 and the tissue coagulum 172 may function as an in-situ created stretchable, but substantially flow-impervious, layer to contain subsequent high pressure inflows of fill material. Thus, the next step of the method is depicted in FIG. 8B which includes injecting additional fill material 120' under high pressure into the interior of the initial volume of fill material 120 that then has a highly viscous, expandable surface. The viscous, expandable surface desirably surrounds cancellous bone so that the subsequent injection of fill material can expand the fill volume to apply retraction forces on the vertebra endplates 166a and 166b to provide vertical jacking forces, distracting cortical bone, for restoring vertebral height, as indicated by the arrows in FIG. 8B. The system can generate forces capable of breaking callus in cortical bone about a vertebral compression fracture when the fracture is less than completely healed.

In one embodiment, the method includes applying Rf energy to create highly viscous regions in a volume of fill material and thereafter injecting additional fill material 120 to controllably expand the fill volume and control the direction of force application. The scope of the method further includes applying Rf energy in multiple intervals or contemporaneous with a continuous flow of fill material. The scope of the method also includes applying Rf energy in conjunction with imaging means to prevent unwanted flows of the fill material. The scope of the invention also includes applying Rf energy to polymerize and accelerate hardening of the entire fill volume after the desired amount of fill material has been injected into a bone.

Figure 9A:
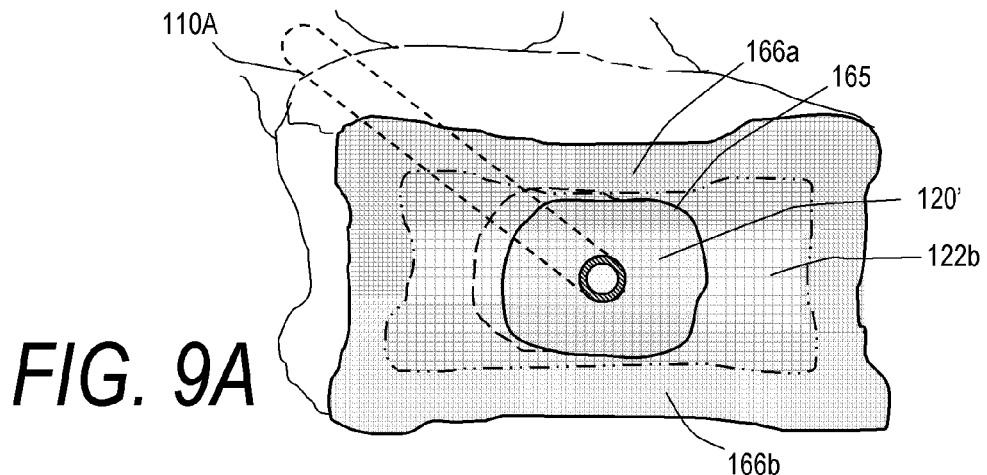
FIG. 9A is a schematic cross-sectional view of one step in a method for treating bone, in accordance with one embodiment.
Figure 9B:
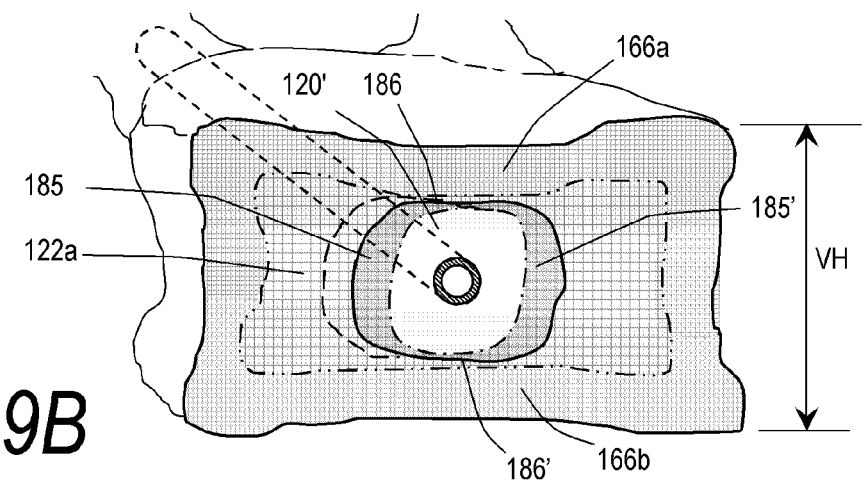
FIG. 9B is a schematic cross-sectional view of another step in a method for treating bone, in accordance with one embodiment.
Figure 9C:
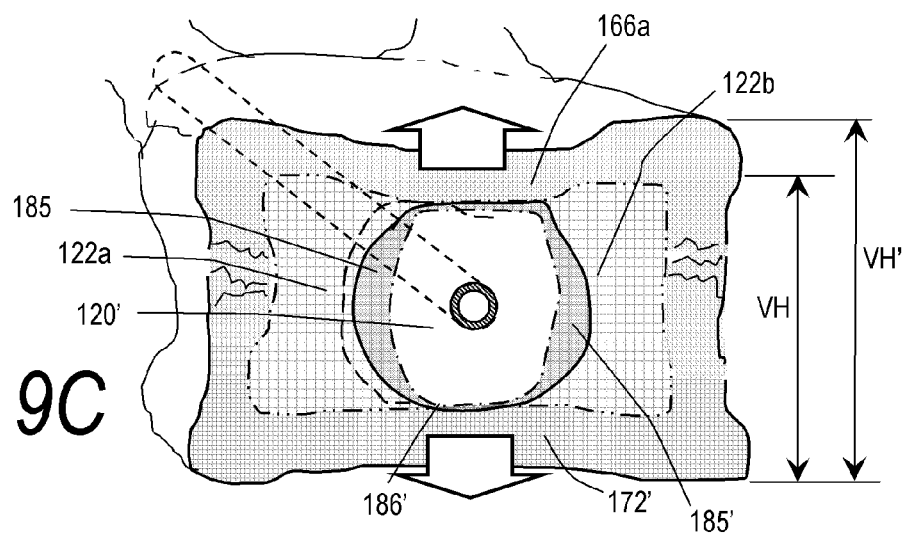
FIG. 9C is a schematic cross-sectional view of still another step in a method for treating bone, in accordance with one embodiment.

In another embodiment, the method includes creating Rf current densities in selected portions of the volume of fill material 120 to create asymmetric fill properties based on particular characteristics of the vertebral body. For example, the impedance variances in cancellous bone and cortical bone can be used to create varied Rf energy densities in fill material 120 to create asymmetric properties therein. Continued injection of fill material 120 are thus induced to apply asymmetric retraction forces against cortical endplates 166a and 166b, wherein the flow direction is toward movement or deformation of the lower viscosity portions and away from the higher viscosity portions. In FIGS. 9A-9C, it can be seen that in a vertebroplasty, the application of Rf energy in a mono-polar manner as in FIG. 6 naturally and preferentially creates more highly viscous, deeper "altered" properties in surfaces of the lateral peripheral fill volumes indicated at 185 and 185' and less viscous, thinner altered surfaces in the superior and inferior regions 186 and 186' of fill material 120. This effect occurs since Rf current density is localized about paths of least resistance which are predominantly in locations proximate to highly conductive cancellous bone 122a and 122b. The Rf current density is less in locations proximate to less conductive cortical bone indicated at 166a and 166b. Thus, it can be seen in FIG. 9B that the lateral peripheral portions 185 and 185' of the first flows of fill material 120 are more viscous and resistant to flow and expansion than the thinner superior and inferior regions. In FIG. 9C, the asymmetrical properties of the initial flows of fill material 120 allows the continued flows to apply retraction forces in substantially vertical directions to reduce the vertebral fracture and increase vertebral height, for example from VH (FIG. 9B) to VH' in FIG. 9C.

Figure 10A:
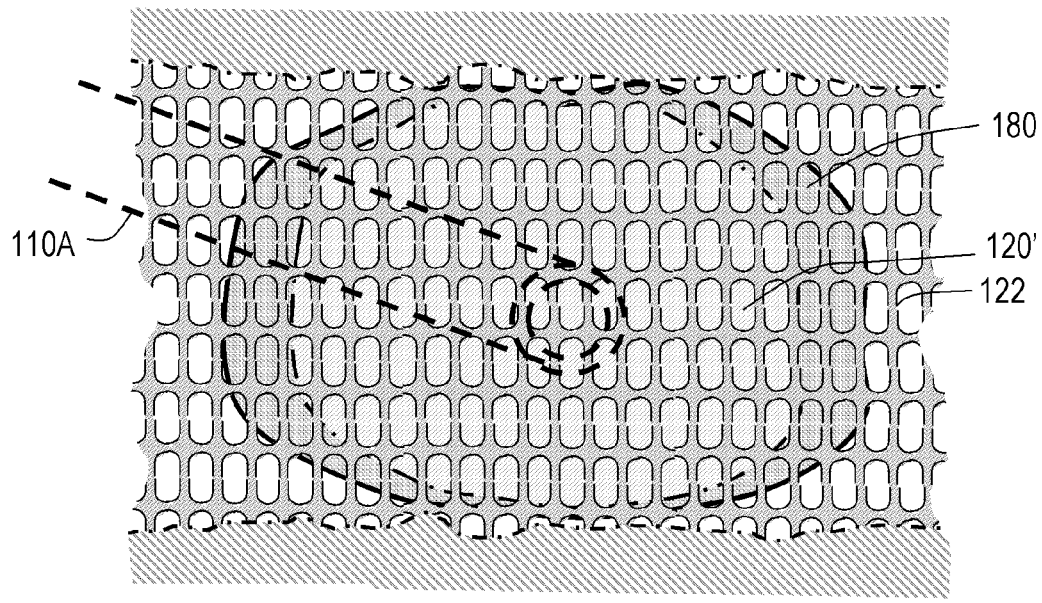
FIG. 10A is a schematic cross-sectional view of a step in a method for treating bone, in accordance with another embodiment.
Figure 10B:
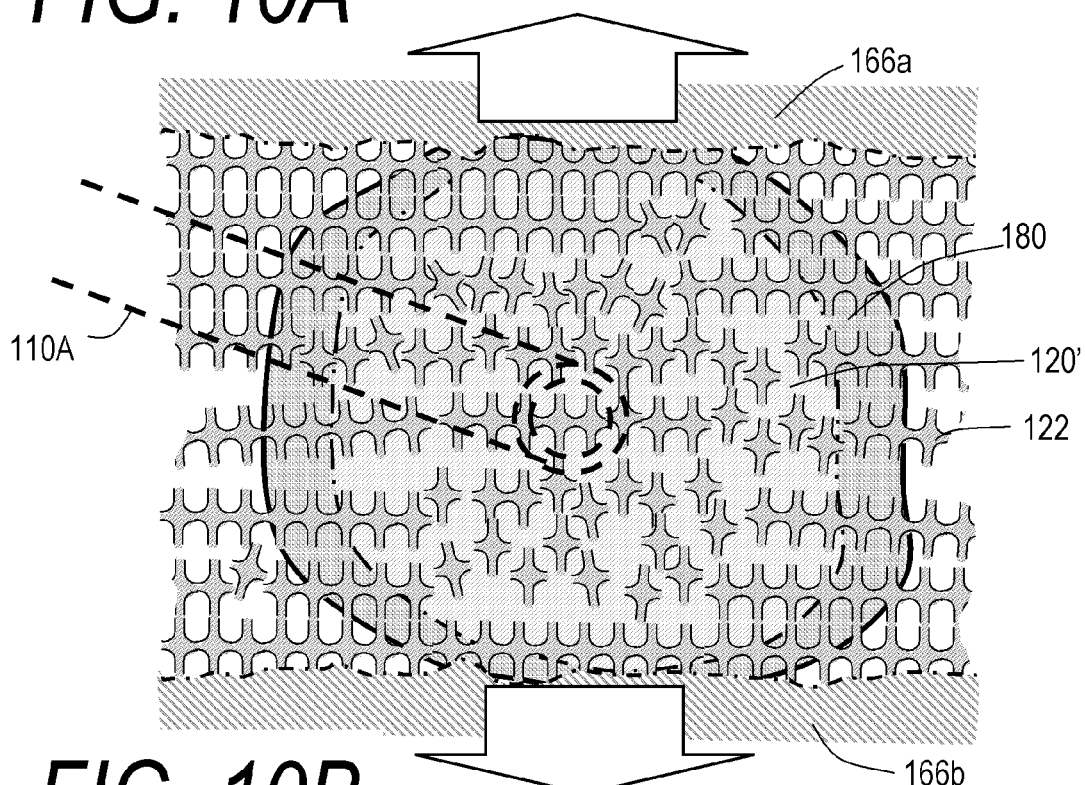
FIG. 10B is a schematic cross-sectional view of another step in a method for treating bone, in accordance with another embodiment.

FIGS. 10A and 10B are schematic views that further depict a method corresponding to FIGS. 9B and 9C that comprises expanding cancellous bone for applying retraction forces against cortical bone, e.g., endplates of a vertebra in a vertebroplasty. As can be seen in FIG. 10A, an initial volume of flowable fill material 120 is injected into cancellous bone wherein surface region 180 is altered as described above to be highly viscous or to comprise and elastomer that is substantially impermeable to interior flows but still be expandable. The surface region 180 surrounds subsequent flows of fill material 120' which interdigitate with cancellous bone. Thereafter, as shown in FIG. 10B, continued high pressure inflow into the interior of the fill material thereby expands the cancellous bone 122 together with the interdigitated fill material 120'. As can be seen in FIG. 10B, the expansion of cancellous bone 122 and fill material 120' thus applies retraction forces to move cortical bone endplates 166a and 166b. The method of expanding cancellous bone can be used to reduce a bone fracture such as a vertebral compression fracture and can augment or restore the height of a fractured vertebra. The system thus can be used to support retract and support cortical bone, and cancellous bone. The method can also restore the shape of an abnormal vertebra, such as one damaged by a tumor.

After utilizing system 100 to introduce, alter and optionally harden fill material 120 as depicted in FIGS. 9A-9C and 10A-10B, the introducer 110A can be withdrawn from the bone. Alternatively, the introducer 110A can have a release or detachment structure indicated at 190 for de-mating the working end from the proximal introducer portion as described in co-pending U.S. patent application Ser. No. 11/130,843, filed May 16, 2005, now U.S. Pub. No. 2006-0100706, the entirety of which is hereby incorporated by reference and should be considered a part of this specification.

Figure 11A:
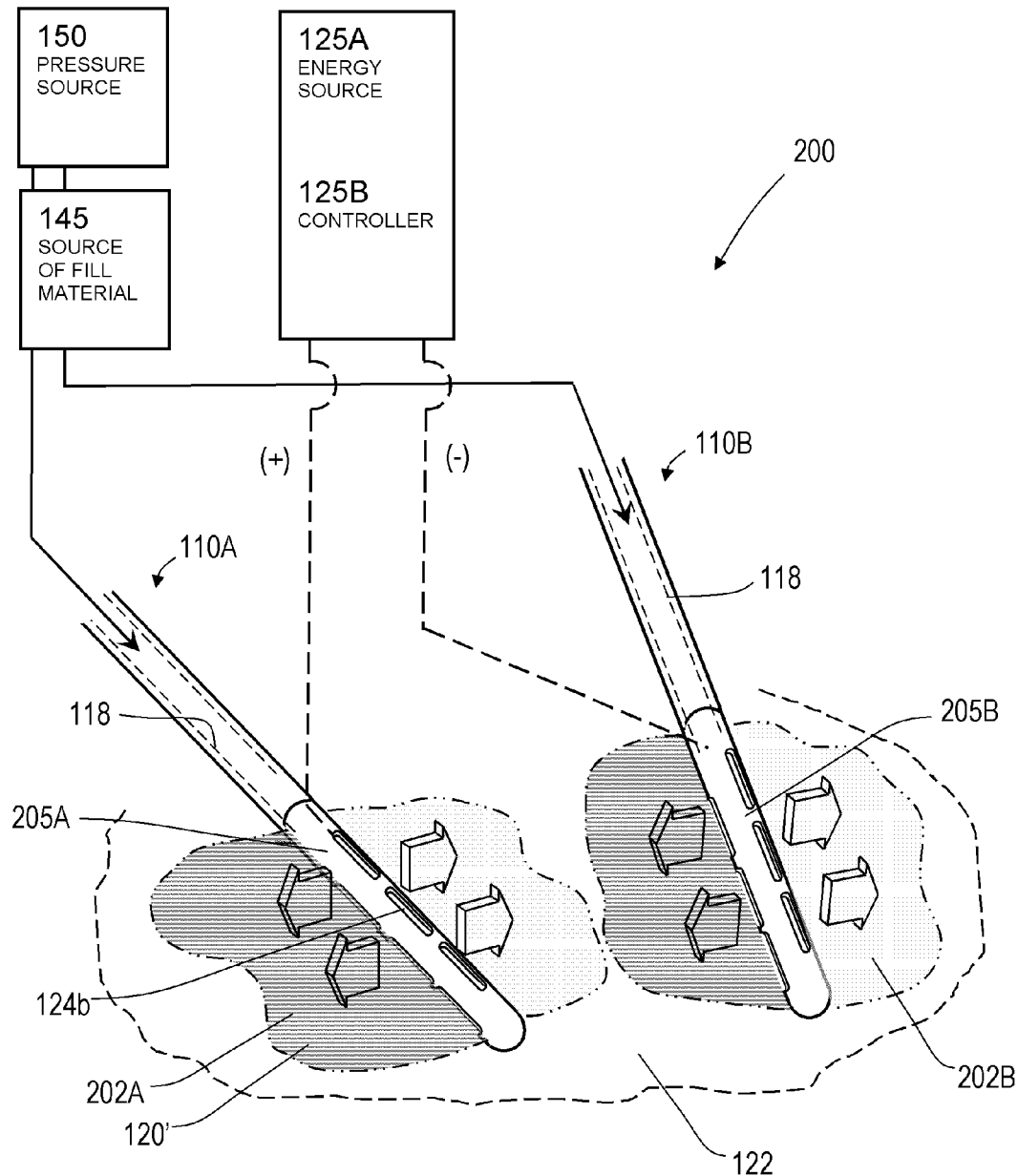
FIG. 11A is a schematic perspective view of a system for treating bone, in accordance with another embodiment.
Figure 11B:
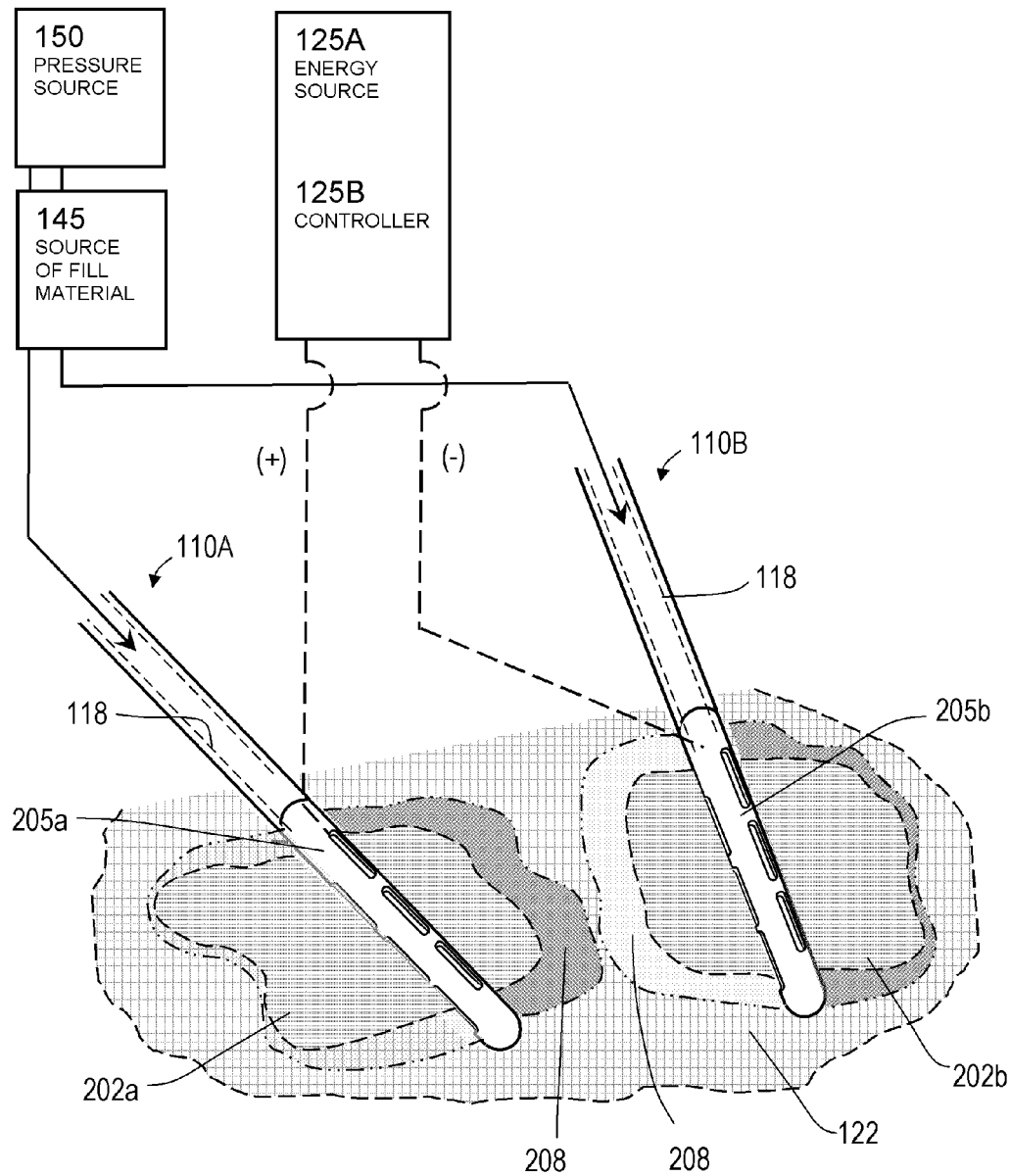
FIG. 11B is a schematic perspective view of the system in FIG. 11A, applying energy to a fill material.

Another system 200 for controlling flow directions and for creating asymmetric properties is shown in FIGS. 11A and 11B, wherein first and second introducers 110A and 110B similar to those described above are used to introduce first and second independent volumes 202a and 202b of fill material 120 in a bilateral approach. In this embodiment, the two fill volumes function as opposing polarity electrodes in contact with electrodes 205a and 205b of the working ends. Current flow between the electrodes thus operates in a bi-polar manner with the positive and negative polarities indicated by the (+) and (−) symbols. In this method, it also can be seen that the highest current density occurs in the three dimensional surfaces of volumes 202a and 202b that face one another. This results in creating the thickest, high viscosity surfaces 208 in the medial, anterior and posterior regions and the least "altered" surfaces in the laterally outward regions. This method is well suited for preventing posterior and anterior flows and directing retraction forces superiorly and inferiorly since lateral flow are contained by the cortical bone at lateral aspects of the vertebra. The system can further be adapted to switch ohmic heating effects between the bi-polar manner and the mono-polar manner described previously.

Figure 12:
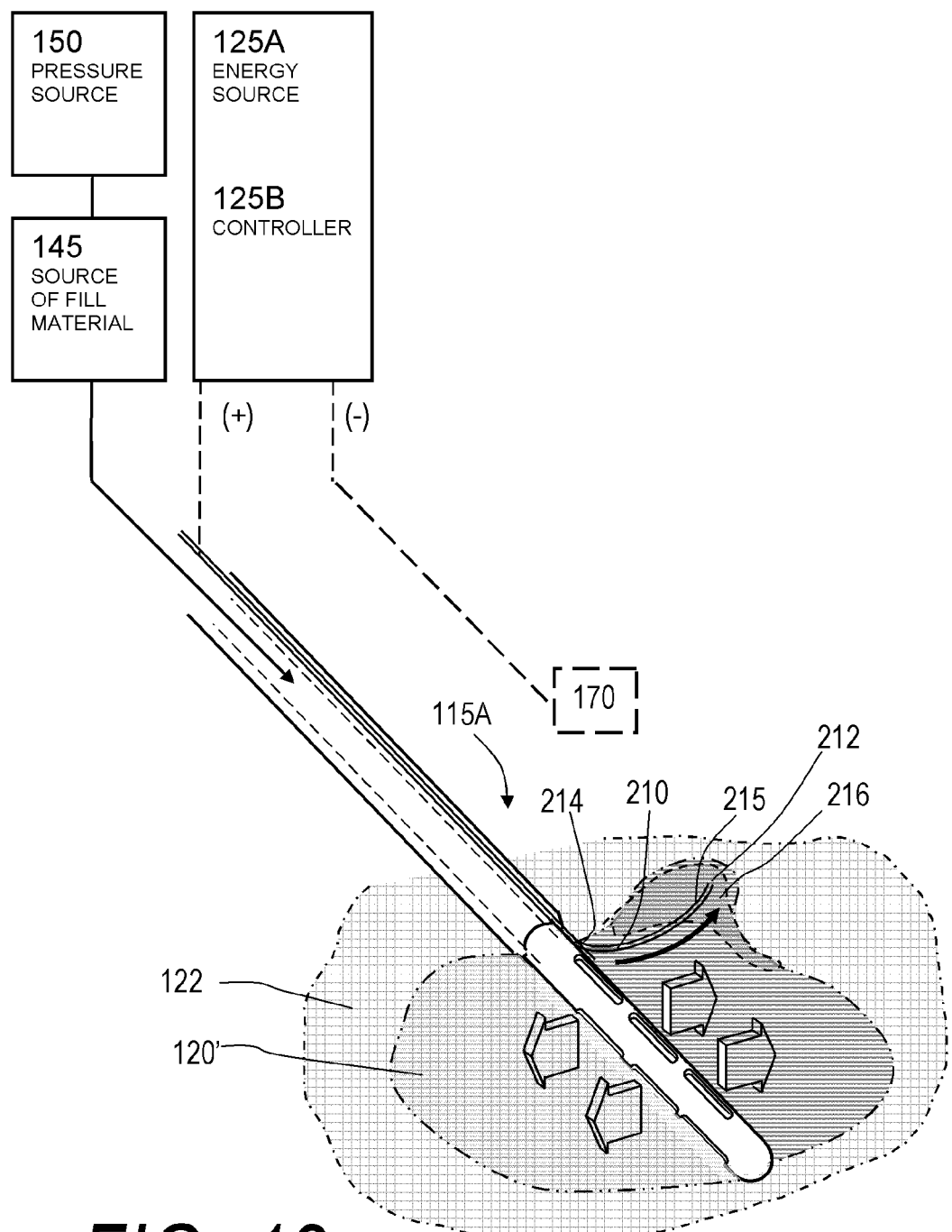
FIG. 12 is a schematic perspective view of a system for treating bone, in accordance with another embodiment.

Now referring to FIG. 12, another embodiment is shown wherein a translatable member 210 that functions as an electrode is carried by introducer 110A. In a preferred embodiment, the member 210 is a superelastic nickel titanium shape memory wire that has a curved memory shape. The member 210 can have a bare electrode tip 212 with a radiopaque marking and is otherwise covered by a thin insulator coating. In FIG. 12, it can be seen that the introducer can be rotated and the member can be advanced from a port 214 in the working end 115A under imaging. By moving the electrode tip 212 to a desired location and then actuating RF current, it is possible to create a local viscous or hardened region 216 of fill material 120. For example, if imaging indicates that fill material 120 is flowing in an undesired direction, then injection can be stopped and Rf energy can be applied to harden the selected location.

Figure 13:
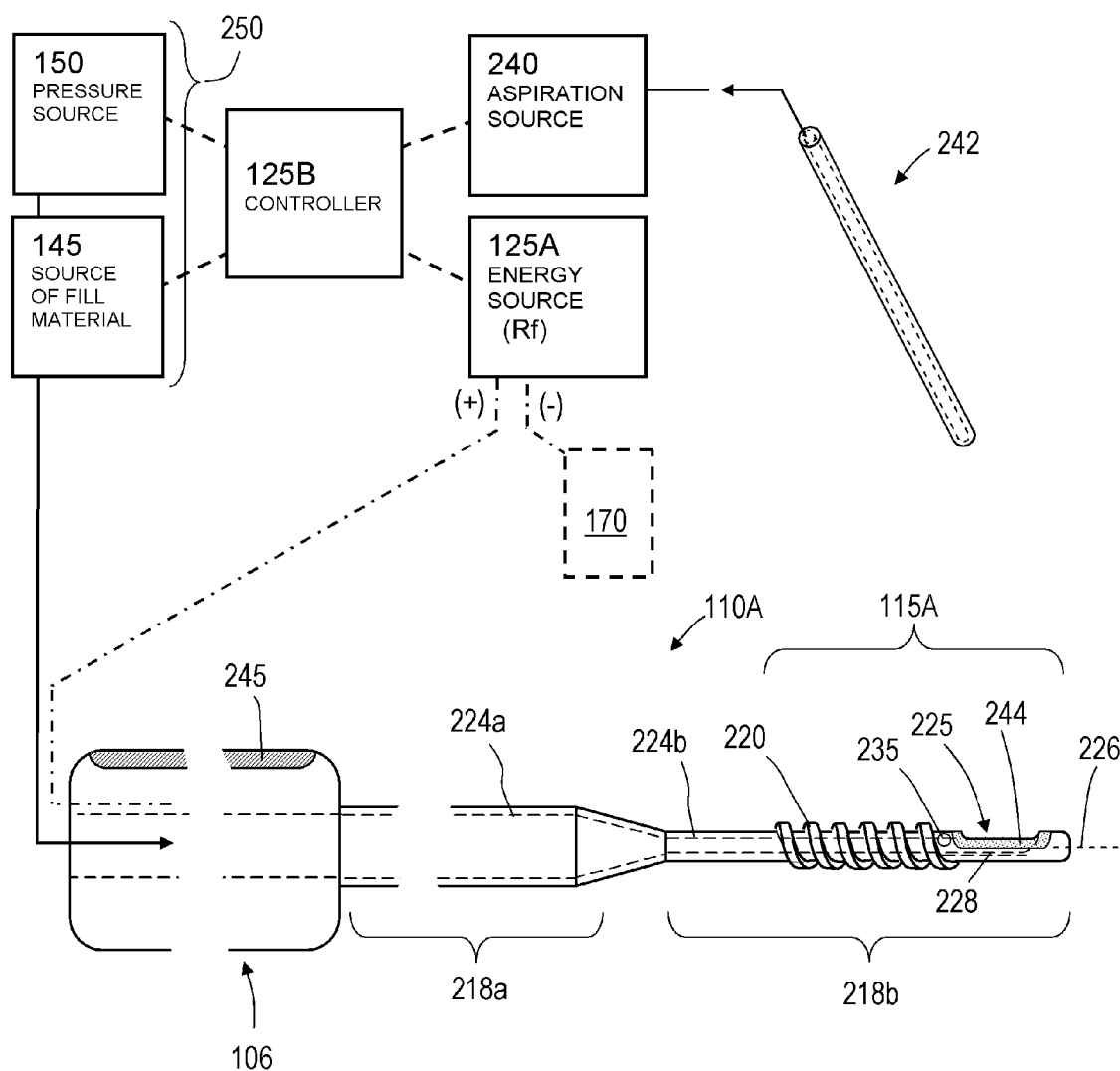
FIG. 13 is a schematic view of another embodiment of a bone cement delivery system together with an aspiration source.

FIG. 13 illustrates another embodiment of the introducer 110A which includes a transition in cross-sectional dimension to allow for decreased pressure requirements for introducing bone cement through the length of the introducer 110A. In the embodiment of FIG. 13, the proximal handle end 106 is coupled to introducer 110A that has a larger diameter proximal end portion 218a that transitions to a smaller diameter distal end portion 218b configured for insertion into a vertebral body. The distal end portion 218b includes exterior threads 220 for helical advancement and engagement in bone to prevent the introducer 110A from moving proximally when cement is injected into a vertebral body or other bone, for example to augment vertebral height when treating a VCF. The bore that extends through the introducer 110A similarly transitions from larger diameter bore portion 224a to smaller diameter bore portion 224b. The embodiment of FIG. 13 utilizes a bore termination or slot 225 in a sidewall of the working end 115A for ejecting bone cement at a selected radial angle from the axis 226 of the introducer for directing cement outflows within a vertebral body.

Still referring to FIG. 13, the introducer 110A is coupled to bone cement source 145 and pressure source 150 as described previously that is controlled by controller 125B. Further, an energy source 125A (e.g., Rf source) is coupled to an energy delivery mechanism in the working end 115A for applying energy to a cement flow within bore 224b. In the embodiment of FIG. 13, the introducer 110A can be fabricated of a strong reinforced plastic such a polymide composite with a sleeve electrode 228 in bore 224b and inward of the bore termination slot 225, similar to electrode 128 depicted in FIG. 3A. The electrode 228 in FIG. 13 is coupled to Rf source 125A for operating in a mono-polar manner in cooperation with the return ground pad 170. The controller 125B again is operatively connected to the Rf source 125A to adjust energy delivery parameters in response to feedback from a thermocouple 235 in the bore 124b or in response to measuring impedance of the cement flow. In FIG. 13, the controller 125B further is operationally connected to an aspiration source 240 that is coupled to a needle-like introducer sleeve 242 that can be inserted into a bone to apply suction forces to the interior of vertebra for relieving pressure in the vertebra and/or extracting fluids, bone marrow and the like that could migrate into the venous system. The use of such an aspiration system will be described further below.

In FIG. 13, the introducer 110A has a larger diameter bore 224a that ranges from about 4 mm to 10 mm, and preferably is in the range of about 5 mm to 6 mm. The smaller diameter bore 224b can range from about 1 mm to 3 mm, and preferably is in the range of about 1.5 mm to 2.5 mm. The exterior threads 220 can be any suitable height with single or dual flights configured for gripping cancellous bone. The thread height and length of the reduced diameter section 218b are configured for insertion into a vertebra so that the port 225 can be anteriorly or centrally located in the vertebral body. The working end 115A further carries a radiopaque marking 244 for orienting the radial angle of the introducer and bore termination port 225. In FIG. 13, the radiopaque marking 244 is elongated and surrounds port 225 in the introducer sidewall. The handle 106 also carries a marking 245 for indicating the radial angle of port 225 to allow the physician to orient the port by observation of the handle.

Figure 14A:
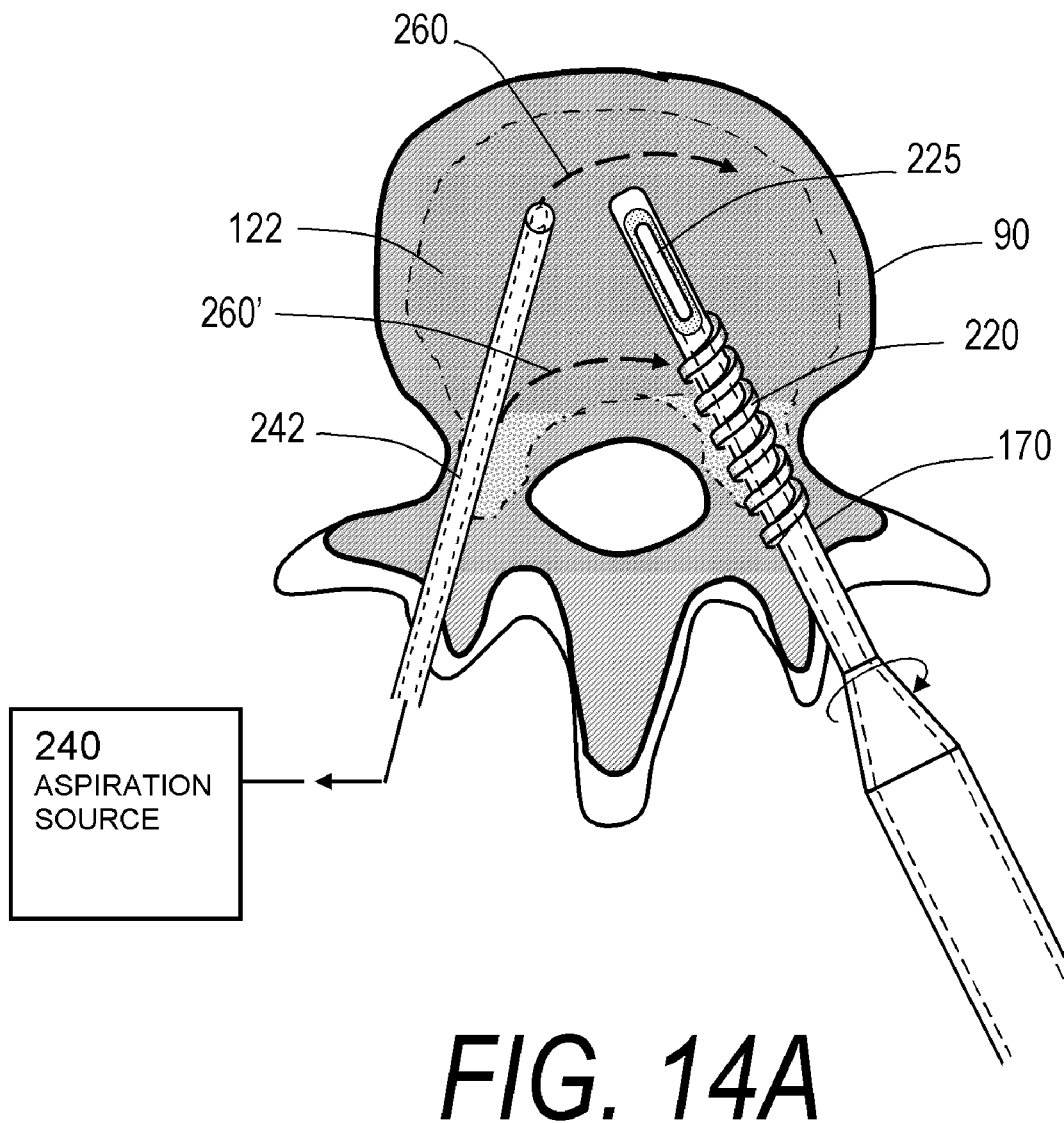
FIG. 14A is a sectional view of a working end of an introducer as in FIG. 13 showing the orientation of a cement injection port in a vertebra.
Figure 14B:
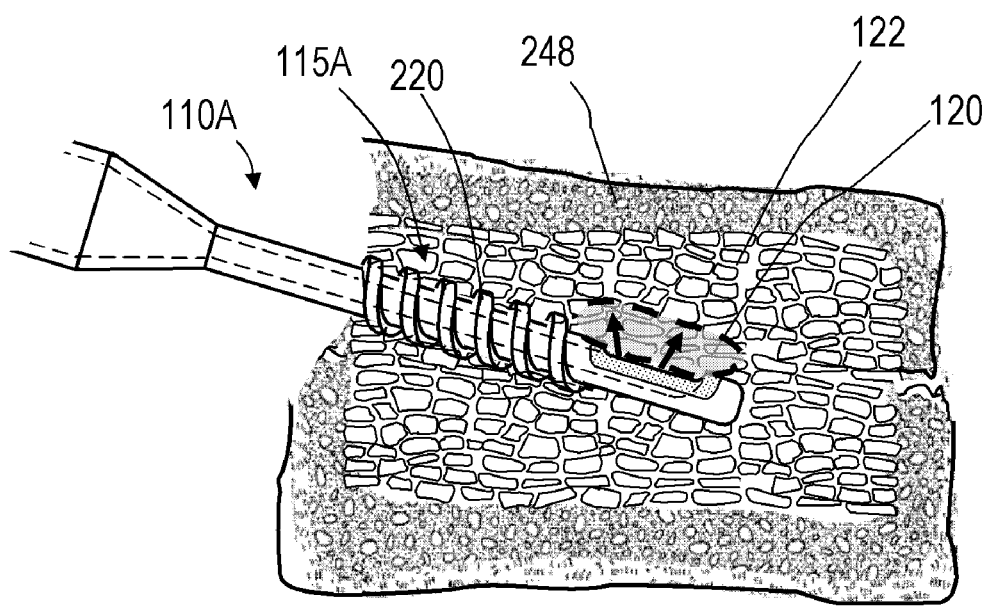
FIG. 14B is a sectional view of the working end of FIG. 14A showing an initial inflow of bone cement.
Figure 14C:
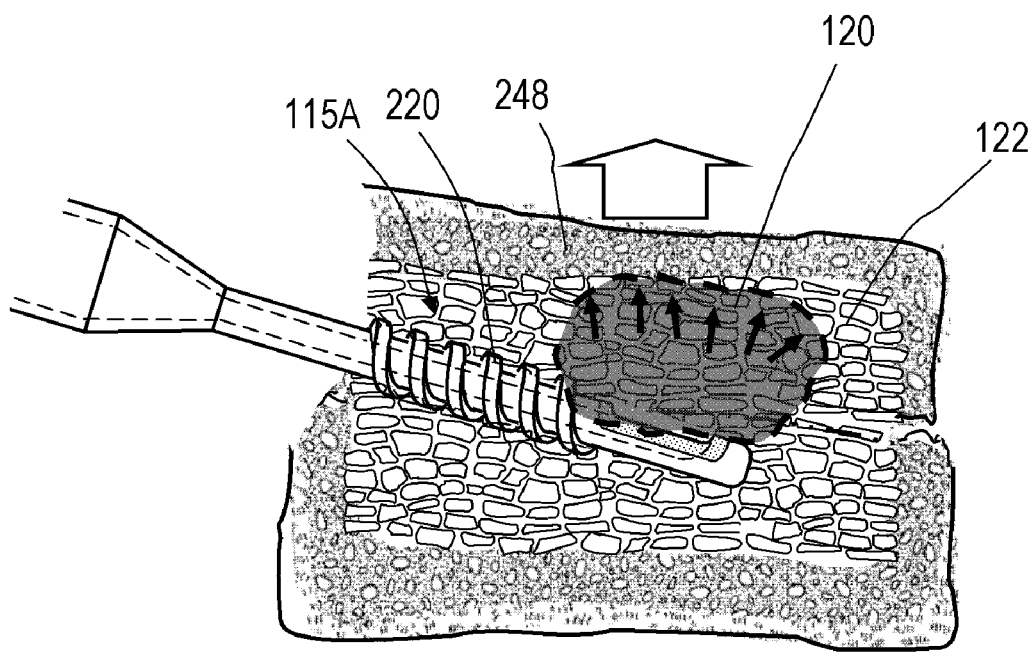
FIG. 14C is a sectional view of the working end of FIG. 14B showing an additional inflow of bone cement to reduces a vertebral fracture.

Now referring to FIGS. 14A-14C, the working end 115A of the introducer of FIG. 13 is shown after being introduced into cancellous bone 122 in vertebra 90. FIG. 14A illustrates a horizontal sectional view of vertebra 90 wherein the bore termination port 225 is oriented superiorly to direct cement inflows to apply forces against cancellous bone 122 and the superior cortical endplate 248 of the vertebra. A method of delivering bone cement comprises providing a flow source 250 (the pressure source 150 and cement source 145, in combination, are identified as flow source 250 in FIG. 13) for bone cement inflows and a controller 125B for control of the bone cement inflows, and inflowing the bone cement into a vertebral body wherein the controller 125B adjusts an inflow parameter in response to a measured characteristic of the cement. In one embodiment, the measured characteristic is temperature of the bone cement measured by thermocouple 235 in the working end 115A. The controller 125B can be any custom computerized controller. In one embodiment, the system can utilize a commercially available controller manufactured by EFD Inc., East Providence, RI 02914, USA for flow control, wherein either a positive displacement dispensing system or an air-powered dispensing system can be coupled to the flow source 250. In response to feedback from thermocouple 235 that is received by the controller 125B, any inflow parameter of the bone cement flow can be adjusted, for example cement injection pressure, the inflow rate or velocity of the bone cement flows or the acceleration of a bone cement flow. The controller 125B also can preferably vary any inflow parameter with time, for example, in pulsing cement inflows to thereby reduce a vertebral fracture, or move cancellous or cortical bone (see FIGS. 14A-14B). The cement 120 can be introduced in suitable volumes and geometries to treat fractures or to prophylactically treat a vertebra.

In another method corresponding to the invention, the flow source 250, controller 125B and Rf energy source 125A are provided as shown in FIG. 13. The controller 125B again is capable of adjusting any bone cement delivery parameter in response to impedance and/or temperature. The controller 125B adjusts at least one cement delivery parameter selected from cement volume, pressure, velocity and acceleration of the inflowing cement. The controller 125B also can vary pressure of the inflowing cement or pulse the cement inflows. In this embodiment, the controller 125B also is capable of adjusting energy delivered from Rf energy source 125A to the inflowing cement 120 in response to impedance, temperature, cement viscosity feedback or cement flow parameters to alter cement viscosity as described above. Cement viscosity can be calculated by the controller 125B from temperature and pressure signals. The controller 125B also is capable of being programmed with algorithms to ramp-up and ramp down power in one or more steps, or can be programmed to pulse power delivery to the bone cement 120 (FIGS. 14A-14BA).

As can be seen in FIGS. 14B and 14C, the inflowing cement 120 can be directed to apply forces against cancellous bone 122 and the superior cortical endplate 248 of the vertebra, or the working end can be rotated to introduce cement 120 and apply forces in other directions. In this embodiment, the extension of the working end 115A in cancellous bone serves as a support for causing expansion pressures to be directed substantially in the direction of cement flows. The method of treating the vertebra includes translating (by helical advancement) and rotating the introducer 110A to thereby alter the direction of cement introduction. In another embodiment (not shown), the introducer 110A can comprise an assembly of first and second concentric sleeves wherein the outer sleeve has threads 220 for locking the assembly in bone and the inner sleeve is rotatable to adjust the angular direction of port 225 wherein the sleeves are locked together axially. This embodiment can be used to intermittently angularly adjust the direction of cement outflows while helical movement of the outer sleeve adjusts the axial location of port 225 and the cement outflows.

In another method of the invention, referring back to FIG. 14A, the aspiration introducer sleeve 242 can be inserted into the vertebral body 90, for example through the opposing pedicle. The controller 125B can be programmed to alter aspiration parameters in coordination with any bone cement inflow parameter. For example, the cement inflows can be pulsed and the aspiration forces can be pulsed cooperatively to extract fluids and potentially embolic materials, with the pulses synchronized. In one method, the cement inflows are pulsed at frequency ranging between about 1 per second and 500 per second with an intense, high acceleration pulse which causes bone marrow, fat, blood and similar materials to become susceptible to movement while at the same time the aspiration pulses are strong to extract some mobile marrow etc into the aspiration sleeve 242. In FIG. 14A, the aspiration sleeve 242 is shown with single port in it distal end. It should be appreciated that an aspiration sleeve 242 that has a plurality of inflow ports along the length of the sleeve, a sleeve that is curved or can be of a shape memory alloy (e.g., Nitinol) for introduction in a curved path in the anterior of posterior region of a vertebral body as indicated by lines 260 and 260' in FIG. 14A, can also be used. In another embodiment, the aspiration sleeve can extend through the introducer 110A or can comprise an outer concentric sleeve around the introducer 110A.

Figure 15A:
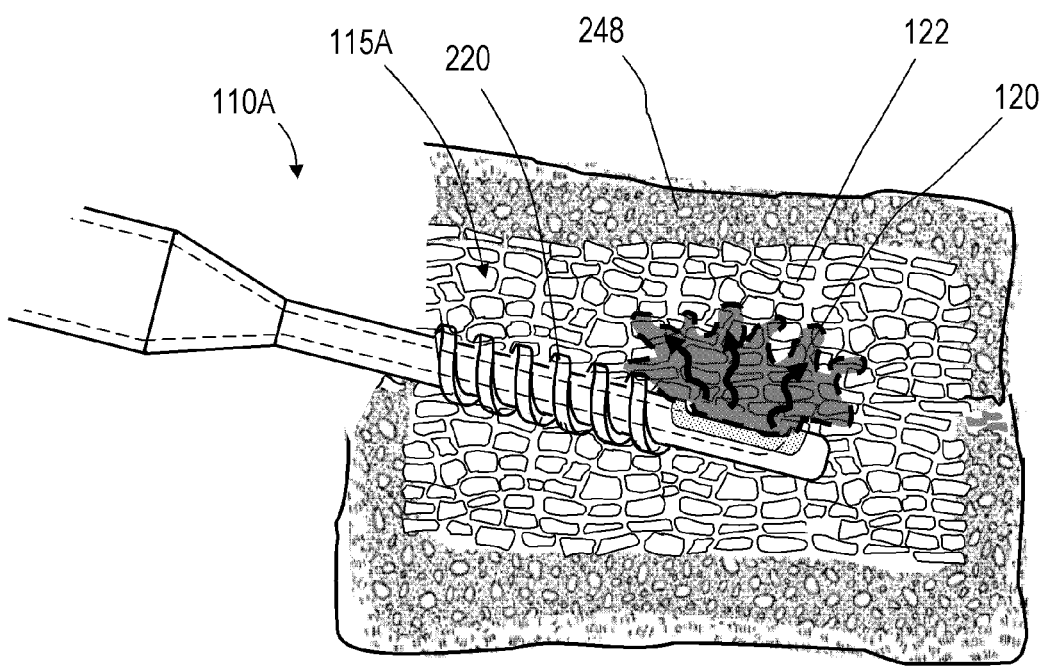
FIG. 15A is a sectional view of a vertebra depicting a first mode of operation wherein an initial flow of bone cement is provided under selected flow parameters that allow cement interdigitation into cancellous bone.
Figure 15B:
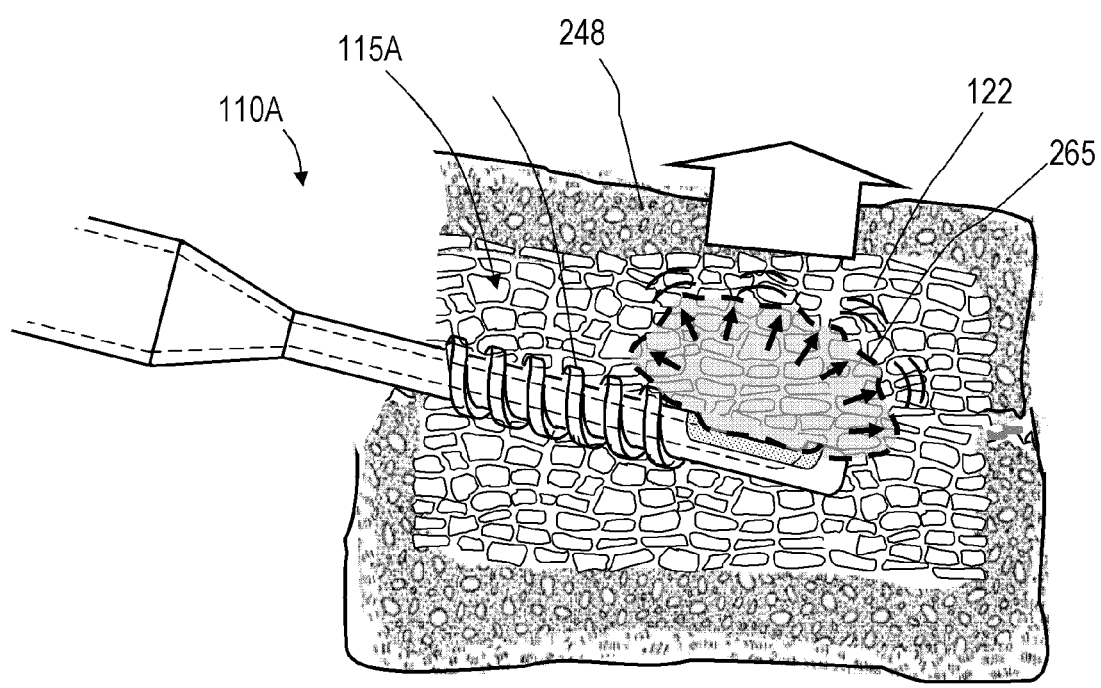
FIG. 15B is a sectional view of a vertebra similar to FIG. 15A depicting a second mode of operation wherein cement flows are provided in a high acceleration pulse that disallows cement interdigitation into cancellous bone.

FIGS. 15A and 15B illustrates another embodiment of a method for delivering bone fill material wherein the controller 125B and pressure source 150 are configured to introduce a flowable cement into the interior of a vertebra under widely varying velocities and rates of acceleration to optionally (i) provide first slow flow rates to allow cement flow and interdigitation into and through cancellous bone, and (ii) provide second higher flow rates that disallow cement interdigitation and flow into and through cancellous bone. At suitable high acceleration and flow velocity, for example in a pulse of cement flow into bone, the accelerated flow apply forces to bone substantially across the surface of the cement plume which can displace cancellous bone rather than allowing the cement to flow into the cancellous bone.

FIG. 15A illustrates the system of FIG. 13 in a method of use wherein the controller 125B and pressure source 150 are actuated to cause a volume of cement 120 to flow into cancellous bone 122 under a suitable low pressure to allow the cement to interdigitate with, and flow into, the cancellous bone. The flow of cement depicted in FIG. 15A can be accompanied by the application of aspiration forces as described above.

FIG. 15B illustrates another aspect of the method wherein the controller 125B and pressure source 150 are actuated to flow cement with a high acceleration rate and velocity that disallows the cement from having time to flow into pores of the cancellous bone. The acceleration and velocity are selected to disallow cement interdigitation, which thereby causes the application of force to bone across the surface of the cement plume 265 (FIG. 15B). The application of such forces across the surface of cement plume 265 is further enabled by providing a suitable high viscosity cement as described above, which includes selectively increasing cement viscosity by means of energy delivery thereto. The method of the invention can include one or more sequences of flowing cement into the bone to first cause cement interdigitation (FIG. 15A) and then to apply expansion forces to the bone by at least one high acceleration flow (FIG. 15B). Of particular interest, the method of using high acceleration flows, for example in pulses, causes the cement volume to apply forces to bone akin to the manner is which a mechanical expander or balloon expander would apply forces to bone. That is, expansion forces are applied across the entire surface of cement plume 265 similar to the manner in which mechanical instruments apply expanding forces across the bone engaging surface of the instrument. The methods are adapted for reducing a vertebral fracture and for selectively applying forces to move cancellous bone and cortical bone.

Retrograde Sensing Systems and Methods

Figure 16:
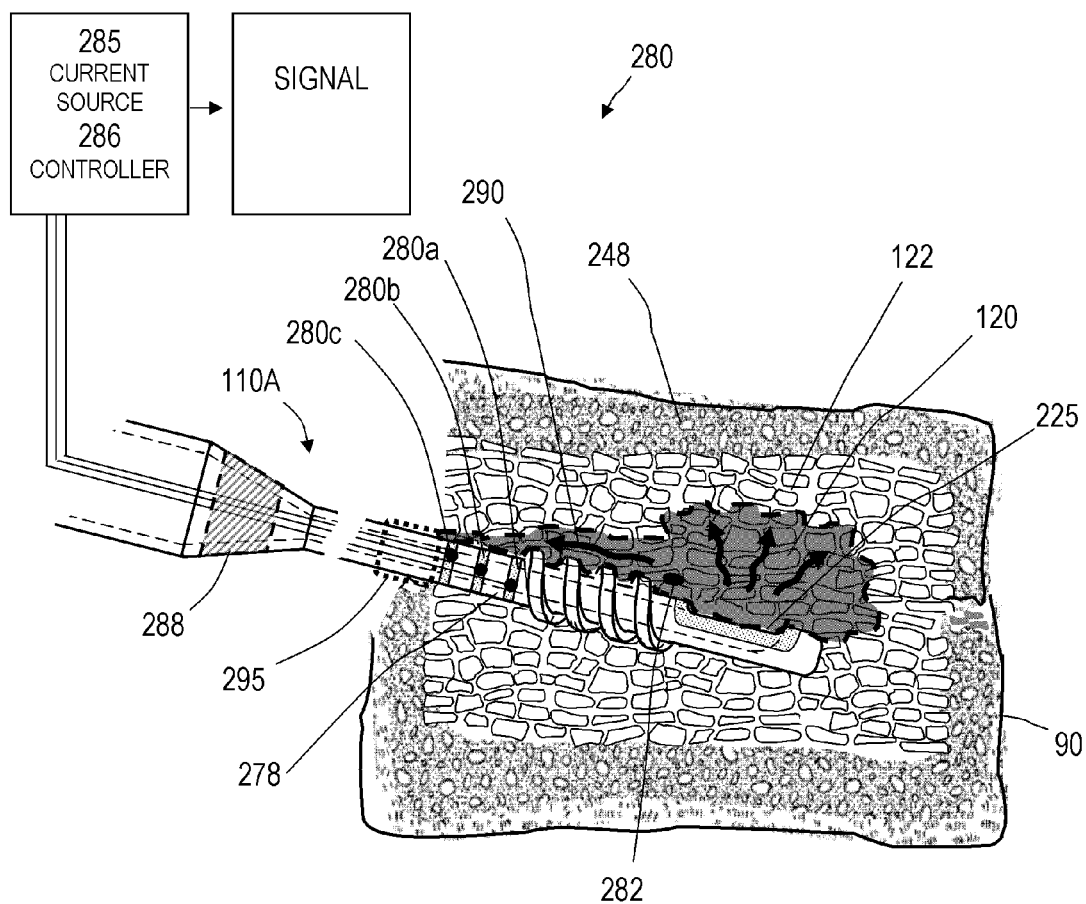
FIG. 16 is a sectional schematic view of another embodiment of a bone cement delivery system.

FIG. 16 illustrates another embodiment of an introducer 110A for safe introduction of bone cements into a vertebra that incorporates a sensing system 280. The sensing system 280 includes the introducer or cannula 110A with at least one distal port 225 for injection of bone cement into a vertebra 90, as described previously with respect to FIGS. 13-15B. This sensing system 280 further includes at least one electrode carried about an otherwise insulative exterior surface 278 of the cannula or introducer 110A. In the illustrated embodiment, the sensing system 280 has three electrodes or sensors 280a, 280b, 280c disposed about a surface of the introducer 110A, but it can be appreciated that more or fewer such electrodes can be used. In the illustrated embodiment, the electrodes 280a, 280b, 280c are ring electrodes, however other configurations are possible. Preferably, the electrodes 280a, 280b, 280c are independently coupled to a low voltage power source 285, which can be a DC or AC source, and to a controller 286 that allows for measurement of impedance between a pair of the electrodes 280a, 280b, 280c or between the electrodes 280a, 280b, 280c and another electrode 288 (in phantom) located in a more proximal location on the introducer 110A that contacts tissue, or between electrodes 280a, 280b, 280c and a ground pad. Such impedance measurements can advantageously provide the physician with instant feedback that indicates whether there in a flow 290 of bone cement 120 along the cannula 110A (e.g., a retrograde flow). Retrograde flows of cement can be seen by imaging means, but imaging is typically not performed continuously during vertebroplasty. Further, the cannula itself may obscure clear imaging of a cement flow. Such retrograde cement flows, if unnoticed, could leak through a fracture to contact nerves and/or the spinal cord. Though the sensors 280a, 280b, 280c in the illustrated embodiment are adapted to measure impedance, the sensors 280a, 280b, 280c can be adapted to measure other suitable electrical, chemical or mechanical parameters, such as temperature, voltage, and reflectance.

In FIG. 16, it can be seen that the retrograde flow 290 of bone cement 120 along the cannula 110A passes by, and in one embodiment may contact, first and second electrodes 280a and 280b, which will alter the impedance (or other sensed parameter) measured between the first and second electrodes 280a, 280b from the normal tissue impedance. The control algorithms advantageously create a signal to notify the physician of the variation in impedance measurement. The signal can be a tone, a visual signal such as a light and or a tactile signal such as a vibrator in the handle of the introducer 10A. The controller 286 can preferably switch sensing between various electrodes (e.g., adjacent electrodes or non-adjacent electrodes) to indicate the location of any migrating cement. The cement delivery system may use a conductive bone cement, as described in U.S. application Ser. No. 11/209,035 filed Aug. 22, 2005, which will have a significantly different impedance than tissue to allow for easy detection of cement flows. It should be appreciated that any conventional bone cement will have a different impedance than bone tissue so that a retrograde flow 290 of conventional bone cement can be detected. The controller 286 algorithms can be configured for any type of bone cement, wherein each type has a known impedance, reflectance, etc. For example, a bone cement formula can be provided for use with the controller 286 to measure impedance and detect variations in impedance due to bone cement flow. In one embodiment, the controller 286 preferably compares the sensed parameter (e.g., impedance) of the retrograde flow bone cement with a known value or value range for said parameter in bone tissue (e.g., vertebral tissue). The known values for the parameter can be stored in an algorithm or formulas stored in the controller 286 or in a separate memory. In another embodiment, the controller 286 can measure impedance (or other parameter values) of vertebral tissue adjacent at least one of the electrodes 280a, 280b and compare said measured impedance to a measured impedance of retrograde bone cement flow adjacent another of the electrodes 280a, 280b.

In another embodiment, the feedback from the sensing system 280 of FIG. 16 can be further adapted for actuating a control mechanism relating to operation of the vertebroplasty system. In one embodiment, as described in FIGS. 13-15B, the flow of bone cement is controlled by a controller 125B and pressure source 150. Feedback from the sensors 280a, 280b, 280c to the controller 286, which are used to measure impedance, can be used to adjust or terminate the flow of bone cement from the pressurized source of bone cement 145.

In another embodiment, the feedback from the sensing system 280 of FIG. 16 can be adapted to expand an expansion structure 295 (in phantom) about the surface of the cannula to prevent further bone cement migration. The expansion structure can be a fluid filled balloon, a thermally expandable polymer that has resistive or Rf energy applied thereto, or an elastomeric structure that can be expanded by axially or rotationally moving concentric cannula sleeves.

In another embodiment, the sensing system 280 can include a thermocouple 282 for measuring temperature of media proximate the exterior surface 278 of the cannula 110A. Such a temperature sensor can be well insulated from the interior bore of the cannula which will carry exothermic cement. The sensor system 280 can also include a light sensor system that can measure and compare a tissue parameter and a bone cement parameter. For example, a fiber optic can be provided to emit and/or receive light at the electrode locations in FIG. 16. Various parameters are possible such as reflectance. Alternatively, the bone cement can be configured with signaling compositions to cooperate with light emitted from a light source.

While the sensing system 280 has been described with the sensors being proximal to the cement injection port 225 of the cannula 110A, the sensors also can be elsewhere along the cannula 110A, for example at the distal end of the cannula 110A, to detect cement flow in that direction, such as in an anterograde direction.

Figure 17:
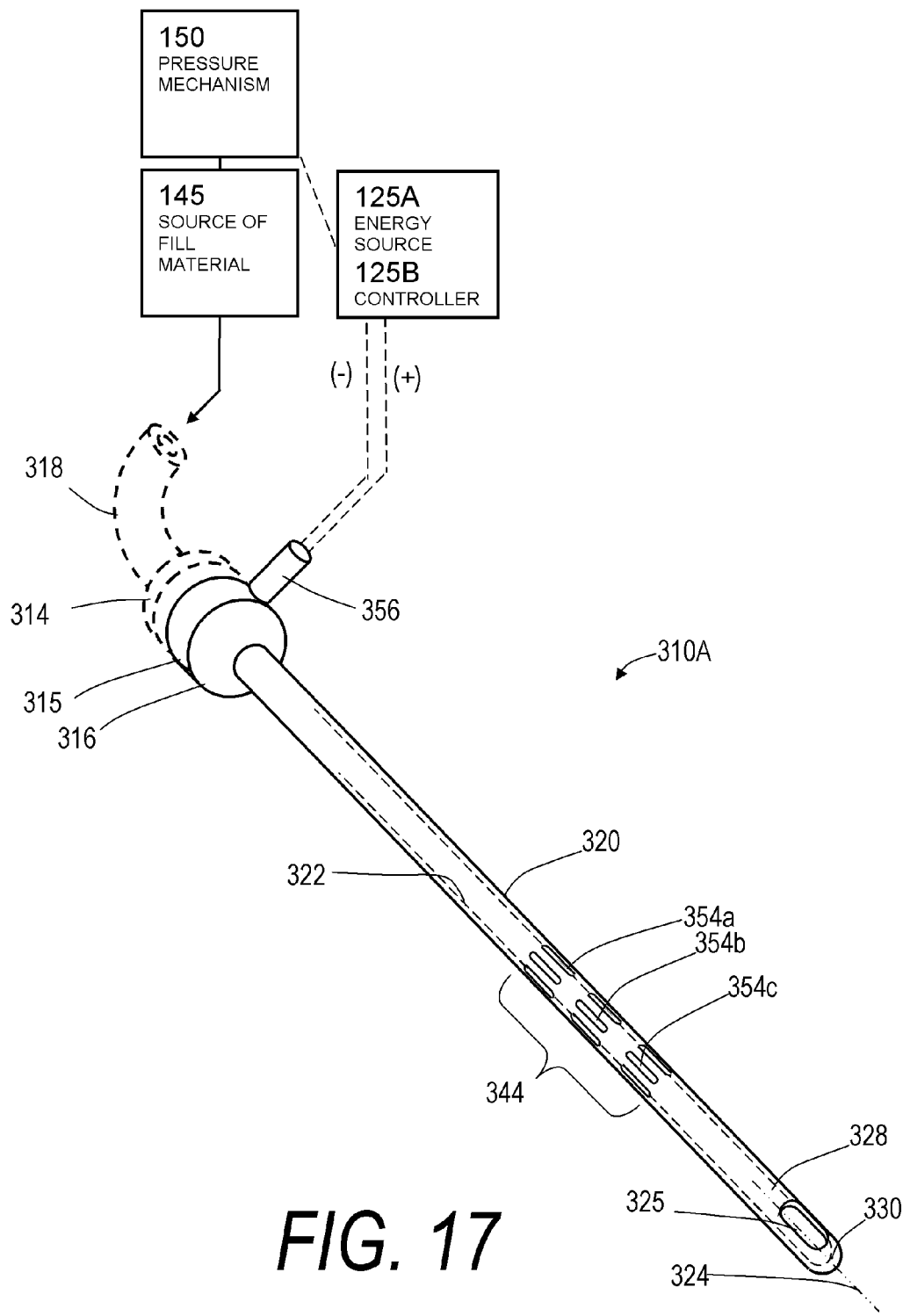
FIG. 17 is a schematic perspective view of another embodiment of a bone cement delivery system for treating osteoporotic bone or a fractured vertebra.

FIG. 17, shows another embodiment of a bone fill introducer or injector system 310A for treatment of the spine, such as in a vertebroplasty procedure. Introducer system 310A is used for placement a fill material from source 145, wherein injection of the fill material is carried out by the pressure mechanism or source 150. The pressure mechanism 150 can be a manually operated syringe loaded with bone fill material, or a non-manual pressurized source of fill material. The source 145 of fill material preferably includes a coupling or fitting 314 for sealable locking to a corresponding fitting 315 at a proximal end 316 of an elongated introducer sleeve or cannula 320. In one embodiment, the source of fill material 145 is coupled directly to fitting 315 with a threaded coupling, a Luer lock or the like. In another embodiment as in FIG. 17, a flexible tube 318 (phantom view) is used to couple the source 145 to the introducer 320.

With continued reference to FIG. 17, the bone fill introducer system 310A includes the elongated sleeve 320 with interior channel 322 extending along axis 324, wherein the channel 322 terminates in an outlet opening 325. In the illustrated embodiment, the outlet opening 325 is disposed proximal the distal end of the elongated sleeve 320 and faces a side of the sleeve 320. In the illustrated embodiment, the outlet opening 325 is a single opening. In other embodiments, a plurality of outlet openings can be disposed on an outward surface 328 of the sleeve 320 about a circumference of the sleeve 320. In another embodiment, an outlet opening can be provided at the distal tip 330. In one embodiment, the distal tip 330 is blunt. In another embodiment, the distal tip can be sharp as with a chisel-like tip.

As can be seen in FIG. 17, the exterior surface 328 of the introducer sleeve 320 carries at least one sensor system 344 adapted to sense the flow or movement of a fill material 345 (see FIGS. 18A-18C) proximate to the sensor system 344. The introducer sleeve 320 and sensor system 344 are particularly useful in monitoring and preventing extravasation of a fill material 345 in a vertebroplasty procedure. In the illustrated embodiment, the sensor system 344 comprises a plurality of spaced apart electrodes or sensors 354a, 354b, 354c coupled to the electrical source 125A via an electrical connector 356 preferably disposed at the proximal end of the introducer 320. The electrodes 354a, 354b, 354c are preferably spaced apart about the circumference of the introducer 320, as well as axially along the length of the introducer 320. The electrical source 125A preferably carries a low voltage direct current, such as an Rf current, between the opposing potentials of spaced apart electrodes. The voltage is preferably between about 0.1 volts to about 500 volts, or from between about 1 volt to about 5 volts, and preferably creates a current path through the tissue between a pair of electrodes. The current can be continuous, intermittent and/or multiplexed between different electrode pairs or groups of electrodes.

Figure 18A:
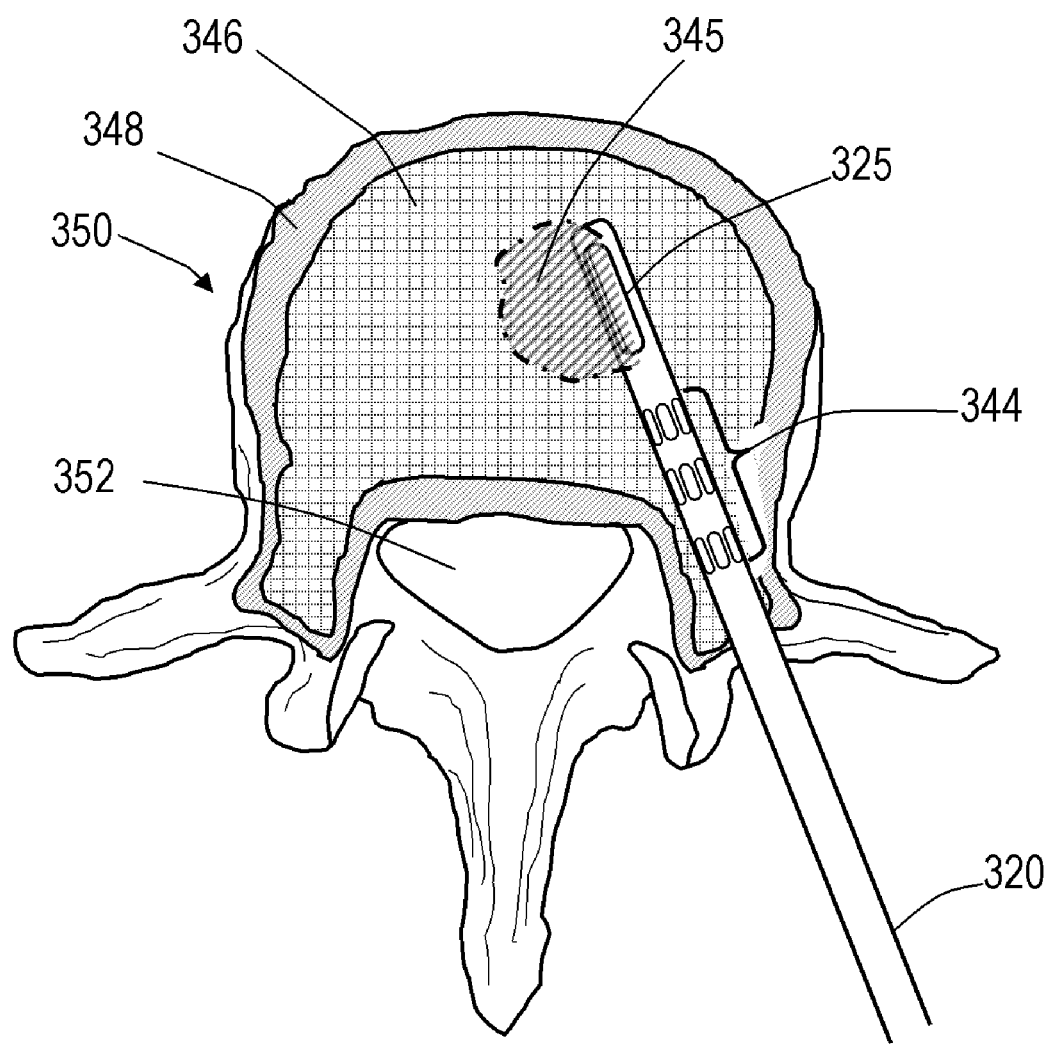
FIG. 18A is a sectional view of a vertebra showing one step of a method for delivering bone cement to a vertebra, in accordance with one embodiment.
Figure 18B:
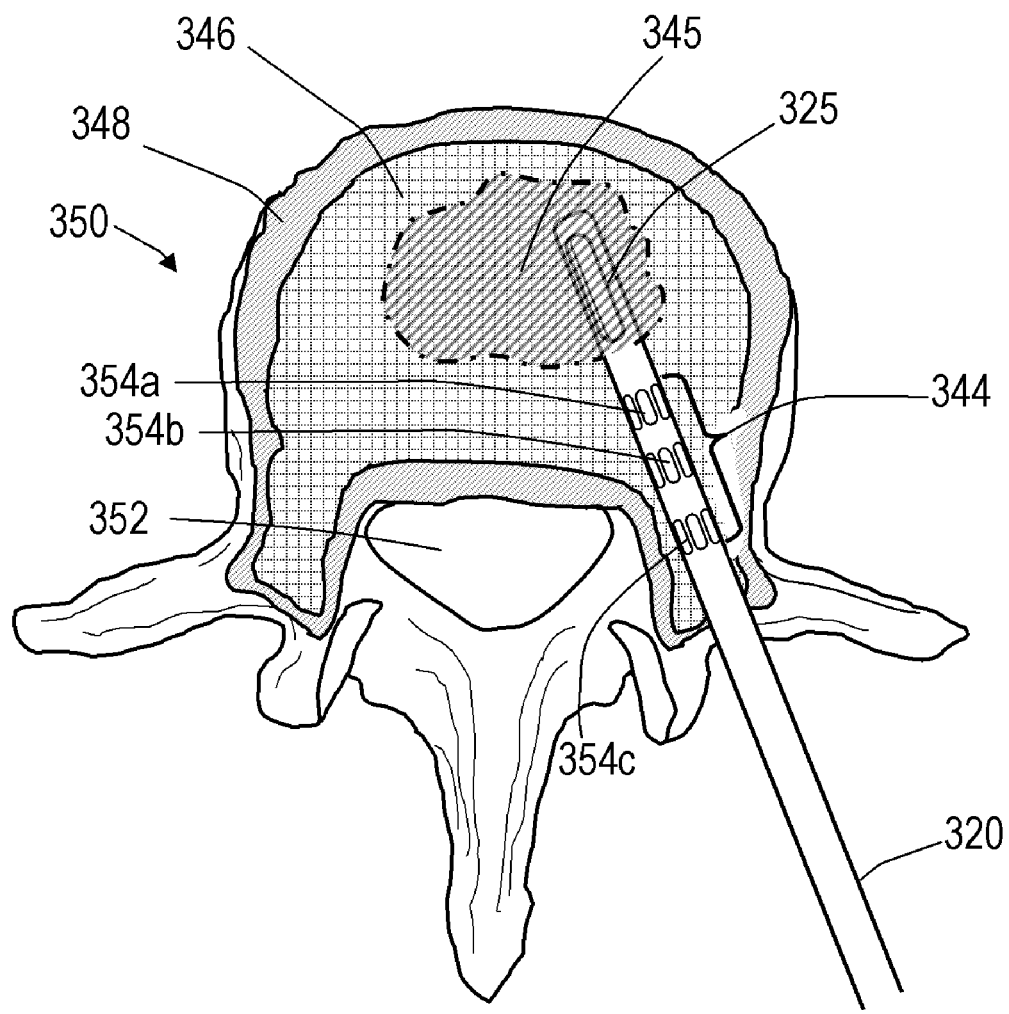
FIG. 18B is a sectional view of the vertebra of FIG. 18A showing another step of the method for delivering bone cement to a vertebra.
Figure 18C:
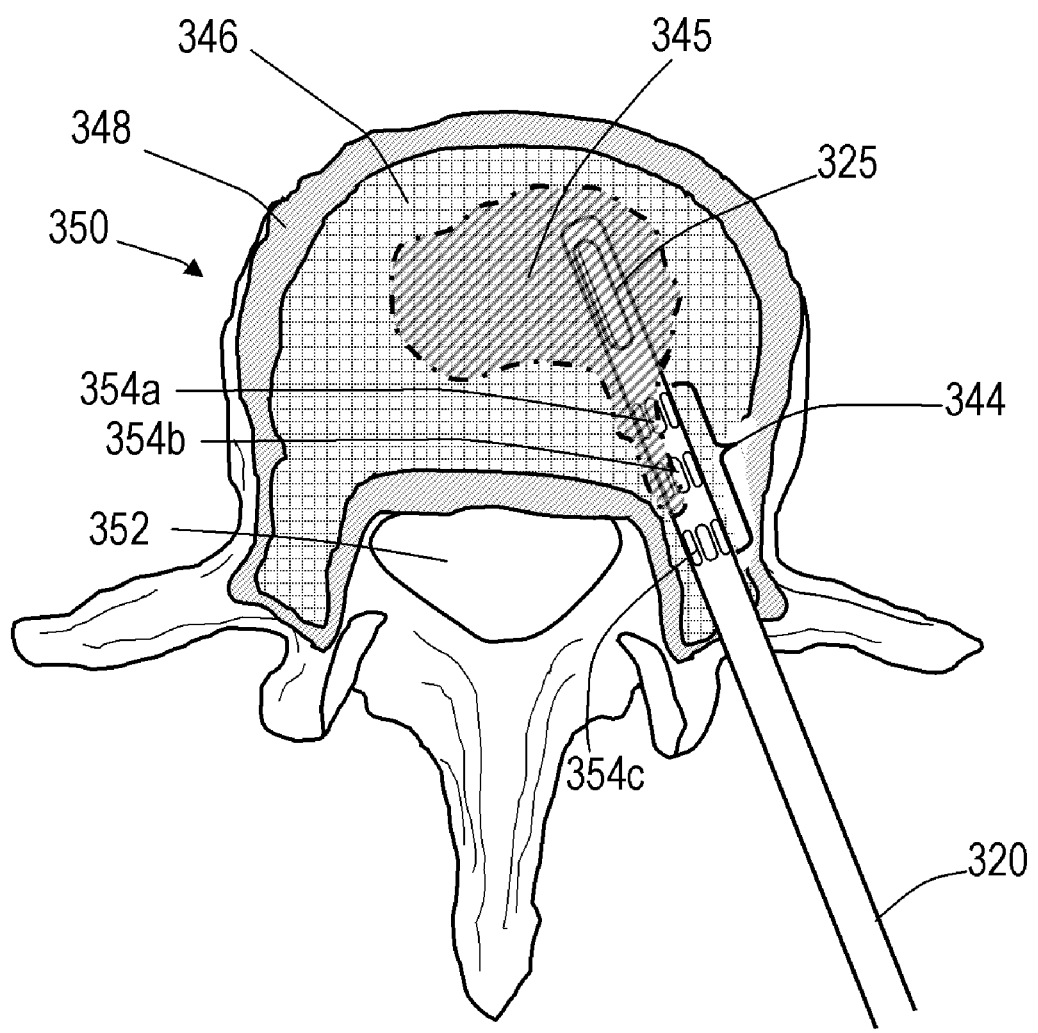
FIG. 18C is a sectional view similar to FIGS. 18A-18B showing another step of the method for delivering bone cement to a vertebra.

In one embodiment and method of use, referring to FIGS. 18A-18C, the introducer sleeve 320, as shown in FIG. 17, is used in a conventional vertebroplasty procedure with a single pedicular access through a vertebra 350. Alternatively, a bi-pedicular access can be used. The fill material 345 is preferably a bone cement, such as PMMA, that is injected into cancellous bone 346 within the interior of a cortical bone surface 348 of the vertebra 350.

FIGS. 18A-18B show a progressive flow of cement 345 that exits the introducer sleeve 320 through outlet 325 and into the interior of the vertebra 350. FIG. 18C depicts a situation that is known to occur where bone is fractured along the entry path of the introducer 320, or where the pressurized cement finds the path of least resistance to be retrograde along the surface of introducer 320. The retrograde flow of cement, as in FIG. 18C, if allowed to continue, could lead to cement extravasion into the spinal canal 352. In one embodiment, the sensor system 344 is actuated when the bone cement 345 comes into contact with at least one of the sensors 354a, 354b, 354c of the sensor system 344. In another embodiment, the sensor system 344 continually monitors the impedance adjacent the sensors 354a, 354b, 354c of the sensor system 344.

The arrangement of electrodes 354a, 354b, 354c can be spaced apart angularly and axially as shown in FIG. 17, or the electrodes can be ring electrodes (see FIG. 16), helically spaced electrodes, or the electrodes can be miniaturized electrodes as in thermocouples, MEMS devices or any combination thereof. The number of sensors or electrodes can range from about 1 to 100 and can be adapted to cooperate with a ground pad (e.g., ground pad 170 in FIG. 13) or other surface portion of sleeve 320. In one embodiment, the electrodes can include a PTC or NTC material (positive temperature coefficient of resistance or negative temperature coefficient of resistance) to thereby function as a thermistor to allow measurement of temperature, as well as functioning as a sensor. The sensor system 344 includes the controller 125B, which measures at least one selected parameter of the current flow to determine a change in a parameter such as impedance. When the bone cement 345 (e.g., a non-conductive bone cement material) contacts one or more electrodes of the sensor system 344, the controller 125B identifies a change in the selected electrical parameter and generates a signal to the operator. In another embodiment, the controller 125B identifies a change in the selected parameter when the bone cement 345 passes proximal one or more of the sensors of the sensor system 344 and communicates a signal to the operator corresponding to said change in said selected parameter. Said selected parameter can be at least one electrical property, reflectance, fluorescence, magnetic property, chemical property, mechanical property or a combination thereof.

Figure 19:
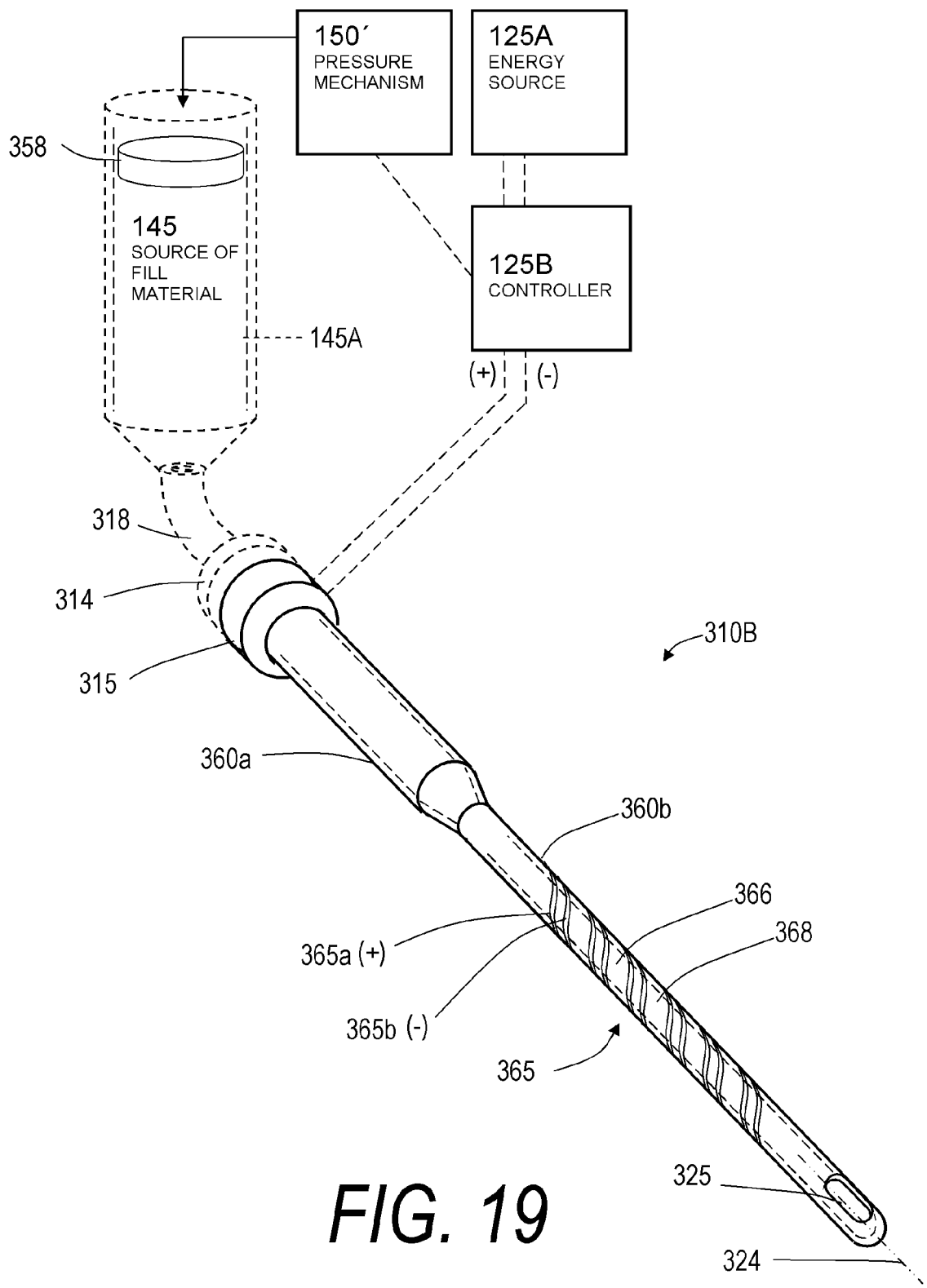
FIG. 19 is a perspective schematic view of another embodiment of a bone cement delivery system.

Now referring to FIG. 19, another embodiment of a bone fill system 310B for vertebroplasty procedures is shown. The bone fill system 310B includes an introducer 320 with a proximal portion 360a that is larger in cross-section than a distal portion 360b thereof. This advantageously allows for lower injection pressures since the cement flow needs to travel a shorter distance through the smallest diameter distal portion 360b of the introducer 320. In one embodiment, the distal portion 360b of the introducer 385 can have a cross section ranging between about 2 mm and 4 mm with a length ranging between about 40 mm and 60 mm. Similarly, in one embodiment the proximal portion 360a of the introducer 320 can have a cross section ranging between about 5 mm and 15 mm, or between about 6 mm and 12 mm. However the proximal and distal portions 360a, 360b of the introducer 320 can have other suitable dimensions.

With continued reference to FIG. 19, the bone fill system 310B also includes a sensing system 365 for detecting a retrograde flow of bone cement along an outer surface 366 of the introducer 320. In the illustrated embodiment, the sensing system 365 includes a first and a second electrode 365a, 365b in the form of spaced apart exposed flat wire surfaces that are disposed on the surface 366 of the distal introducer portion 360b, wherein the introducer 320 includes a surface insulator layer 368. In one embodiment, the insulator layer 368 covers the entire surface of the distal introducer portion 360b, and more preferably the entire surface of the introducer 320, except where the electrodes 365a, 365b are disposed. In another embodiment, the distal introducer portion 360b can be a conductive metal introducer portion with a first polarity electrode that is exposed in cut-out portions of insulator layer 368 and another opposing polarity electrode is disposed on the surface of the insulator layer 368. In the illustrated embodiment the electrodes or sensors 365a, 365b have a helical shape and extend helically along the introducer 320. However, in another embodiment, the electrodes 365a, 365b can have other suitable shapes (e.g., ring electrodes). Though FIG. 19 shows two electrodes 365a, 365b, one of ordinary skill in the art will recognize that more or less than two electrodes can be provided.

In the illustrated embodiment, the electrodes 365a, 365b are preferably electrically connected to the energy source 125A and controller 125B via lead lines (dashed lines). In one embodiment, the energy source 125A is an Rf electrical source capable of delivering sufficient Rf energy (i) to coagulate tissue which in turn will polymerize adjacent bone cement to create a dam to inhibit retrograde flows, or (ii) to deliver energy to a conductive bone cement 345 to inhibit retrograde flows. The opposing polarity electrodes indicated by the (+) and (−) can be spaced apart any selected distance to thus operate in a bi-polar manner wherein the depth of tissue coagulation will depend, at least in part, on the approximate center-to-center or edge-to-edge dimensions of the positive and negative electrodes. Thus, any such electrode arrangement can be adapted to both sense retrograde flows and thereafter deliver energy to such flow in response to at least one feedback algorithm in the controller 125B. Any suitable type of external thermal energy emitter that is linked to the sensor system 365 for inhibiting retrograde flows can be used, such as the energy emitter 128 discussed above with respect to FIG. 2A. The exterior thermal energy emitter can be a resistively heated emitter, a resistive coil, a PTC heating element, a light energy emitter, an inductive heating emitter, an ultrasound source, a microwave emitter or any other electromagnetic energy emitter or Rf emitter that cooperates with the bone cement.

Figure 20:
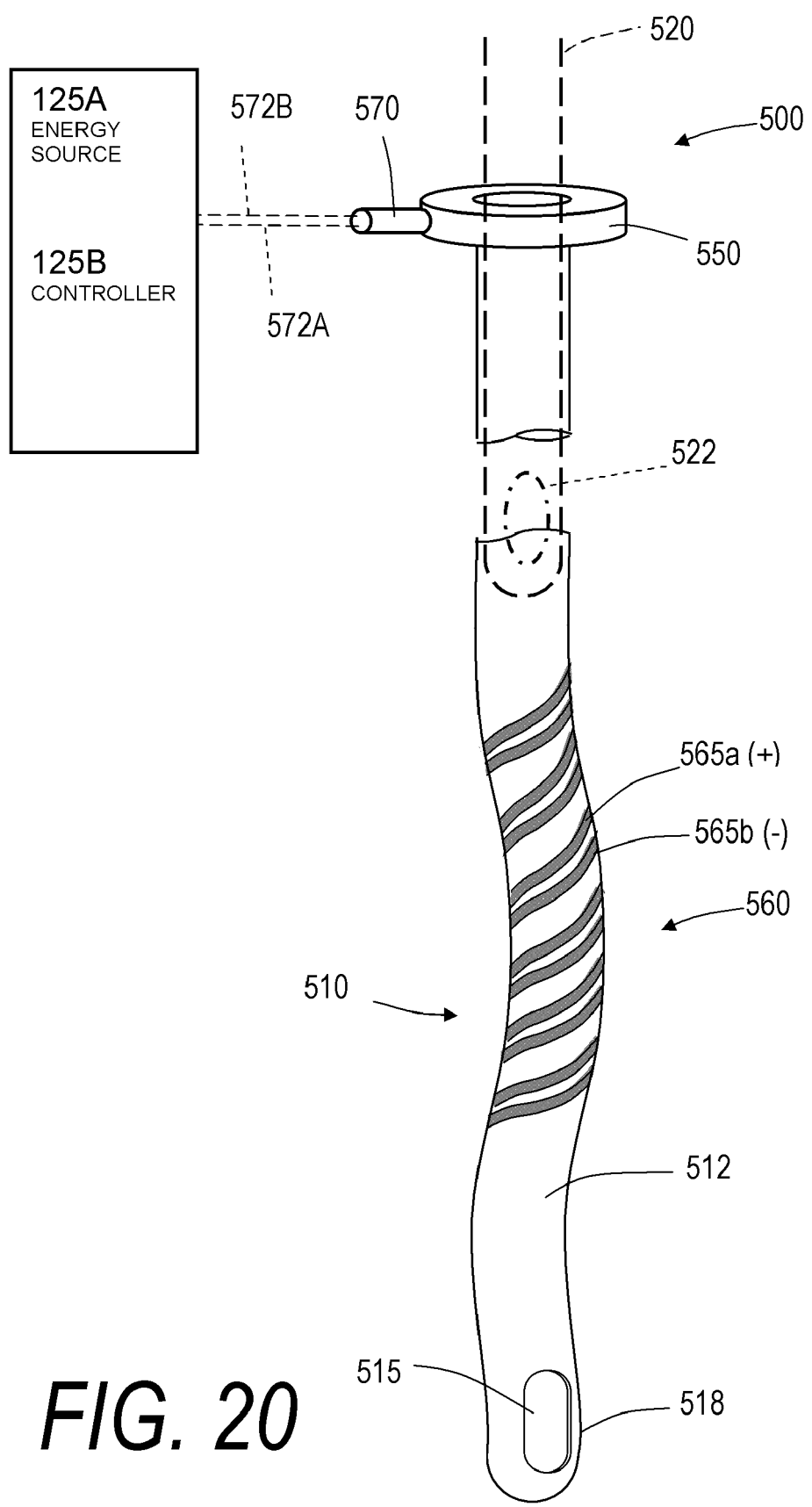
FIG. 20 is a perspective schematic view of another embodiment of an injector with a thin wall sleeve and a sensor system.

FIG. 20 shows another embodiment of an introducer system 500 that includes a thin wall sleeve or sheath 510 removably slidable over an injector or introducer 520 (in phantom) used in conventional vertebroplasty procedures and adapted for ejection of bone fill material (e.g., bone cement) through an outlet opening 522 (in phantom) at a distal end of the introducer 520. In the illustrated embodiment, the sheath 510 has an opening 515 formed at a distal end 518 of the sheath 510, wherein the opening 515 preferably aligns with the opening 522 of the of the introducer 520 when the sleeve 510 is deployed over the introducer 520. In the illustrated embodiment, the sleeve 510 is preferably a thin-wall flexible sleeve. For example, the sleeve 510 can be fabricated of silicone, polyethylene, urethane, polystyrene, or any other suitable polymer. The sleeve 510 can be elastic and dimensioned for a substantially tight grip fit about the injector 520. In another embodiment, the sleeve 510 can include a tacky or adhesive surface for engaging the injector 520. In another embodiment, the sleeve 510 can be invertable with or without a self-stick surface to roll over the injector 520 (e.g., as a condom). In another embodiment, the sleeve 510 can comprise a heat shrink material to shrink over the injector 520. In another embodiment, the sleeve 510 can be a thin-wall flexible sleeve that has a large diameter compared to injector 520 so that the sleeve 510 fits loosely over the injector 520, where the sleeve 510 is adapted to longitudinally fold about the injector 520 for inserting into a path in the cancellous bone. Upon any retrograde flow of cement, said thin wall material advantageously tends to crumple and engage the cancellous bone to form a mechanical dam to inhibit retrograde flows. In still another embodiment (not shown), the sleeve can be a thin-wall substantially rigid or rigid sleeve that can slip over the introducer 520, and be made of, for example, metal or a hard plastic.

The system 500 preferably includes a sensor system 560, which includes a first and second spaced apart electrodes 565a, 565b, similar to the electrodes 365a, 365b described above with respect to FIG. 19. The electrodes 565a, 565b are preferably disposed on an outer surface 512 of the sleeve 510. In the illustrated embodiment, the electrodes or sensors 565a, 565b have a helical shape and extend helically along the length of the sleeve 510. However, the electrodes 565a, 565b can have any suitable shape (e.g., ring electrodes). Additionally, any number of electrodes 565a, 565b can be provided.

With continued reference to FIG. 20, the sensor system 560 includes an electrical connector 570 that connects to a proximal end 514 of the sleeve 510. The connector 570 is configured for detachable coupling with electrical leads 572A, 572B that extend to the electrical or energy source 125a. The electrical leads 572A, 572B preferably are electrically connected to the electrodes 565a, 565b. In one embodiment, the electrodes 565a, 565b can be used to sense a retrograde flow of bone cement, where the signals (e.g., of impedance as discussed above) are communicated to the controller 125B, which in turn generates a signal (e.g., visual, tactile, auditory) to notify the operator of the retrograde flow, as discussed above. In another embodiment, the sensor system 560 can operate as an energy-delivery system, where the controller 125B controls the operation of the energy source 125A to control the delivery of electricity to the electrodes 565a, 565b to, for example, polymerize bone cement proximal the sensors 565a, 565b or coagulate tissue proximal the sensors 565a, 565b, as discussed above.

Hydraulic Pressure Mechanism

Returning to FIG. 19, system 310B includes a container of fill material or source 145' that is pressurized by a pressure mechanism 150'. The pressure mechanism 150' can be a hydraulic source. For example, in one embodiment, the hydraulic source can include a syringe, or plurality of syringes, with a conduit containing a working fluid therein and connecting the syringe to a proximal end of the fill material source 145'. The working fluid can transfer the force generated by the syringe onto a piston 358 (e.g., a floating piston) that travels through a sleeve 145A of the fill material source 145' to eject fill material from the fill material source 145' into the introducer 320. In another embodiment the hydraulic source can comprise a plurality of syringes connected via conduits having working fluids therein, the force generated by one syringe transferred through the working fluid onto a piston of a downstream syringe, and eventually transferred to the piston 358 in the sleeve 145A. In still another embodiment, the hydraulic mechanism can include a screw pump actuatable to transmit a force onto a working fluid in a conduit, which in turn transmits said force onto the piston 358 in the sleeve 145A. However, the pressure mechanism 150' can comprise other suitable mechanisms.

Temperature Control Systems

Figure 21:
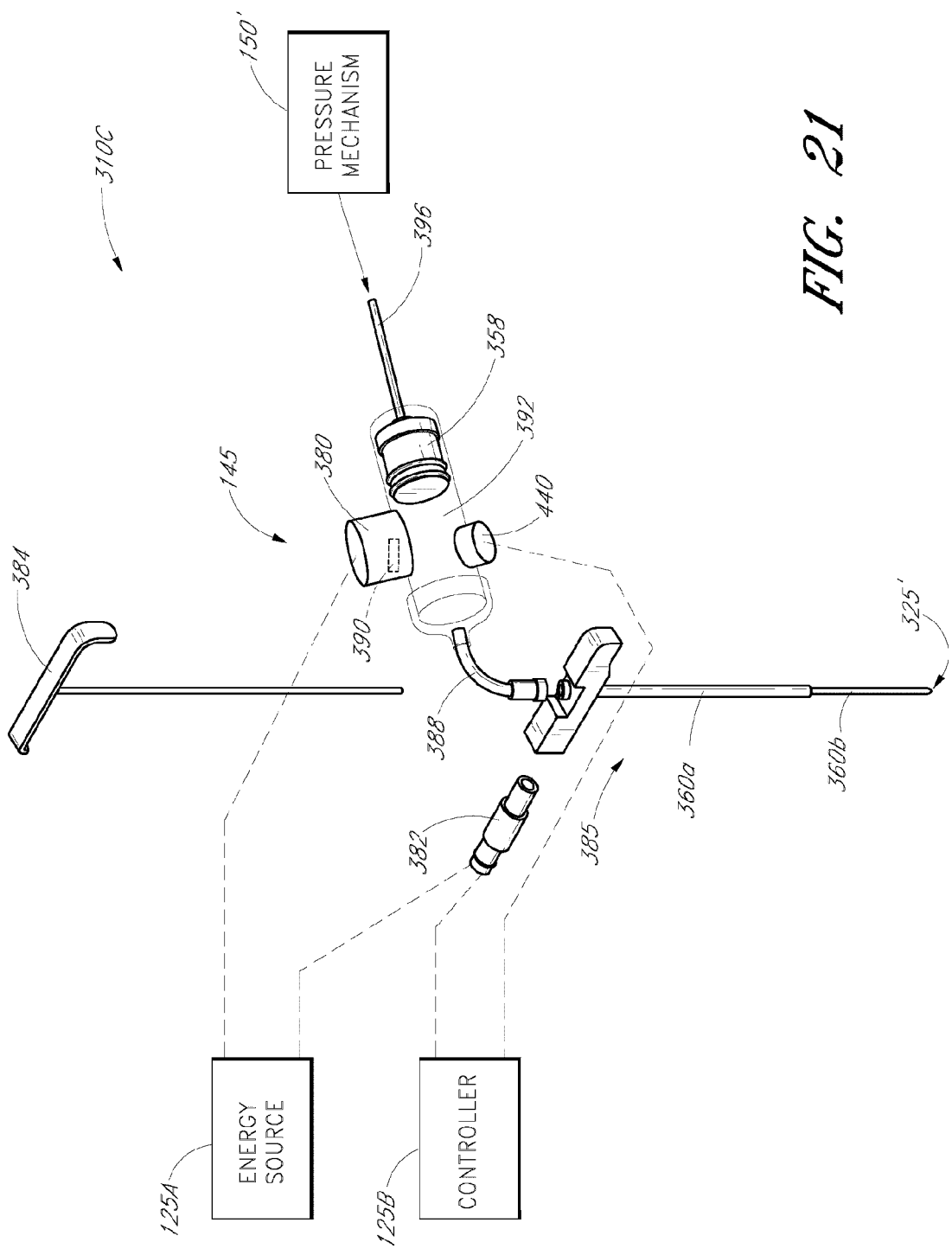
FIG. 21 is a perspective schematic view of another embodiment of a bone cement delivery system.

FIG. 21, shows another embodiment of a bone fill delivery system 310C. The system 310C is similar to the system 310B in FIG. 19, except as noted below. Thus, the reference numerals used to designate the various components of the system 310C are identical to those used for identifying the corresponding components of the system 310B, except as noted below.

Figure 22:
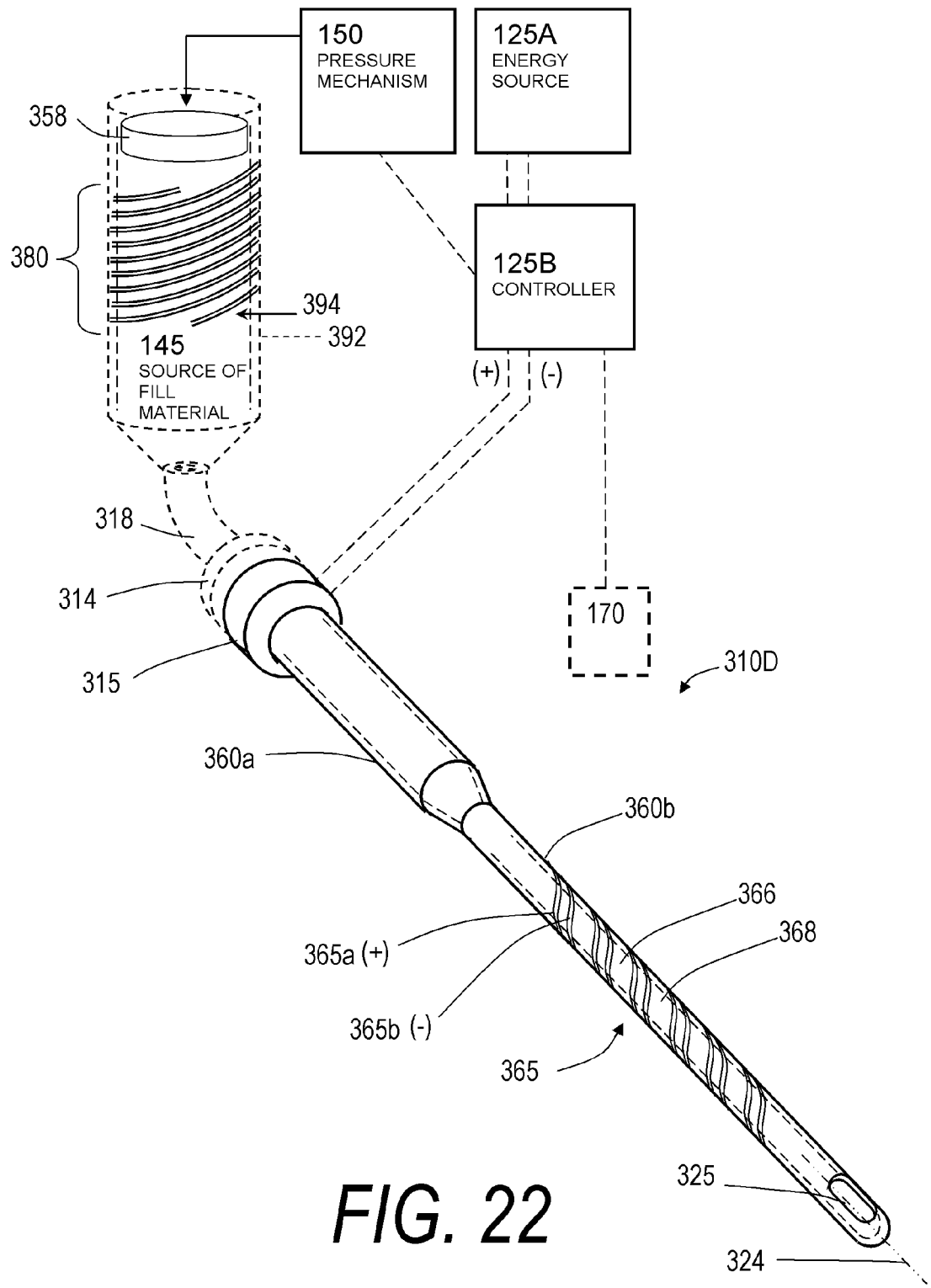
FIG. 22 is a perspective schematic view of another embodiment of a bone cement delivery system.

The system 310C can include a sensing system for detecting retrograde flows of bone cement, as discussed above. Further, the system 310C preferably includes a cooling system or mechanism 380, which is shown schematically in FIG. 21. In one embodiment, the cooling mechanism 380 is carried within the container 145 that carries the fill material (e.g., PMMA bone cement or similar in-situ hardening cement) as shown in FIG. 22. In another embodiment, the cooling mechanism 380 can be disposed about the container 145. As can be seen in FIG. 21, the electrical source 125A and controller 125B are coupled to the introducer 320 via leads that are electrically connected to a detachable coupling 382 coupleable to the introducer 320. A stylet 384 is also provided, preferably having a sharp tip, for use in embodiments where the introducer 320 has a distal open port 325'.

The cooling system 380 of FIG. 21 advantageously maintains a volume of mixed bone cement at a pre-determined temperature to inhibit acceleration of the exothermic heating thereof, thus extending the working time of the cement. In one embodiment, as shown in FIG. 21, the introducer 320 is an independent introducer 320 sized and configured for introducing the bone cement 345 (FIGS. 18A-18C) into the vertebra 350. In the illustrated embodiment, the bone cement container 145 has a fitting and optional flexible sleeve connector 388 for providing a substantially sealed and substantially pressure-tight coupling between the container 145 and the introducer 320 The connector 388 preferably has a length of between about 10 mm and about 100 mm and can optionally include a cooling system disposed therein.

The cooling system 380 preferably includes at least one of an active cooling system and a passive cooling system. In one embodiment, shown in FIG. 21, the cooling system 380 includes a thermoelectric system with at least one element 390 (e.g., a Peltier element) in contact with a thermally conductive wall portion 392 of the container 145. In another embodiment, the cooling system 380 includes a chilled fluid circulation system with channels 394 disposed proximate the wall portion 392 of container 145 (See FIG. 22). In another embodiment (not shown) the cooling system 380 includes a freon system with an expansion channel inside the wall portion 392 of the container 145. However, the cooling system 380 can include other suitable active cooling arrangements. In still another embodiment (not shown), the cooling system 380 includes a heat pipe system with at least one elongate channel or concentric channel in the wall portion 392 of the container 145, which wicks heat away from the container 145 to a heat exchanger component. In yet another embodiment (not shown), the cooling system 380 is a passive system that includes an open cell graphite structure for conducting heat away from the container 145 to a heat exchanger component. In one embodiment, the open cell graphite is PocoFoam™ manufactured by Poco Graphite, Inc. 300 Old Greenwood Road, Decatur, Tex. 76234.

With continued reference to FIG. 21, the bone fill injection system 310C includes the pressure source or mechanism 150', as discussed above with respect to FIG. 19. In the illustrated embodiment, the pressure source 150' is a hydraulic mechanism coupled to the container 145 via flexible or deformable tubing 396 to drive the piston 358.

As shown in FIG. 21, the controller 125B can be further coupled to at least one sensing system 440 for determining the viscosity of the bone cement in the container 145. Preferably, the sensing system 440 is at least partially disposed in the container 145. The controller 125B preferably includes algorithms for preventing any flow of bone cement through the introducer 320 until the cement has reached a predetermined viscosity.

In one embodiment, the sensing system 440 includes an electrical parameter sensing system for querying an electrical parameter of a polymerizable bone cement to thereby determine its viscosity. Such an electrical sensor can preferably measure at least one of capacitance, conductivity and impedance. Another embodiment of sensing system 440 includes a mechanical parameter sensing system for measuring a mechanical parameter of the bone cement. For example, the mechanical parameter sensing system can query the bone cement by applying an acoustic wave thereto. In still another embodiment, the sensing system 440 includes an optical parameter sensing system for determining the viscosity of the bone cement by measuring an optical parameter of a polymerizing bone cement. For example, the optical parameter sensing system can measure reflectance of the bone cement. In another embodiment, the optical parameter sensing system can acquire an optical signature of a bone cement that carries a thermochromic composition. In another embodiment, the sensing system 440 includes a temperature sensing system for determining the viscosity of the bone cement via a measured the temperature of a polymerizable bone cement in the container 145. In still another embodiment, the sensing system 440 includes a strain gauge (not shown) disposed in the container 145 or drive system to determine the viscosity of the cement. In another embodiment, the sensing system 440 uses a pressure sensor, such as a MEMS pressure sensor, to determine the viscosity of the bone cement. Any of the sensing systems described herein can be configured to query the parameter of the bone cement continuously or intermittently at any suitable rate.

Figure 23A:
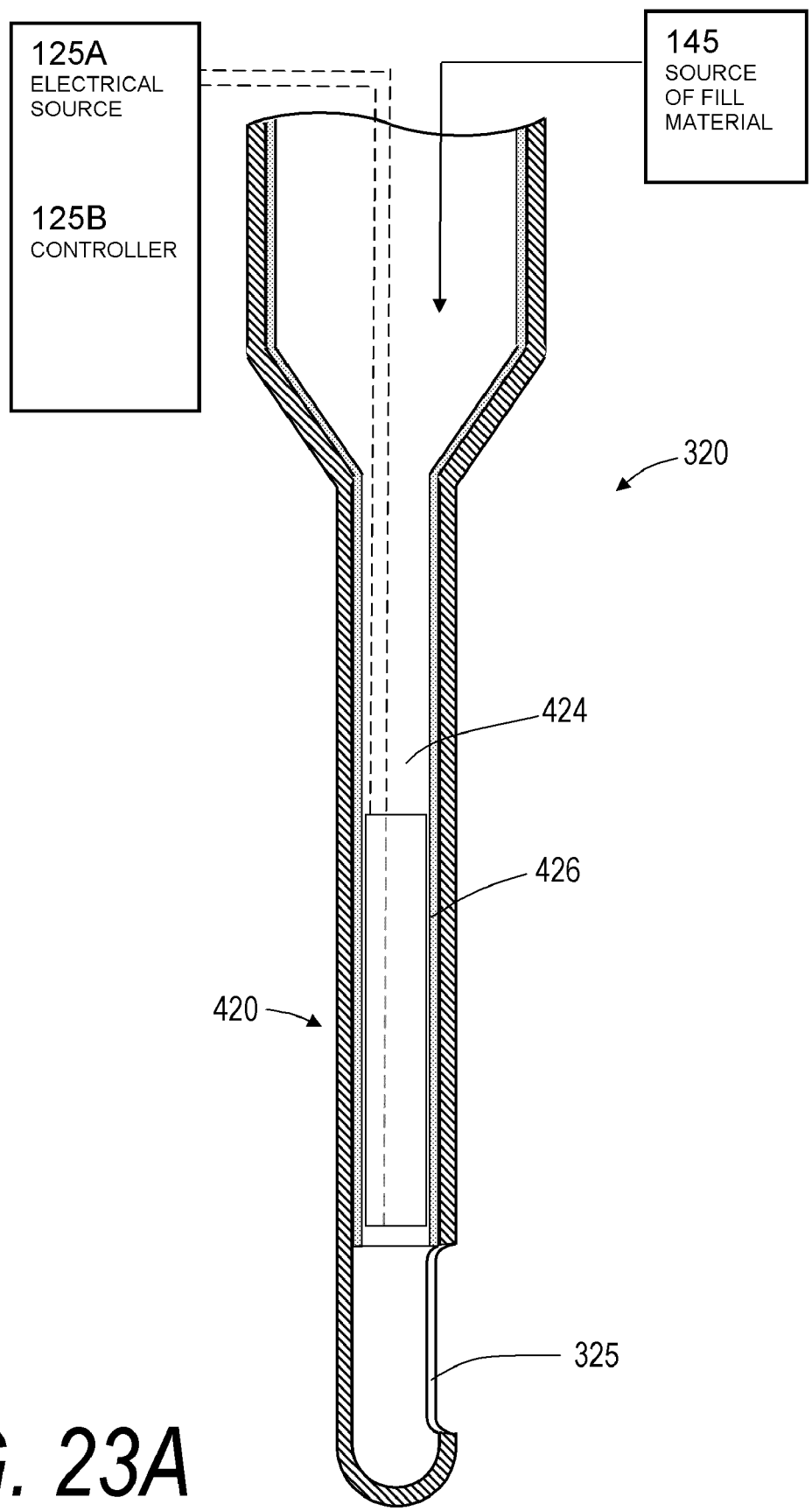
FIG. 23A is a sectional view of one embodiment of a bone cement injector having an energy emitter.

With continued reference to FIG. 21, the bone fill injection system 310C optionally further includes a thermal energy emitter 420 (See FIG. 23A) disposed within an interior channel 424 of the introducer 320 for heating a flow of bone cement exiting the introducer 320 through the outlet opening 325, as shown in FIG. 23A. In one embodiment, the thermal energy emitter 420 is an Rf emitter adapted for heating a conductive bone cement as disclosed in the following co-pending U.S. Patent Applications: application Ser. No. 11/165,652 filed Jun. 24, 2005; application Ser. No. 11/165,651 filed Jun. 24, 2005, now U.S. Pub. No. 2006-0122622; application Ser. No. 11/196,045 filed Aug. 2, 2005; application Ser. No. 11/208,448 filed Aug. 20, 2005; and application Ser. No. 11/209,035 filed Aug. 22, 2005, the entire contents of which are hereby incorporated by reference and should be considered a part of this specification. In another embodiment, the thermal energy emitter 420 delivers thermal energy to the bone cement via conduction in the distal region of the introducer 320. The thermal energy emitter 420 can be a resistive heat emitter, a light energy emitter, an inductive heating emitter, an ultrasound source, a microwave emitter and any other electromagnetic energy emitter to cooperate with the bone cement.

Figure 23B:
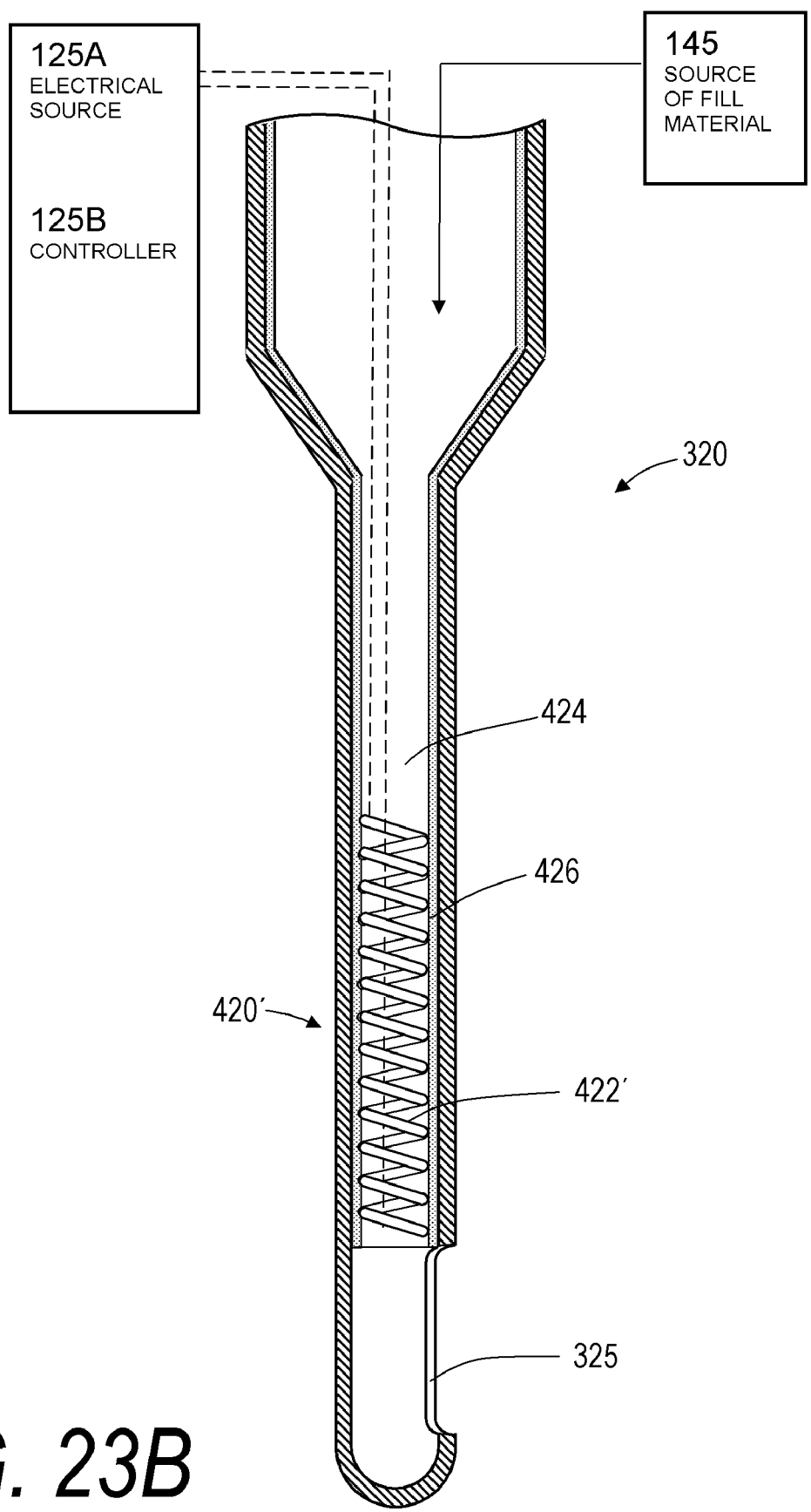
FIG. 23B is a sectional view of another embodiment of a bone cement injector having an energy emitter.

In another embodiment, shown in FIG. 23B, the thermal energy emitter is a resistive heater 420' with a resistive heating element 422. The heating element 422 preferably has a helical configuration, though other suitable configurations are possible, such as an axial configuration. Additionally, the heating element 422 is preferably disposed in an interior bore 424 of the introducer 320 and can optionally be formed from (or coated with) a positive temperature coefficient material and coupled to a suitable voltage source to provide a constant temperature heater as is known in the art. Preferably, the heating element 422 is carried within an insulative coating 426 on an interior surface of the introducer 320.

In one embodiment, the thermal energy emitter 420, 420' raises the temperature of the chilled bone cement to body temperature or within about 5° C. above or below body temperature. In another embodiment, thermal energy emitter 420, 420' raises the temperature of the chilled bone cement 345 to at least about 45° C., at least about 55° C. in another embodiment, at least about 65° C. in still another embodiment, and between about 45° C. and 95° C. in another embodiment to accelerate polymerization of the bone cement 345 and increase the viscosity of a PMMA or similar bone cement. In another embodiment, the thermal energy emitter 420, 420' raises the temperature of the chilled bone cement 345 to between about 50° C. and 85° C., or between about 50° C. and 65° C. to accelerate polymerization of bone cement 345.

In the embodiments illustrated in FIGS. 21, 22 and 23A-B, the controller 125B preferably controls all parameters associated with cooling of the bone cement in the container 145, cement injection pressure and/or flow rate, energy delivery to cement flows in or proximate the distal end of the introducer 320, sensing of retrograde flows, and energy delivery to retrograde flows about the exterior surface of the introducer 320.

FIG. 22 illustrates another system 310D for delivery of bone infill material. The system 310D is similar to the system 310B in FIG. 19, except as noted below. Thus, the reference numerals used to designate the various components of the system 310D are identical to those used for identifying the corresponding components of the system 310B, except as noted below. In the illustrated embodiment, the arrangement of the electrodes 365a, 365b can be multiplexed between a bi-polar mode and a mono-polar mode using a remote return electrode (ground pad) 170.

Injector Coatings

Figure 24:
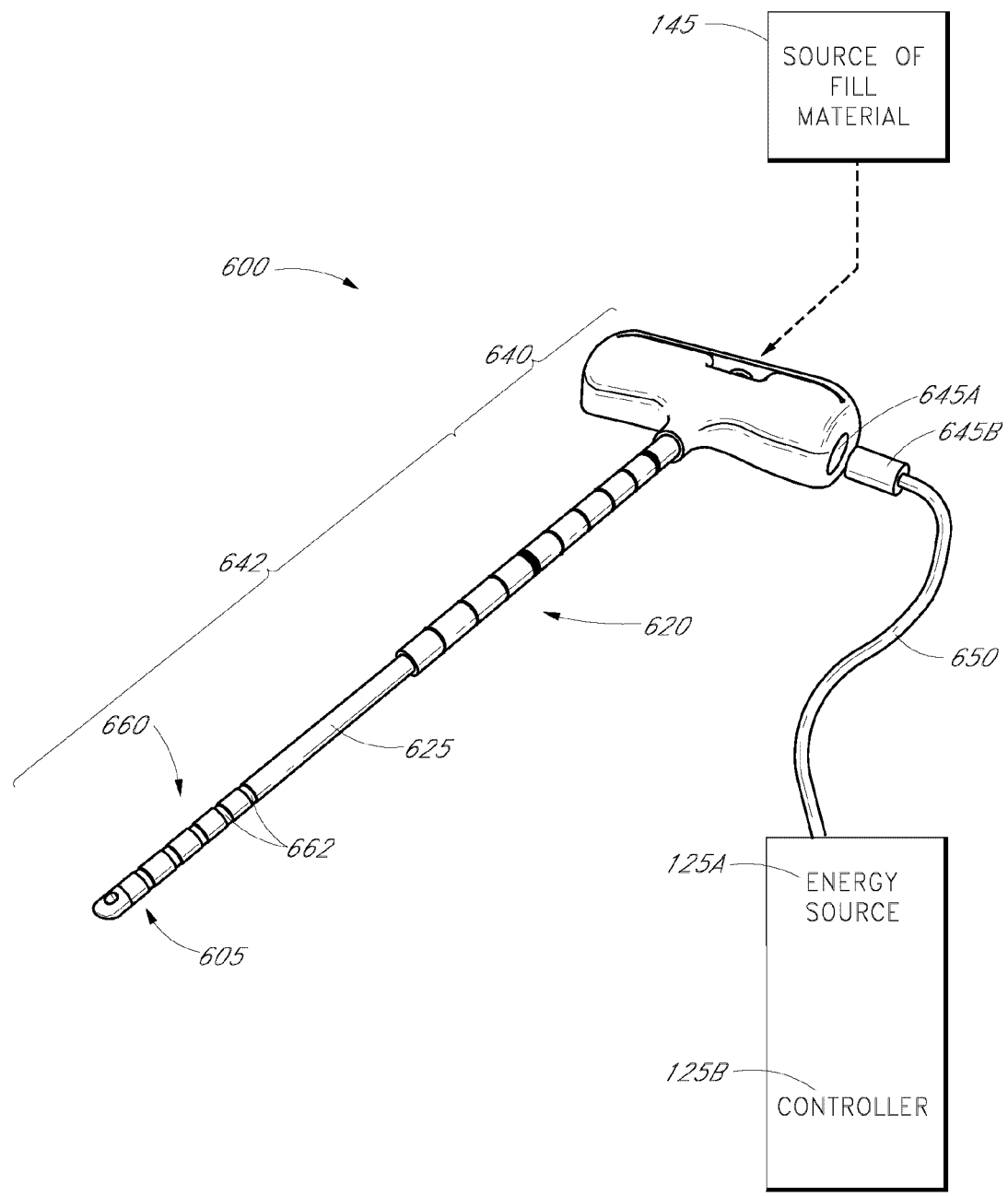
FIG. 24 is a perspective schematic view of another embodiment of a bone cement delivery system.
Figure 25:
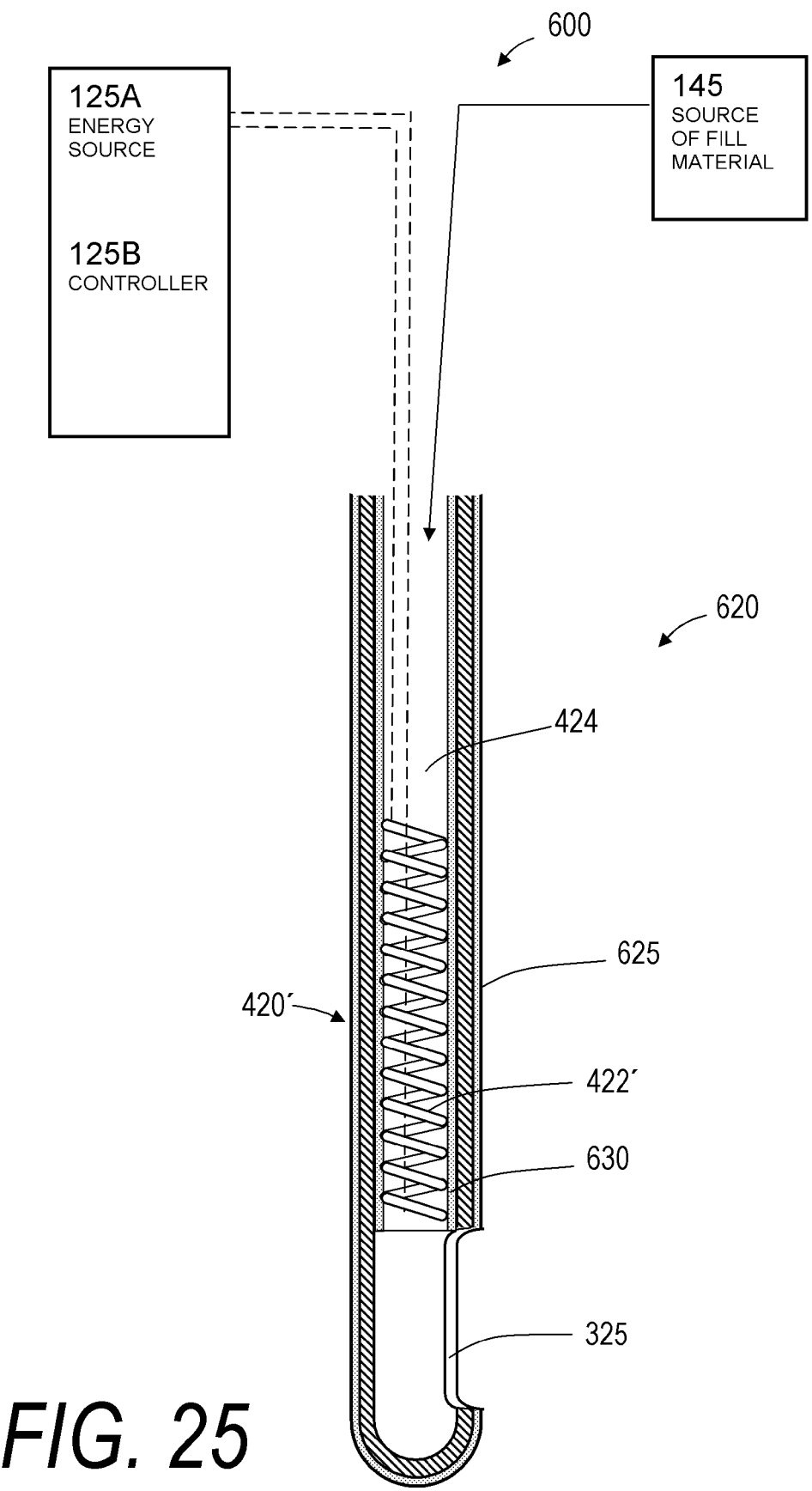
FIG. 25 is a sectional schematic view of another embodiment of a bone cement injector.

FIGS. 24 and 25 show another embodiment of a bone infill material delivery system 600, which again comprises a bone cement injector 620 that extends to a working end 605 thereof. However, the features described below are applicable to any electrosurgical probe or other heated probe. The injector 620 has a handle portion 640 and an extension portion 642 with a flow passageway 424 extending therethrough (See FIG. 25). The extension portion 642 is preferably sized and shaped for use in a vertebroplasty procedure.

As shown in FIG. 24, the injector 620 has an exterior surface that includes a coating 625. The coating 625 preferably comprises a thin layer of a non-metallic material, such as an insulative amorphous diamond-like carbon (DLC) or a diamond-like nanocomposite (DCN). Such coatings advantageously inhibit scratching (e.g., have high scratch resistance), as well as have lubricious and non-stick characteristics that are useful in bone cement injectors configured for carrying electrical current for (i) impedance sensing purposes; (ii) for energy delivery to bone fill material; and/or (iii) ohmic heating of tissue, such as the injectors 110A, 320, 620 discussed herein. In a preferred embodiment, the coating has a scratch resistance of at least about 10 on the Mohs scale, or above about 12 on the Mohs scale in another embodiment, or above about 14 on the Mohs scale in still another embodiment. A surface of the injector can have a lubricious level represented by a static coefficient of friction of less than about 0.5 in one embodiment, less than about 0.2 in another embodiment, and less than about 0.1 in still another embodiment. In one embodiment, the DLC or DNC coatings can have an overlying layer of Teflon, or similar material, to provide the desired lubricious level. For example, when inserting a bone cement injector through the cortical bone surface of a pedicle and then into the interior of a vertebra, it is important that the exterior insulative coating portions do not fracture, chip or scratch to thereby ensure that the electrical current carrying functions of the injector 110A, 320, 620 are not compromised.

With continued reference to FIG. 24, the source of bone fill material 145 is coupleable to the flow passageway 424 of the introducer 620. In addition, the handle portion 640 of the injector 620 includes a connector 645A that allows for releasable connection of the injector 620 with an electrical connector 645B coupled to the electrical or energy source. The extension portion 642 is preferably sized and shaped for use in a vertebroplasty procedure and to the controller 125B via an electrical cable 650. The electrical cable 650 preferably carries current to the working end 605 of the bone cement injector 620. In another embodiment, the electrical cable 650 can be integrated into and permanently attached to the handle portion 640 of the injector 620.

As shown in FIG. 24, the system 600 includes a sensor system 660 that includes a series of electrodes 662 at the working end 605 of the introducer 620. In the illustrated embodiment, the electrodes 662 are ring-like electrodes, though other suitable configurations can be used (e.g., helical shaped electrodes). Though FIG. 24 shows five electrodes 662, the sensor system 660 can have more or fewer electrodes. In the illustrated embodiment, the electrodes 662 are defined by circumferential rings of exposed surfaces of a metal cannula, where the amorphous diamond-like carbon coating has been removed, for example, by etching. In use, the low voltage current provide by the electrical source 125A is coupled to the ring-like electrodes 662 from a second opposing polarity electrode in the working end 605 (or a remote electrode such as a ground pad). As bone cement covers the ring-like electrodes 660, impedance will change to thus allow a signal of retrograde bone cement migration, as described above, to be generated and communicated by the controller 125B to the operator. In one embodiment, the electrical source 125A provides energy to the electrodes 662 for sensing a retrograde flow. In another embodiment, the electrical source 125B provides energy to the electrodes 662 for heating of bone cement (e.g., polymerization of bone cement0 or tissue.

FIG. 25 shows a schematic partial cross-sectional view of the introducer 620. The introducer 620 in FIG. 25 is similar to the introducer 320 in FIG. 23B, except as noted below. Thus, the reference numerals used to designate the various features of the introducer 620 are identical to those used for identifying the corresponding features of the introducer 320, except as noted below. In the illustrated embodiment, the introducer 620 includes the thermal energy embitter 420', which includes the resistive heating element 422, coupled to the electrical source 125A and controller 125B. The source of fill material 145 provides a flow of bone infill material (e.g., bone cement) through the flow passageway 424, which extends through the introducer 620 to the outlet opening 325. As discussed above, the introducer 620 has the coating 625 disposed over an outer surface thereof. As shown in FIG. 25, the introducer 620 also has an amorphous diamond-like carbon (DLC) or a diamond-like nanocomposite (DCN) coating 630 within the interior passageway 424 of the bone cement injector 620, though the injector can be of any type described above.

Suitable amorphous diamond-like carbon coatings and diamond-like nanocomposites are available from Bekaert Progressive Composites Corporations, 2455 Ash Street, Vista, Calif. 92081 or its parent company or affiliates. Further information on said coatings can be found at: http://www.bekaert-.com/bac/Products/Diamond-like%20coatings.htm, the contents of which are incorporated herein by reference. The diamond-like coatings preferably comprise amorphous carbon-based coatings with high hardness and low coefficient of friction. The amorphous carbon coatings advantageously exhibit non-stick characteristics and excellent wear resistance. The coatings are preferably thin, chemically inert and have a very low surface roughness. In one embodiment, the coatings have a thickness ranging between about 0.001 mm and about 0.010 mm. In another embodiment, the coatings have a thickness ranging between about 0.002 mm and about 0.005 mm. The diamond-like carbon coatings are preferably a composite of sp2 and sp3 bonded carbon atoms with a hydrogen concentration of between about 0% and about 80%. Another suitable diamond-like nanocomposite coating (a-C: H/a-Si:O; DLN) is made by Bakaert and is suitable for use in the bone cement injector described above. The materials and coatings are known by the names Dylyn®Plus, Dylyn®/DLC and Cavidur®.

In another embodiment, the metal-doped amorphous diamond-like carbon or diamond-like nanocomposite can be used in an electrosurgical surface of a blade, needle, probe, jaw surface, catheter working end and the like. In one embodiment, the surface of a probe or jaw can comprise a pattern of metal-doped amorphous diamond-like carbon portions and adjacent or surrounding insulative amorphous diamond-like carbon portions.

In another embodiment, the amorphous diamond-like carbon or diamond-like nanocomposite can be used in a high temperature circuit board. Such a circuit board can comprise any insulative substrate together with an electrical circuit deposited thereon, wherein the circuit is of a metal-doped amorphous carbon or diamond-like nanocomposite. The circuit board can use depositions of the DLC or DLN that have a thickness ranging between about 1 micron and 10 microns. The width of the electrical circuit paths have a width of less than about 1000 microns; 100 microns; 10 microns and 1 micron.

In one embodiment, the electrodes 280*a*, 280*b*, 280*c*, 344, 365, 662 do not come in contact with adjacent tissue due to, for example, the presence of a coating on an external surface of the injector 110A, 320, 620, such as coating 625. Accordingly, the electrodes 280*a*, 280*b*, 280*c*, 344, 365, 662 can preferably sense a retrograde flow without being in direct contact with bone cement or tissue, and can direct energy to said bone cement or tissue without being in direct contact with the same to, for example, coagulate tissue or polymerize bone cement.

In another embodiment, energy can be delivered via the electrodes 280*a*, 280*b*, 280*c*, 344, 365, 662 of the systems described above to heat surrounding tissue prior to introduction of bone cement into the vertebra. In another embodiment, energy can be delivered via the electrodes 280*a*, 280*b*, 280*c*, 344, 365, 662 of the systems described above to heat surrounding tissue and bone cement prior to introduction of additional bone cement into the vertebra.

The features described herein are further applicable to cure-on-demand fill materials that can be used for disc nucleus implants, wherein the conductive fill material is injected to conform to the shape of a space and wherein Rf current is then applied to increase the modulus of the material on demand to a desired level that is adapted for dynamic stabilization. Thus, the Rf conductive fill material 120, 345 can be engineered to reach a desired modulus that is less than that of a hardened fill material used for bone support. In this embodiment, the fill material is used to support a disc or portion thereof. The cure-on-demand fill material also can be configured as an injectable material to repair or patch a disc annulus as when a tear or herniation occurs The features described herein are further applicable to cure-on-demand fill materials that can be used for plastic surgery and reconstructive surgery wherein the conductive fill material is injected to conform to a desired shape, for example in facial plastics for chin implants, nasal implants, check implants or breast implants and the like.

The features described herein are further applicable to cure-on-demand fill material that can be used for injection into a space between vertebrae for intervertebral fusion. The injection of fill material can conform to a space created between two adjacent vertebrae, or can be injected into notches or bores in two adjacent vertebrae and the intervening space, and then cured by application of Rf current to provide a substantially high modulus block to cause bone fusion.

In any embodiment such as for intervertebral fusion or for bone support in VCFs, the system can further include the injection of a gas (such as carbon dioxide) into the fill material before it is injected from a high pressure source. Thereafter, the gas can expand to form voids in the fill material as it is cured to create porosities in the hardened fill material for allowing rapid bone ingrowth into the fill material.

The systems described herein can use any suitable energy source, other that radiofrequency energy, to accomplish the purpose of altering the viscosity of the fill material 120, 345. The method of altering fill material can be at least one of a radiofrequency source, a laser source, a microwave source, a magnetic source and an ultrasound source. Each of these energy sources can be configured to preferentially deliver energy to a cooperating, energy sensitive filler component carried by the fill material. For example, such filler can be suitable chromophores for cooperating with a light source, ferromagnetic materials for cooperating with magnetic inductive heating means, or fluids that thermally respond to microwave energy.

The features described herein are further applicable to additional filler materials, such as porous scaffold elements and materials for allowing or accelerating bone ingrowth. In any embodiment, the filler material can comprise reticulated or porous elements of the types disclosed in co-pending U.S. patent application Ser. No. 11/146,891, filed Jun. 7, 2005, titled "Implants and Methods for Treating Bone" which is incorporated herein by reference in its entirety and should be considered a part of this specification. Such fillers also can carry bioactive agents. Additional fillers, or the conductive filler, also can include thermally insulative solid or hollow microspheres of a glass or other material for reducing heat transfer to bone from the exothermic reaction in a typical bone cement component.

Of course, the foregoing description is that of certain features, aspects and advantages of the present invention, to which various changes and modifications can be made without departing from the spirit and scope of the present invention. Moreover, the bone treatment systems and methods need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone treatment systems and methods.

What is claimed is:

1. A system for delivering a bone fill material to a vertebra, comprising:
    an in-situ hardenable bone fill material comprising a two-part curable polymer;
    an elongated introducer configured for insertion into a vertebral body and delivery of bone fill material through a channel of the introducer into the vertebral body;
    a container of bone fill material coupleable to the introducer;
    a thermal energy emitter coupled to the introducer and configured to apply thermal energy to the bone fill material flowing through the introducer;
    a hydraulic pressure source coupled to the container and configured to apply a force on the bone fill material in the container to eject bone fill material from the container into the introducer;
    a sensor for providing data relating to the bone fill material, the data being a measured parameter of the bone fill material and comprising at least one of temperature, impedance, capacitance, conductivity, pressure, viscosity, a flow parameter, volume, reflectance, an optical parameter, and an acoustical parameter; and
    a computer controller configured to receive the data from the sensor and to control, based at least in part on the data, 1) the thermal energy applied to the flow of bone fill material and 2) the force from the hydraulic pressure source applied to the bone fill material, the computer controller thereby configured to control both the increase in viscosity of the bone fill material and the flow of bone fill material.

2. The system of claim 1, further comprising a flexible tube and a piston, wherein the hydraulic pressure source couples to the container via the flexible tube and is configured to selectively drive the piston disposed in the container to eject bone fill material from the container.

3. The system of claim 2, wherein the piston is a floating piston configured to move within the container between a proximal end coupled to the flexible tube and a distal end coupled to the introducer, the container having a larger diameter than the introducer, the flexible tube comprising a hydraulic line, the piston driven hydraulically by a liquid within the hydraulic line toward the distal end of the container to drive bone fill material from the container into the introducer.

4. The system of claim 1, wherein the thermal energy emitter is selected from the group consisting of an electromagnetic energy emitter, a radiofrequency energy emitter, a resistive heat emitter, a light energy emitter, a microwave emitter, an inductive heat emitter and an ultrasound emitter.

5. The system of claim 1, wherein the thermal energy emitter is disposed in the channel of the introducer proximal at least one opening of the introducer.

6. The system of claim 5, further comprising an insulative layer between the thermal energy emitter and a wall of the introducer.

7. The system of claim 1, wherein the thermal energy emitter is a resistive heat emitter.

8. The system of claim 7, wherein the resistive heat emitter has an axial configuration.

9. The system of claim 7, wherein the resistive heat emitter has a helical configuration.

10. The system of claim 7, wherein the thermal energy emitter is configured to raise a temperature of the bone fill material flowing through the channel to at least about 45° C.

11. The system of claim 7, wherein the resistive heat emitter comprises a positive temperature coefficient (PTC) material configured to provide a generally uniform temperature from the emitter.

12. The system of claim 7, further comprising an electrical source coupled to the resistive heat emitter, the electrical source configured to provide a current to the resistive heat emitter.

13. The system of claim 1, further comprising a cooling system configured to cool the bone fill material within the container prior to ejection into the introducer and prior to the application of thermal energy within the introducer.

14. The system of claim 1, wherein the sensor is configured to measure a parameter of the bone fill material within the container of bone fill material.

15. A system for delivering a bone fill material to a bone, comprising:
    an elongated introducer configured for insertion into a bone, the introducer defining a channel sized to allow a flow of a bone fill material therethrough, the introducer having at least one opening in communication with the channel for delivering the bone fill material into the bone;
    a thermal energy emitter configured to apply thermal energy to the bone fill material within the introducer; and
    a hydraulic pressure source operatively coupled to the introducer and configured to apply a force on the bone fill material to provide a pressurized flow of bone fill material through the introducer;

a sensor for providing data relating to the bone fill material, the data being a measured parameter of the bone fill material and comprising at least one of temperature, impedance, capacitance, conductivity, pressure, viscosity, a flow parameter, volume, reflectance, an optical parameter, and an acoustical parameter; and a computer controller configured to receive the data from the sensor and to control the flow rate of the bone fill material to thereby control application of thermal energy from the thermal energy emitter to the bone fill material at least in response to the data from the sensor to thereby controllably increase the viscosity of the bone fill material injected into the bone.

16. The system of claim 15, wherein the hydraulic pressure source is configured to apply force through a flexible tube.

17. The system of claim 16, further comprising a piston, wherein the hydraulic pressure source is configured to selectively drive the piston to eject bone fill material from the introducer.

18. The system of claim 17, wherein the piston is a floating piston.

19. The system of claim 16, further comprising a cooling system configured to cool the bone fill material.

20. The system of claim 15, wherein the thermal energy emitter is selected from the group consisting of an electromagnetic energy emitter, a resistive heat emitter, a radiofrequency energy emitter, a light energy emitter, a microwave emitter, an inductive heat emitter and an ultrasound source.

21. The system of claim 15, wherein the thermal energy emitter is disposed in the channel of the introducer proximal at least one opening of the introducer.

22. The system of claim 15, wherein the sensor is configured to measure a parameter of the bone fill material that is within the system.

23. A system for delivering a bone cement into a bone, comprising:

an in-situ hardenable bone cement;

a cement introducer system having an introducer configured for insertion into a bone, the introducer defining a channel for carrying the bone cement, the introducer having at least one opening in communication with the channel for delivering the bone cement into the bone;

a thermal energy emitter configured to apply thermal energy to the bone cement within the cement introducer system;

a cooling system configured to cool the bone cement within the cement introducer system, wherein the cooling system is configured to cool the bone cement in a first section of the cement introducer system and the thermal energy emitter is configured to apply thermal energy to the bone cement in a second section of the cement introducer system separate from the first section;

a sensor for providing data relating to the bone cement, the data being a measured parameter of the bone cement and comprising at least one of temperature impedance, capacitance, conductivity, pressure, viscosity, a flow parameter, volume, reflectance, an optical parameter, and an acoustical parameter; and a computer controller configured to receive the data from the sensor and to control the application of thermal energy from the thermal energy emitter to the bone cement flowing through the introducer system into the bone at least in response to the data from the sensor and to control the flow of bone cement to thereby controllably increase the viscosity of the bone cement injected into the bone.

24. The system of claim 23, wherein the controller is further configured to control the operation of the cooling system.

25. The system of claim 23, wherein the thermal energy emitter and the cooling system are configured such that the bone cement can be cooled during mixing and storage of the bone cement and heated during delivery through the introducer.

26. The system of claim 23, further comprising a hydraulic pressure mechanism comprising a hydraulic line and a floating piston, coupled to the cement introducer system and configured to hydraulically drive the piston by a liquid within the hydraulic line to apply a force on the bone cement and to eject bone cement from the cement introducer system.

27. The system of claim 23, wherein the cooling system comprises a thermoelectric system with at least one Peltier element in contact with a thermally conductive wall portion of the first section of the cement introducer system.

28. The system of claim 23, wherein the cooling system comprises at least one of a chilled fluid circulation system, and a Freon system.

29. The system of claim 23, wherein the cooling system is a passive cooling system.

30. The system of claim 29, wherein the passive cooling system comprises an open cell graphite structure for conducting heat away from the first section of the cement introducer system to a heat exchanger component.

31. The system of claim 23, wherein the sensor is configured to measure a parameter of the bone fill material within the cement introducer system.

32. The system of claim 31, wherein the sensor is configured to measure a parameter of the bone fill material within the first section of the cement introducer system.

* * * * *

UNITED STATES PATENT AND TRADEMARK OFFICE
CERTIFICATE OF CORRECTION

PATENT NO. : 8,066,712 B2  
APPLICATION NO. : 11/469752  
DATED : November 29, 2011  
INVENTOR(S) : Truckai et al.

Page 1 of 1

It is certified that error appears in the above-identified patent and that said Letters Patent is hereby corrected as shown below:

At column 17, line 22, delete "polymide" and insert --polyimide--, therefor.

At column 18, line 40, delete "14BA)." and insert --14A).--, therefor.

At column 19, line 60, delete "is which" and insert --in which--, therefor.

At column 20, line 46, delete "and or" and insert --and/or--, therefor.

At column 20, line 48, delete "10A" and insert --110A--, therefor.

At column 29, line 10, delete "cement0" and insert --cement--, therefor.

At column 29, line 51, delete "Bakaert" and insert --Bekaert--, therefor.

At column 30, line 37, delete "occurs" and insert --occurs.--, therefor.

At column 34, line 6, in claim 23, delete "temperature" and insert --temperature,--, therefor.

Signed and Sealed this  
Seventeenth Day of April, 2012

David J. Kappos  
*Director of the United States Patent and Trademark Office*